US007596608B2

(12) United States Patent  
Alexander et al.

(10) Patent No.: US 7,596,608 B2  
(45) Date of Patent: Sep. 29, 2009

(54) NETWORKED EMERGENCY MANAGEMENT SYSTEM

(75) Inventors: John S. Alexander, Westfield, NJ (US); Nathaniel J. Weiss, Westfield, NJ (US)

(73) Assignee: LiveProcess Corporation, Verona, NJ (US)

( * ) Notice: Subject to any disclaimer, the term of this patent is extended or adjusted under 35 U.S.C. 154(b) by 0 days.

(21) Appl. No.: 11/349,422

(22) Filed: Feb. 7, 2006

(65) Prior Publication Data

US 2006/0224629 A1 Oct. 5, 2006

Related U.S. Application Data

(60) Provisional application No. 60/663,463, filed on Mar. 18, 2005.

(51) Int. Cl.  
*G06F 15/16* (2006.01)

(52) U.S. Cl. .................. 709/217; 709/218; 709/219

(58) Field of Classification Search ........... 709/217, 709/218, 219  
See application file for complete search history.

(56) References Cited

U.S. PATENT DOCUMENTS

| 4,962,473 | A | * | 10/1990 | Crain ................... 340/541 |
| 5,644,740 | A | * | 7/1997 | Kiuchi ................... 715/853 |
| 5,726,884 | A | | 3/1998 | Sturgeon et al. |
| 5,815,417 | A | * | 9/1998 | Orr et al. ................ 703/5 |
| 5,832,497 | A | * | 11/1998 | Taylor ................ 707/104.1 |
| 6,023,223 | A | * | 2/2000 | Baxter, Jr. ............ 340/531 |
| 6,266,784 | B1 | * | 7/2001 | Hsiao et al. .............. 714/6 |
| 6,347,384 | B1 | * | 2/2002 | Satomi et al. ............ 714/57 |
| 6,449,598 | B1 | * | 9/2002 | Green et al. .............. 705/2 |
| 6,463,430 | B1 | * | 10/2002 | Brady et al. ............. 707/3 |
| 6,516,424 | B2 | * | 2/2003 | Satomi et al. ............. 714/4 |

(Continued)

FOREIGN PATENT DOCUMENTS

EP 513601 A1 * 11/1992

(Continued)

OTHER PUBLICATIONS

Botterell, A. et al., Public Warning in the Networked Age: Open Standards to the Rescue?, Mar. 2007, Communications of the ACM, vol. 50, Issue 3, pp. 59-60.*

(Continued)

*Primary Examiner*—Jeffrey Pwu  
*Assistant Examiner*—Alicia Baturay  
(74) *Attorney, Agent, or Firm*—Panitch Schwarze Belisario & Nadel LLP

(57) ABSTRACT

A computer-implemented process allows emergency plans to be easily and rapidly created for a plurality of different facilities. An emergency plan is provided in electronic form for each facility. Each emergency plan has a standardized format with a plurality of component parts. Each emergency plan has at least some component parts that are accessible by other facilities. An electronic network is provided which allows at least some of the facilities to electronically obtain the accessible component parts of the emergency plans of at least some of the other facilities. A user interface allows the emergency plan of a facility to electronically import into its emergency plan selected content of one or more component parts of the emergency plan of another facility using the electronic network. The electronic importing is facilitated via the use of the standardized format for the emergency plans.

22 Claims, 76 Drawing Sheets

U.S. PATENT DOCUMENTS

| | | | |
|---|---|---|---|
| 6,567,502 B2 * | 5/2003 | Zellner et al. | 379/45 |
| 6,574,561 B2 * | 6/2003 | Alexander et al. | 702/5 |
| 6,604,126 B2 * | 8/2003 | Neiman et al. | 709/203 |
| 6,631,326 B1 * | 10/2003 | Howard et al. | 702/5 |
| 6,646,549 B2 * | 11/2003 | Dawson | 340/531 |
| 6,745,187 B2 * | 6/2004 | Singer et al. | 707/9 |
| 6,748,400 B2 * | 6/2004 | Quick | 707/104.1 |
| 6,754,674 B2 * | 6/2004 | Meyers et al. | 707/104.1 |
| 6,868,340 B2 * | 3/2005 | Alexander et al. | 702/5 |
| 6,937,147 B2 * | 8/2005 | Dilbeck et al. | 340/506 |
| 6,999,876 B2 * | 2/2006 | Lambert et al. | 702/2 |
| 7,010,097 B2 * | 3/2006 | Zellner et al. | 379/45 |
| 7,058,710 B2 * | 6/2006 | McCall et al. | 709/224 |
| 7,134,088 B2 * | 11/2006 | Larsen | 715/765 |
| 7,148,795 B2 * | 12/2006 | Dilbeck et al. | 340/506 |
| 7,156,655 B2 * | 1/2007 | Sachdeva et al. | 433/24 |
| 7,177,398 B2 * | 2/2007 | Meer et al. | 379/45 |
| 7,194,395 B2 * | 3/2007 | Genovese | 703/6 |
| 7,200,207 B2 * | 4/2007 | Meer et al. | 379/45 |
| 7,280,038 B2 * | 10/2007 | Robinson | 340/506 |
| 2001/0027472 A1 * | 10/2001 | Guan | 709/203 |
| 2002/0013716 A1 * | 1/2002 | Dunham et al. | 705/2 |
| 2002/0059246 A1 * | 5/2002 | Rowe | 707/10 |
| 2002/0084900 A1 * | 7/2002 | Peterson et al. | 340/573.1 |
| 2002/0116242 A1 * | 8/2002 | Vercellone et al. | 705/7 |
| 2002/0161614 A1 * | 10/2002 | Spira et al. | 705/7 |
| 2002/0188522 A1 * | 12/2002 | McCall et al. | 705/26 |
| 2002/0188568 A1 * | 12/2002 | Nickolaisen et al. | 705/52 |
| 2003/0004693 A1 * | 1/2003 | Neiman et al. | 703/1 |
| 2003/0105649 A1 * | 6/2003 | Sheiner et al. | 705/2 |
| 2003/0135500 A1 * | 7/2003 | Chevrel et al. | 707/9 |
| 2004/0008125 A1 * | 1/2004 | Aratow et al. | 340/870.07 |
| 2004/0044553 A1 * | 3/2004 | Lambert et al. | 705/7 |
| 2004/0064436 A1 * | 4/2004 | Breslin et al. | 707/1 |
| 2004/0103431 A1 * | 5/2004 | Davenport et al. | 725/33 |
| 2004/0145481 A1 | 7/2004 | Dilbeck et al. | |
| 2004/0172277 A1 * | 9/2004 | Dione | 705/1 |
| 2004/0243446 A1 * | 12/2004 | Wyatt | 705/2 |
| 2005/0003797 A1 * | 1/2005 | Baldwin | 455/404.1 |
| 2005/0015222 A1 | 1/2005 | Harrington | |
| 2005/0132305 A1 * | 6/2005 | Guichard et al. | 715/855 |
| 2005/0209770 A1 * | 9/2005 | O'Neill et al. | 701/117 |
| 2005/0220277 A1 * | 10/2005 | Blalock et al. | 379/45 |
| 2005/0251405 A1 * | 11/2005 | Kreiner et al. | 705/1 |
| 2005/0251417 A1 * | 11/2005 | Malhotra et al. | 705/2 |
| 2005/0267651 A1 * | 12/2005 | Arango et al. | 701/3 |
| 2006/0020992 A1 * | 1/2006 | Pugel et al. | 725/108 |
| 2006/0031938 A1 * | 2/2006 | Choi | 726/25 |
| 2006/0109113 A1 * | 5/2006 | Reyes et al. | 340/541 |
| 2006/0168185 A1 * | 7/2006 | McCall et al. | 709/223 |
| 2006/0224629 A1 * | 10/2006 | Alexander et al. | 707/104.1 |
| 2006/0255927 A1 * | 11/2006 | Dilbeck et al. | 340/506 |
| 2006/0271563 A1 * | 11/2006 | Angelo et al. | 707/100 |
| 2007/0015506 A1 * | 1/2007 | Hewett et al. | 455/432.3 |
| 2007/0083409 A1 * | 4/2007 | Dilbeck et al. | 705/7 |
| 2007/0103288 A1 * | 5/2007 | Herard, Jr. | 340/506 |

FOREIGN PATENT DOCUMENTS

| | | | | |
|---|---|---|---|---|
| JP | 07093046 | A | * | 4/1995 |
| JP | 10240805 | A | * | 9/1998 |
| JP | 2000316820 | A | * | 11/2000 |
| JP | 2001236411 | A | * | 8/2001 |
| JP | 2001319030 | A | * | 11/2001 |
| JP | 2001350843 | A | * | 12/2001 |
| JP | 2005018285 | A | * | 1/2005 |

OTHER PUBLICATIONS

Brady, T., Public Health: Emergency Management: Capability Analysis of Critical Incident Response, 2003, Proceedings of the 35th conference on Winter Simulation: Driving Innovation, pp. 1863-1867.*

Carver, L. et al., Human-Computer Interaction: the Human and Computer as a Team in Emergency Management Information Systems, Mar. 2007, Communications of the ACM, vol. 50, Issue 3, pp. 33-38.*

Currion, P. et al., Open Source Software for Disaster Management, Mar. 2007, Communications of the ACM, vol. 50, Issue 3, pp. 61-65.*

Fiedrich F. et al., Agent-Based Systems for Disaster Management, Mar. 2007, Communications of the ACM, vol. 50, Issue 3, pp. 41-42.*

French, S. et al., Decision Support Systems, Mar. 2007, Communications of the ACM, vol. 50, Issue 3, pp. 39-40.*

Harrald, J. et al., Shared Situational Awareness in Emergency Management Mitigation and Response, 2007, Proceedings of the 40th Annual Hawaii International Conference on System Sciences (HICSS'07), pp. 1-8.*

Manoj, B.S. et al., Communication Challenges in Emergency Response, Mar. 2007, Communications of the ACM, vol. 50, Issue 3, pp. 51-53.*

Mendonça, D. et al., Collaborative Adhocracies and Mix-and-Match Technologies in Emergency Management, Mar. 2007, Communications of the ACM, vol. 5, Issue 3, pp. 45-49.*

Palen, L. et al., Online Forums Supporting Grassroots Participation in Emergency Preparedness and Response, Mar. 2007, Communications of the ACM, vol. 50, Issue 3, pp. 54-58.*

Raman, M., et al., Knowledge Management System for Emergency Preparedness: An Action Research Study, Jan. 2006, Proceedings of the 39th Annual Hawaii International Conference on System Sciences (HICSS'06), pp. 1-10.*

Swigger, K. et al, Research Issues Related to Exchanging Information from Heterogeneous Data Sources, 2006, Proceedings of the 2006 international conference on Digital government research, ACM International Conference Proceeding Series, vol. 151, pp. 45-46.*

Turoff, M. et al., Assuring Homeland Security: Continuous Monitoring, Control & Assurance of Emergency Preparedness, Sep. 2004, Journal of Information Technology Theory and Application (JITTA), vol. 6, No. 3, pp. 1-34.*

Turoff, M. et al., The Design of a Dynamic Emergency Response Management Information System (DERMIS), Summer 2004, Journal of Information Technology Theory and Application (JITTA), vol. 5, No. 4, pp. 1-32.*

Turoff, M., Past and Future Emergency Response Information Systems, Apr. 2002, Communications of the ACM, vol. 45, Issue 4, pp. 29-32.*

Van de Walle, B. et al., Emergency Response Information Systems: Emerging Trends and Technologies, Mar. 2007, Communications of the ACM, vol. 50, Issue 3, pp. 29-31.*

Caro, D., Towards Integrated Crisis Support of Regional Emergency Networks, Fall 1999, Health Care Management Review, vol. 24, Issue 4, pp. 7-19.*

Frishberg, Looking back at plan AHEAD™: Exercising User-Centered Design in Emergency Management, Apr. 2-7, 2005, ACM, Conference on Human Factors in Computing Systems, pp. 988-1003.*

The Hospital Emergency Incident Command System (HEICS), Third Edition, Jun. 1998, vol. 1, developed by The San Mateo County Health Services Agency, Emergency Medical Services (96 pages).

* cited by examiner

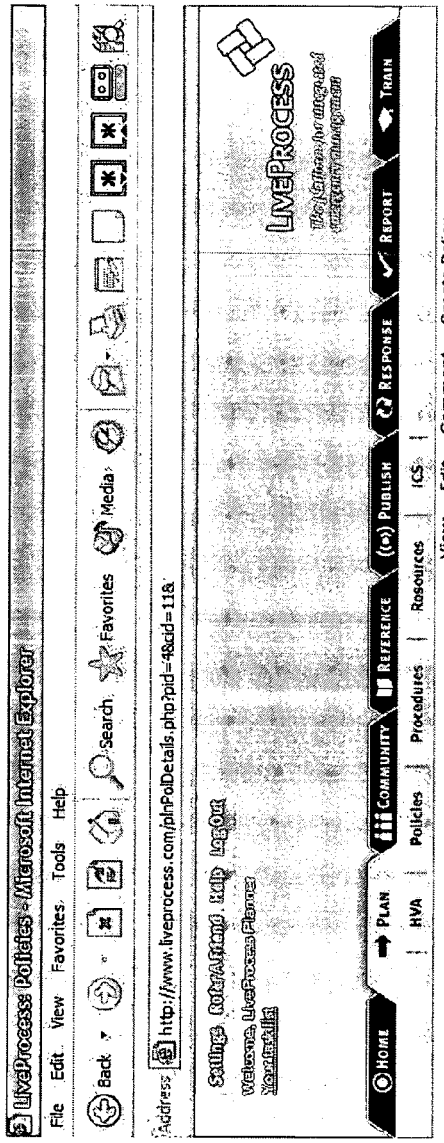

Noble Hospital Organization and Management: Code Triage - Code C (Chemical)

1. Scope
2. Purpose
3. Policy
4. Procedure
5. External Procedure
6. Internal Procedure
7. Preparation Of Decon Area
8. Donning Protective Clothing
9. Doffing Protective Clothing
10. Code Yellow Team Leader
11. Security Officer: Responsibilities
12. Environmental Services: Responsibilities
13. Respiratory Therapy: Responsibilities

Scope

All Hospital Departments.

Purpose

Chemical decontamination has 2 primary goals: first, decontamination helps prevent further harm to the patient from the chemical exposure and secondly, c providers and maintains the viability of the Emergency Department (ED) as a treatment center. Methods of patient decontamination include chemical dilution during decontamination may result in illness in healthcare providers and contamination of the ED. Severe ED contamination may necessitate departmental cl mass casualty incident.

Noble Hospital Organization and Management: HVA for the Noble Plan

| Hazard | Likelihood 0-3 | Human Impact 0-3 | Property Impact 0-3 | Business Impact 0-3 | Preparedness 0-3 | Internal Response 0-3 | External Response 0-3 | Risk 0-3 |
|---|---|---|---|---|---|---|---|---|
| Natural Hazards | | | | | | | | |
| Severe Weather | 2 | 1 | 2 | 3 | 2 | 1 | 1 | 37 |
| Flood | 3 | 1 | 1 | 1 | 1 | 1 | 1 | 33.3 |
| Tornado | 2 | 1 | 3 | 3 | 3 | 3 | 3 | 59.3 |
| Hurricane | 1 | 1 | 1 | 1 | 1 | 1 | 1 | 11.1 |
| Ice Storm | 1 | 1 | 1 | 1 | 1 | 1 | 1 | 11.1 |
| Drought | 2 | 1 | 1 | 1 | 1 | 1 | 1 | 22.2 |
| Wildfire | 2 | 1 | 1 | 1 | 1 | 1 | 1 | 22.2 |
| Dam Failure | 0 | 0 | 0 | 0 | 0 | 0 | 0 | 0 |
| Earthquake | 0 | 0 | 0 | 0 | 0 | 0 | 0 | 0 |
| Air Pollution | 3 | 3 | 3 | 1 | 1 | 1 | 1 | 55.6 |
| Technological Hazards | | | | | | | | |
| Radiological Transportation | 2 | 1 | 0 | 1 | 1 | 1 | 1 | 18.5 |
| Hazmat, External | 3 | 3 | 2 | 3 | 3 | 3 | 3 | 100 |
| Transportation Spills | 3 | 2 | 2 | 2 | 2 | 2 | 2 | 66.7 |
| Utilities Failures | | | | | | | | |
| Medical Gas Failure | 1 | 2 | 3 | 3 | 3 | 3 | 3 | 31.5 |
| Power Failure | 2 | 1 | 3 | 3 | 3 | 3 | 3 | 59.3 |
| Water Failure | 2 | 1 | 3 | 3 | 3 | 3 | 3 | 59.3 |
| Information Systems Failure | 1 | 1 | 1 | 1 | 1 | 1 | 1 | 11.1 |
| HVAC Failure | 2 | 1 | 2 | 2 | 2 | 2 | 2 | 40.7 |
| Sewer Failure | 2 | 1 | 2 | 2 | 2 | 2 | 2 | 20.4 |
| Steam Failure | 2 | 1 | 2 | 2 | 2 | 2 | 2 | 40.7 |
| PBX Paging System | 2 | 0 | 0 | 0 | 0 | 0 | 0 | 0 |
| Medical Vacuum Failure | 2 | 1 | 2 | 2 | 2 | 2 | 2 | 40.7 |
| Natural Gas Leak | 1 | 2 | 2 | 2 | 2 | 2 | 2 | 22.2 |
| Fire Alarm Failure | 2 | 3 | 2 | 2 | 2 | 2 | 2 | 46.1 |
| Structural Damage | 1 | 3 | 3 | 3 | 3 | 3 | 3 | 33.3 |
| Telephone Failure | 2 | 1 | 1 | 1 | 1 | 1 | 1 | 22.2 |
| Fuel Shortage | 1 | 1 | 1 | 1 | 1 | 1 | 1 | 11.1 |
| Fire, Internal | 1 | 3 | 3 | 3 | 3 | 3 | 3 | 33.3 |
| Explosion | 1 | 3 | 3 | 3 | 3 | 3 | 3 | 33.3 |
| National/Security Emergencies | | | | | | | | |
| Nuclear Threat | 2 | 3 | 3 | 3 | 3 | 3 | 3 | 66.7 |
| Terrorism, Biological | 2 | 3 | 3 | 3 | 3 | 3 | 3 | 66.7 |
| Terrorism, Chemical | 2 | 3 | 3 | 3 | 3 | 3 | 3 | 66.7 |
| Civil Disturbance | 2 | 2 | 2 | 2 | 2 | 2 | 2 | 44.4 |
| Airplane Crash | 1 | 3 | 1 | 1 | 1 | 1 | 1 | 14.8 |
| Bomb Threat | 1 | 3 | 3 | 3 | 3 | 3 | 3 | 33.3 |
| Hostage/Barricade | 2 | 2 | 2 | 2 | 2 | 2 | 2 | 44.4 |
| Food Preparation | 1 | 2 | 2 | 2 | 1 | 1 | 1 | 16.7 |
| Water Supply | 1 | 2 | 2 | 2 | 1 | 1 | 1 | 16.7 |

Noble Hospital Organization and Management: HVA for the Noble Plan

| Hazard | Likelihood 0=Low 3=High | Human Impact 0=Low 3=High | Property Impact 0=Low 3=High | Business Impact 0=Low 3=High | Preparedness 3=Low 0=High | Internal Response 3=Low 0=High | External Response 3=Low 0=High | Risk 0-8 |
|---|---|---|---|---|---|---|---|---|
| Natural Hazards | | | | | | | | |
| Severe Weather | 2 | 1 | 2 | 3 | 2 | 1 | 1 | 37 |
| Flood | 3 | 1 | 1 | 3 | 3 | 3 | 1 | 33.3 |
| Tornado | 2 | 1 | 3 | 3 | 3 | 3 | 3 | 59.3 |
| Hurricane | 1 | 1 | 1 | 1 | 1 | 1 | 1 | 11.1 |
| Ice Storm | 1 | 1 | 1 | 1 | 1 | 1 | 1 | 11.1 |
| Drought | 2 | 1 | 1 | 1 | 1 | 1 | 1 | 22.2 |
| Wildfire | 2 | 1 | 1 | 1 | 1 | 1 | 1 | 22.2 |

FIGURE 39

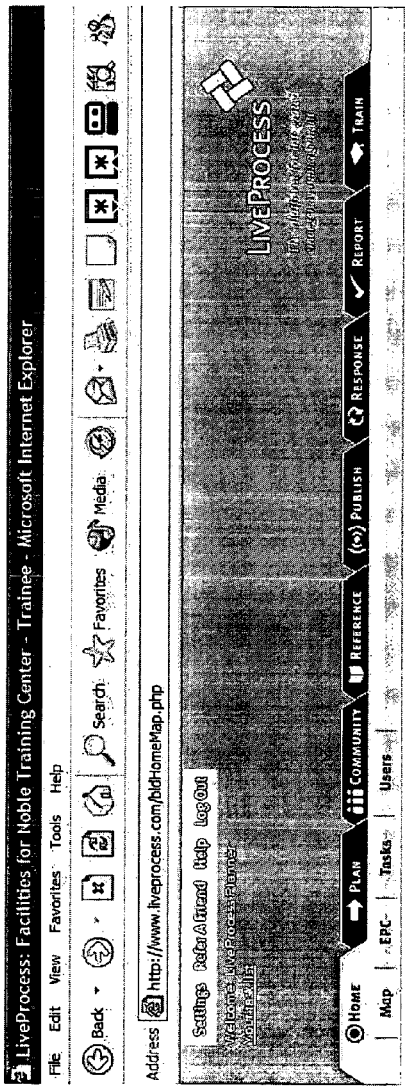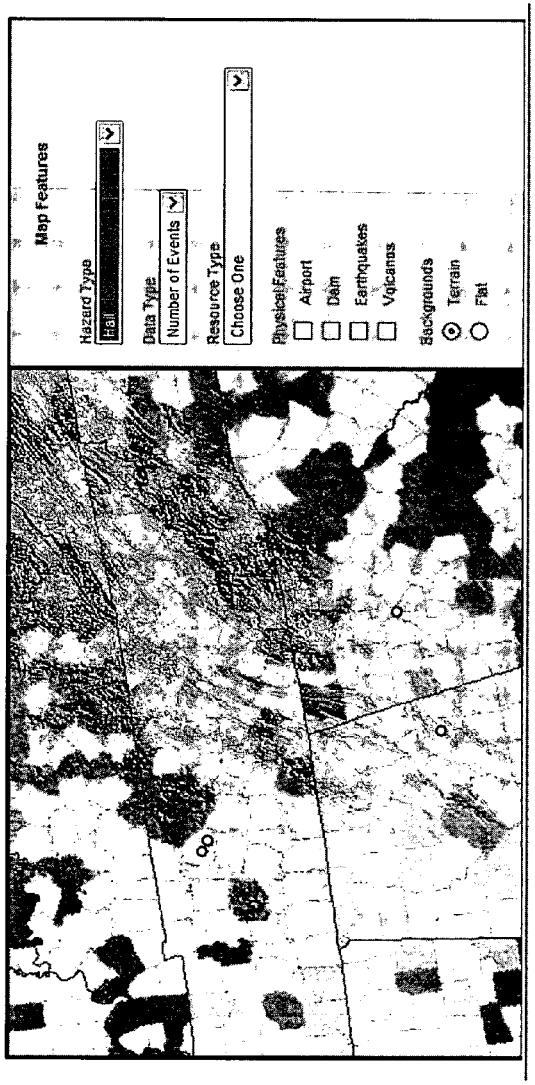
FIGURE 52

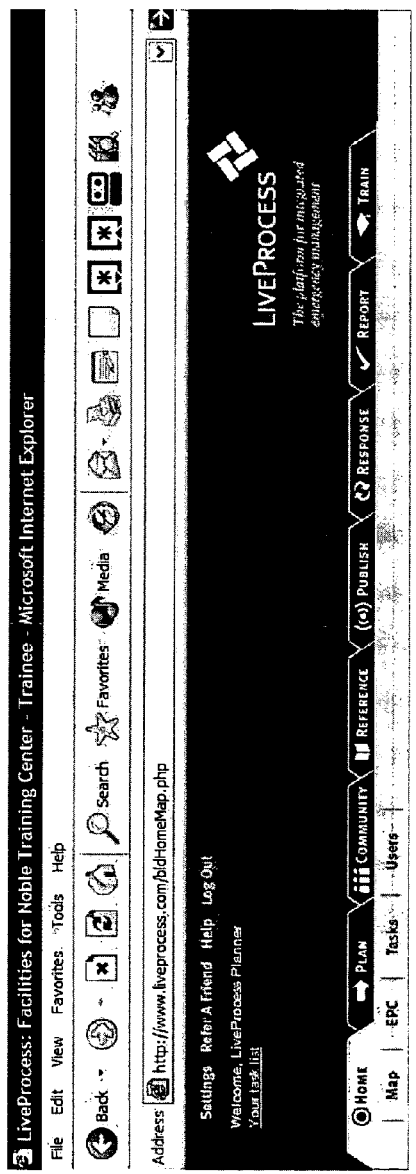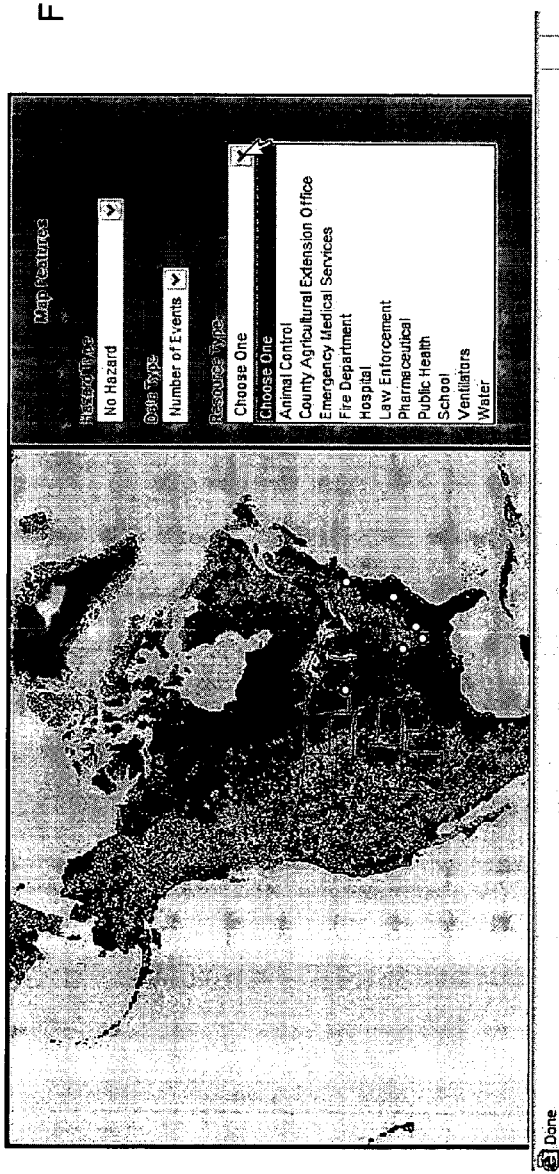
FIGURE 53
LiveProcess: Facilities for Noble Training Center - Trainee

| | Threads | Posts | Last post |
|---|---|---|---|
| General Discussion | | | |
| General<br>General Forum<br>*Moderator: Admin, meleeano* | 26 | 97 | NDMS<br>(kgordon) - 02/19/05 10:37 AM |
| Disasters & Events<br>Forum about disasters and events<br>*Moderator: Admin* | 13 | 50 | Re: Chlorine Gas Released ...<br>(kgordon) - 01/27/05 09:19 AM |
| Public Health<br>A forum to discuss public health<br>*Moderator: Admin* | 7 | 26 | Re: HHS Pandemic Plan -- A...<br>(lwurtz) - 12/06/04 01:10 PM |
| Administration<br>Issues in Hospital Administration in the area of Disaster Response<br>*Moderator: Admin* | 3 | 15 | Re: Financial benefit of g...<br>(jstarin) - 12/18/04 03:21 PM |
| | Threads | Posts | Last post |
| Planning Discussions | | | |
| Noble Emergency Planning Committee<br>Forum for the Noble Hospital Emergency Planning Committee<br>*Moderator: Admin, jalexander* | 10 | 32 | WELCOME<br>(nweiss) - 09/29/04 03:43 PM |
| Planning Process<br>All about the Planning Process.<br>*Moderator: Admin* | 7 | 21 | Re: Word vs. PDF vs. HTML ...<br>(kgordon) - 01/27/05 09:22 AM |
| What Worked | | | |

NETWORKED EMERGENCY MANAGEMENT SYSTEM

CROSS REFERENCE TO RELATED APPLICATION

This application claims the benefit of U.S. Provisional Patent Application No. 60/663,463 filed Mar. 18, 2005 and entitled "Networked Emergency Management System."

COMPACT DISC APPENDIX

This patent application includes an Appendix on one compact disc having a file named appendix.txt, created on Feb. 7, 2006, and having a size of 1,426,049 bytes. The compact disc is incorporated by reference into the present patent application.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

Natural and man-made disasters are more common than ever. In healthcare, their impact is far more serious than facility damage and standard business continuity and extends to the safety of the patients, employees and surrounding community. Yet most hospital emergency managers use a word processor to create emergency management plans and training materials and store them in cumbersome three-ring binders. This makes updating the plan, running drills and responding to an emergency difficult, time-intensive and often ineffective. In addition to the broader safety issues, these tasks are strictly mandated and monitored by regulatory agencies such as the Joint Commission on Accreditation of Healthcare Organizations (JCAHO) and the Occupational Safety and Health Administration (OSHA), and poor performance has direct impact on Medicare reimbursement, fines, and patient perception. There is a clear unmet need for an easy-to-use solution for creating and updating emergency management plans and training materials.

The Networked Emergency Management System enables emergency managers to share emergency plans and their component parts, best practices, and training materials in a standardized format for the first time. This content is Hospital Emergency Incident Command System (HEICS), National Incident Management System (NIMS) and JCAHO compliant and can be readily customized to one's unique facility. The present invention transforms a traditional emergency management plan from a lengthy and convoluted set of text documents in a three-ring binder into an immediately accessible live process.

Existing emergency management software includes at least the following offerings:

1. Real-time systems designed to focus on broad county-level emergency response. (Examples: WebEOC® available from Emergency Services integrators, Augusta, Ga., World Wide Web.webeoc.com; E Team, available from E Team, Inc., World Wide Web.eteam.com; and Blue 292 software, available from Blue292, Inc., Durham, N.C., World Wide Web.blue292.com).
2. Real-time systems designed to provide information on emergency-room bed availability in the event of an incident. (Examples: Reddinet®, available from Reddinet, Los Angeles, Calif., World Wide Web.reddinet.com; and EMSystem®, available from EMSystem, LLC, Milwaukee, Wis., World Wide Web.emsystem.com).
3. Incident Management software designed for security professionals to document and track incidents or investigations in an emergency in order to recover the most money from federal reimbursement agencies or private insurers. (Example: IRIMS® software available from PPM 2000 Inc., Edmonton, Alberta, Canada, World Wide Web.ppm2000.com).
4. Business Continuity recovery solutions, primarily focused on corporations and their IT systems. (Examples: Software available from Symantec Corporation, Cupertino, Calif., World Wide Web.symantec.com; and Strohl Systems Group Inc., King of Prussia, Pa., World Wide Web.strohlsystems.com).
5. Learning management systems that address compliance and safety. (Examples: PureSafety, Nashville, Tenn., puresafety.com; and Blackboard Inc., Washington, D.C., World Wide Web.blackboard.com)
6. Offerings for Compliance. (Example: Compliance Suite, available from Environmental Support Solutions, Inc. (ESS), Denver, Colo., World Wide Web.ess-home.com)

The present invention is distinct from each of these in that it is a platform focused on healthcare, and it is a solution focused primarily on preparedness and mitigation rather than response or recovery.

BRIEF SUMMARY OF THE INVENTION

The present invention is described in the context of a preferred embodiment of a web-based software application commercialized as LiveProcess™ (World Wide Web.liveprocess.com), which is a platform for integrated emergency management. LiveProcess is a service of LiveProcess Corporation, Chatham, N.J. However, the scope of the present invention is not limited to this particular implementation of the invention. The present invention is described in the context of a plurality of distributed computers, all of which are linked together by an electronic network, such as the Internet. The computers may be any type of computing device that allows a user to interact with a web site via a web browser. For example, the computers may be personal computers (PC) that run a Microsoft Windows® operating system. The computers may also be handheld, wireless devices.

The foundation of the present invention lies in the implementation of a standard organization of the emergency management plan format. (FIG. 10) This format first divides an emergency plan into five areas; a Hazard Vulnerability Analysis (62), emergency policies (63), procedures that must be followed (64), emergency resources that are available to the emergency planner (65) and an Incident Command System command structure, and second, provides a system in which this organization may be utilized. These areas of the emergency plan are common to all emergency plans for all facilities.

Organizing the high level structure in this manner allows the present invention to operate on emergency management plans, allows interoperability of emergency plan components, allows flexibility to accommodate the differences of facilities, and allows the users of emergency management plans to coordinate their efforts in the four areas of emergency management: Mitigation, Planning, Response and Recovery.

The present invention allows emergency planners representing a facility (FIG. 1), or networks of facilities (FIG. 5), to interchange elements of their emergency plans (FIG. 3), for example policies, procedures or training modules, instantly. Furthermore, it allows entities without fixed facilities, for example the Centers for Disease Control (CDC), to publish (FIG. 6), and route (FIG. 8), emergency procedures, guidelines or training modules and have those procedures, guidelines or training modules instantly implemented at facilities on the network.

Figure 1:
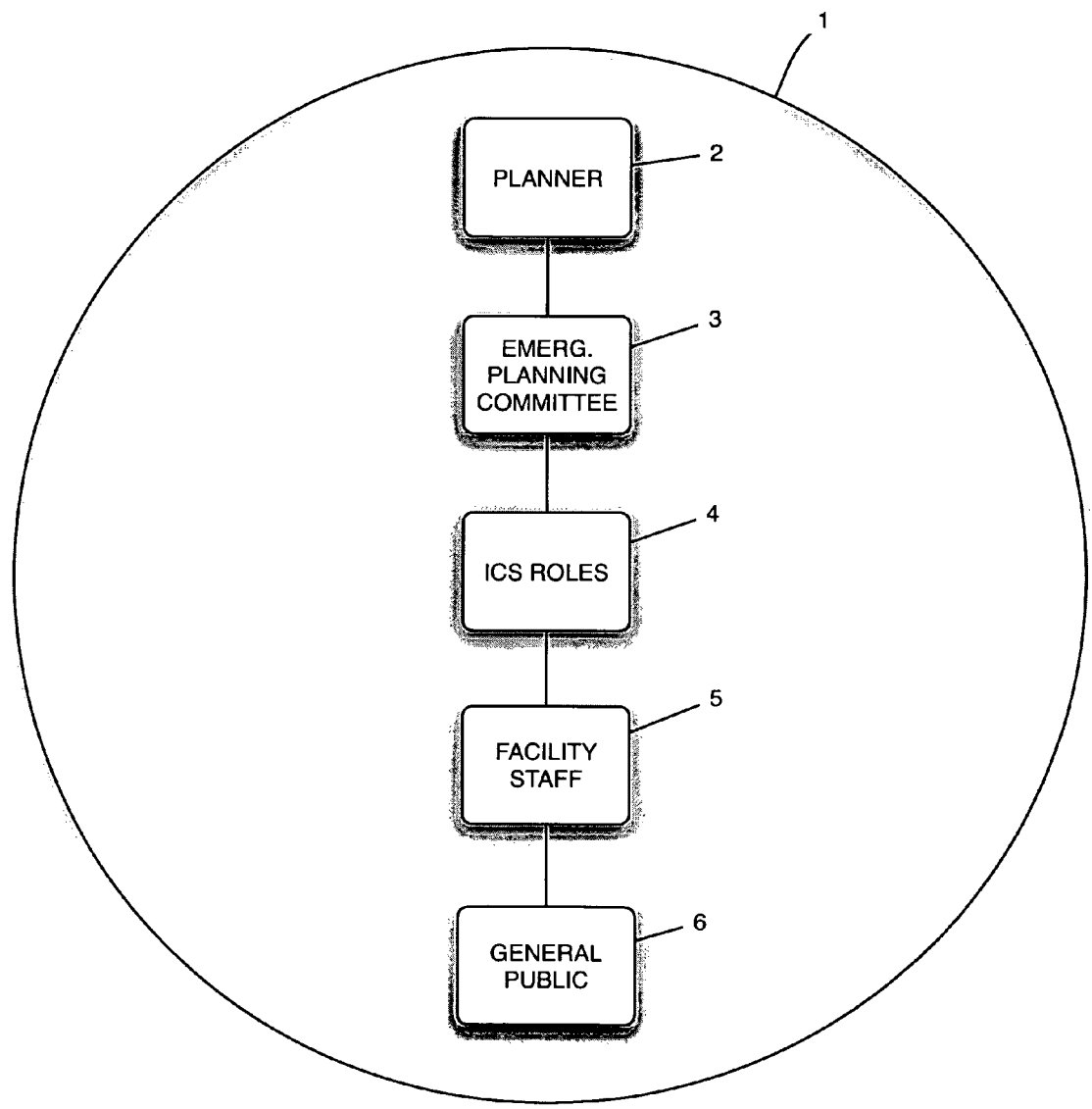
FIG. 1.

Permissions to the emergency plan and its component parts are organized into levels. The emergency planner (2) is the person or persons whose primary responsibility is creating, updating and maintaining the emergency plan for the facility or network of facilities. This person has full access to his or her facilities emergency plans, procedures, resources and training data. Secondary in permissions to the emergency planner is the emergency planning committee (3). This is a person or group of persons whose responsibility is to participate in the planning of the facility through review and commentary on the emergency plan. Emergency planning committee members may be blocked from seeing the entire plan, they only need to see what they need to facilitate emergency planning—the particular policies, procedures, resources etc that they have been asked to comment on. The third level of permission is the Incident Command System (ICS) role (4). Each role in a facilities ICS organizational chart may view the plan, especially his or her part in the plan, but will not have permission to change, edit, or add to the plan. The next level of permission is that of the facility employee (5). This person does not have a specific role in the ICS, but still must know, and be familiar with, general emergency plan policies of the facility. This person only has access to the non-ICS portions of the plan that pertain to employees or residents of a particular facility. The final level of permission is that of the general public who have a need for access to a facilities emergency plan (6). This level of permission is read-only and is limited to information designated as for public use. All of these levels of permission taken together constitute a facilities planning and training permissions levels (1).

Figure 2:
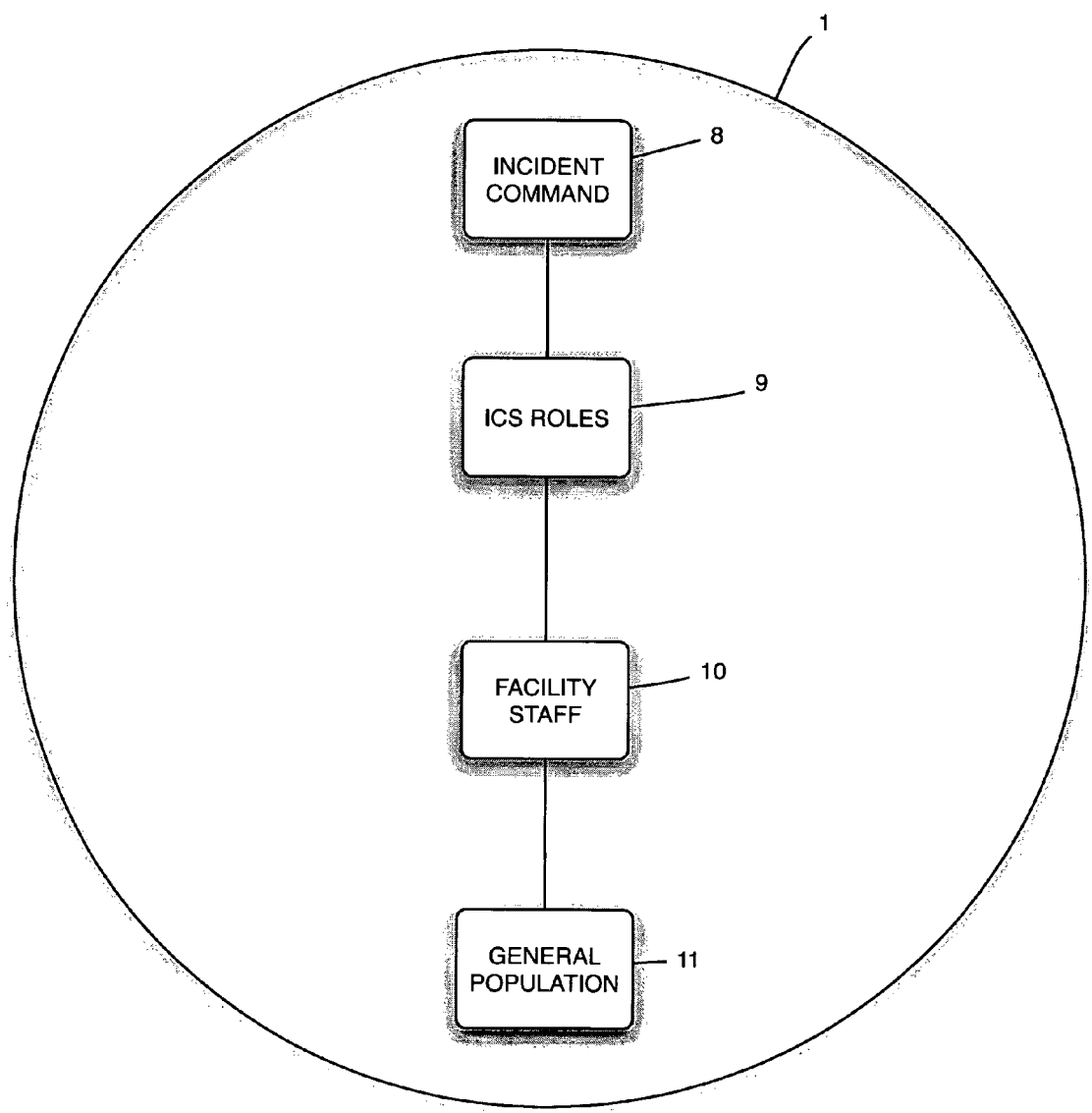

FIG. 2:

During a Drill or an Actual event, the emergency plan will be accessed using the permissions shown in FIG. 2. Every emergency response is judged as to its severity, if the emergency warrants the Incident Command System will be activated. The top level of permissions in the Incident Command System are given to the Incident Commander (8). This allows him or her to change the status of the emergency response, direct the facilities response to the given emergency, and to change the roles required in the emergency response as needed. The ICS roles he or she activates (9) have permissions to read the emergency plan, with focus on their part of the emergency plan—meaning that their procedures are displayed upon login to facilitate the emergency response. The remaining permissions, that of the facility staff (10) and the general population (11) are give further access to the emergency plan, at levels equal to their participation in the emergency response.

FIG. 3:

A network of facilities may interchange elements of the emergency plan during planning and training phases. The emergency planner (13) at facility 1 (12) may exchange (13a) policies, data, or communications with his or her counterparts (18) and (23) at facilities (17) and (22). The emergency planning committee associated to facility 1 (12) may participate (14a, 14b) on the planning committees of other facilities (17) and (22) by providing review, commentary and feedback on elements of any given emergency plan or component of an emergency plan. Each Facility (12,17,22) may have a different ICS organization (15,20,25) and facility staff roles in the emergency response planning and training (16,21,26).

FIG. 4:

During an emergency response drill or emergency event, Incident Commanders (28, 32) at separate facilities (27,31) may exchange information (28a) in the form of plan components, event log messages, communications, and data file interchange. Activated ICS roles at separate facilities may exchange communications and data, log message events with their counterparts at other facilities. This would be the case in a multi-facility response during a drill or actual event.

FIG. 5:

Facilities, constituting an emergency planner, an emergency planning committee, ICS roles, facility employees and general public associated with a particular facility, may form a network of facilities (39,40,41). Each of these facilities may exchange emergency plan components with the other (39a, 40a,41a).

Figure 6:
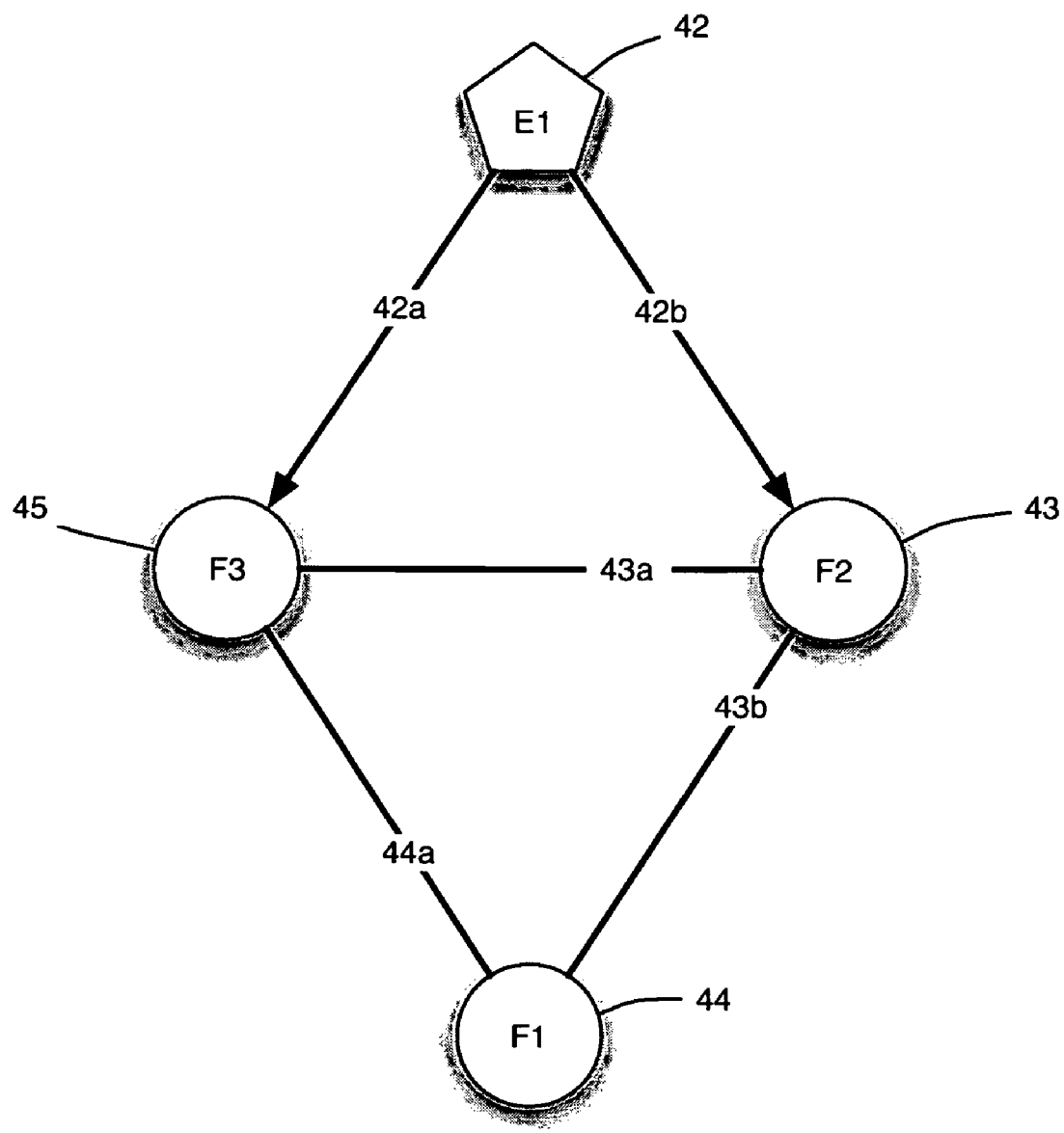

FIG. 6:

FIG. 6 shows an entity (42), such as the CDC, publishing information (42a,42b) such as a specific health guideline, to a network of facilities (43, 45). members of the network may elect not to recieve guidelines (44), or may not have plans that are pertinent to the information being broadcast. Since all facilities are on the network, they may then exchange the information with each other on an as-needed basis (43a, 43b, 44a).

FIG. 7:

Facilities on a network (49, 47, 48), who regularly exchange information (47a, 48a, 49a) may also publish information to an entity (46). A sample use is in a public health early warning system where facilities are on the lookout for specific indicators, and are instructed to report incidents to an entity who correlates the data (49a) into a composite picture.

FIG. 8:

An entity E1 (50) may also route data (50a) received from facility F4 (51) to (50b,50c) a network of facilities F1, F2, F3 (54, 52, 53). These facilities may then share the information (52a,53a,54a).

FIG. 9:

Entities may be associated with each other, creating a network of entities E1, E2, E3 (55,56,57). These may share emergency plan information (57a, 55a, 55b), receive reporting information (61a), as well as route that information to networks of facilities (57b, 57c).

FIG. 10:

The Standard Emergency Plan Format consists of the Hazard Vulnerability Analysis (HVA) (62), Facility specific policies (63), Procedures (64), Emergency resources that are available to the facility (65), and a described ICS such as the Hospital Incident Command System (HEICS).

FIG. 11:

The structure of the platform at each facility or entity consists of the following areas: A mapping and geospatial information system (GIS) area (67), the planning area (68), an area which presents the entire community (69) of emergency planners for information interchange, an area for reference (70) where emergency planners may look up information using simple and advanced search techniques such as keyword or facility type, and area where facilities or entities may publish information to the community (71), a response area

(72) where those with ICS roles may set or view the current response phase of the emergency plan, and view information pertaining to their particular role in the response to an emergency, or in a drill for a particular emergency. A reporting area (72a) allows the emergency planner and select ICS roles to create and view reports pertaining to the emergency plan. A Training area is provided where the emergency planner creates, maintains and updates drills, training materials and their component parts.

Figure 12:
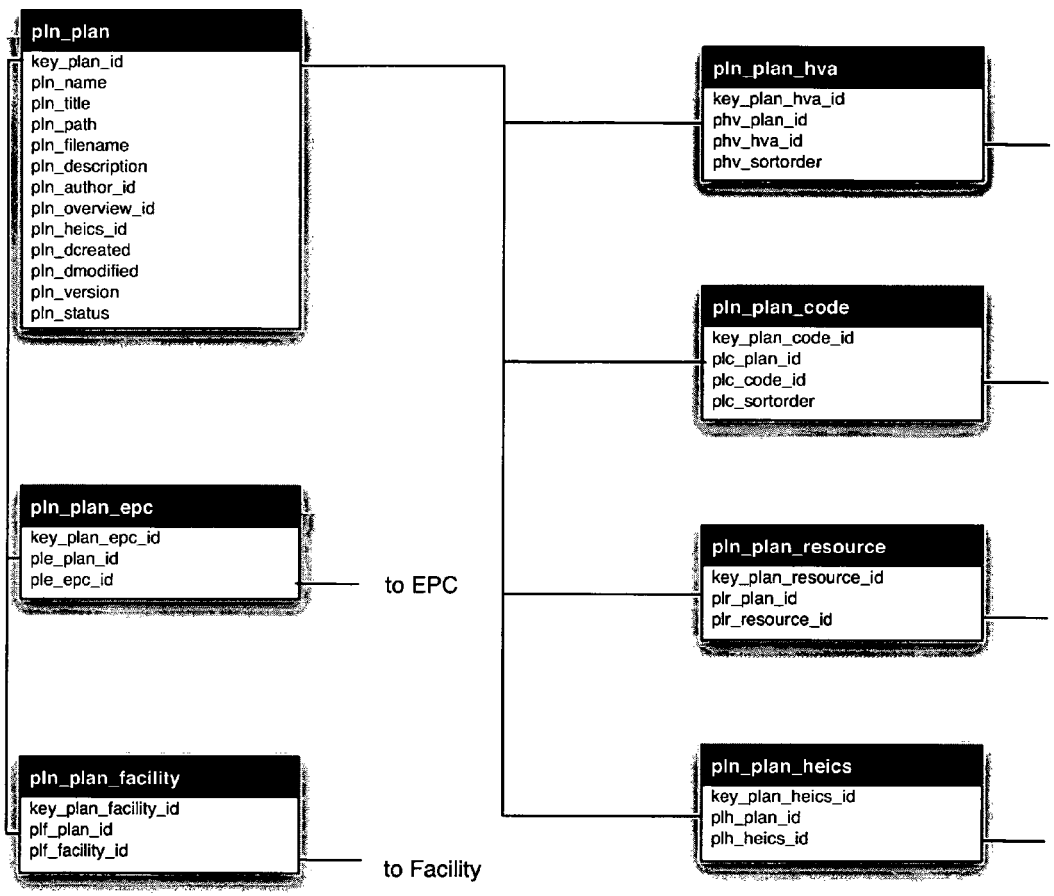

FIG. 12: Database tables—Plan Table Structure

Figure 13:
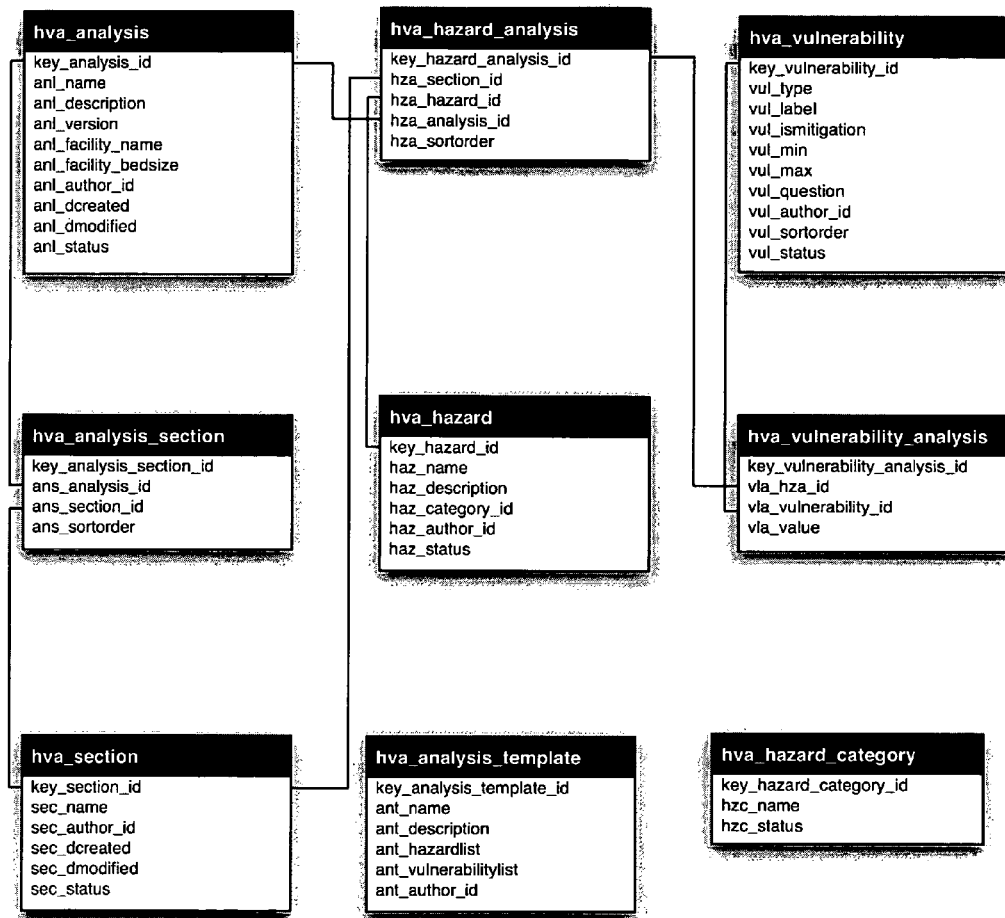

FIG. 13: Database tables—Hazard Vulnerability Analysis Table Structure

Figure 14:
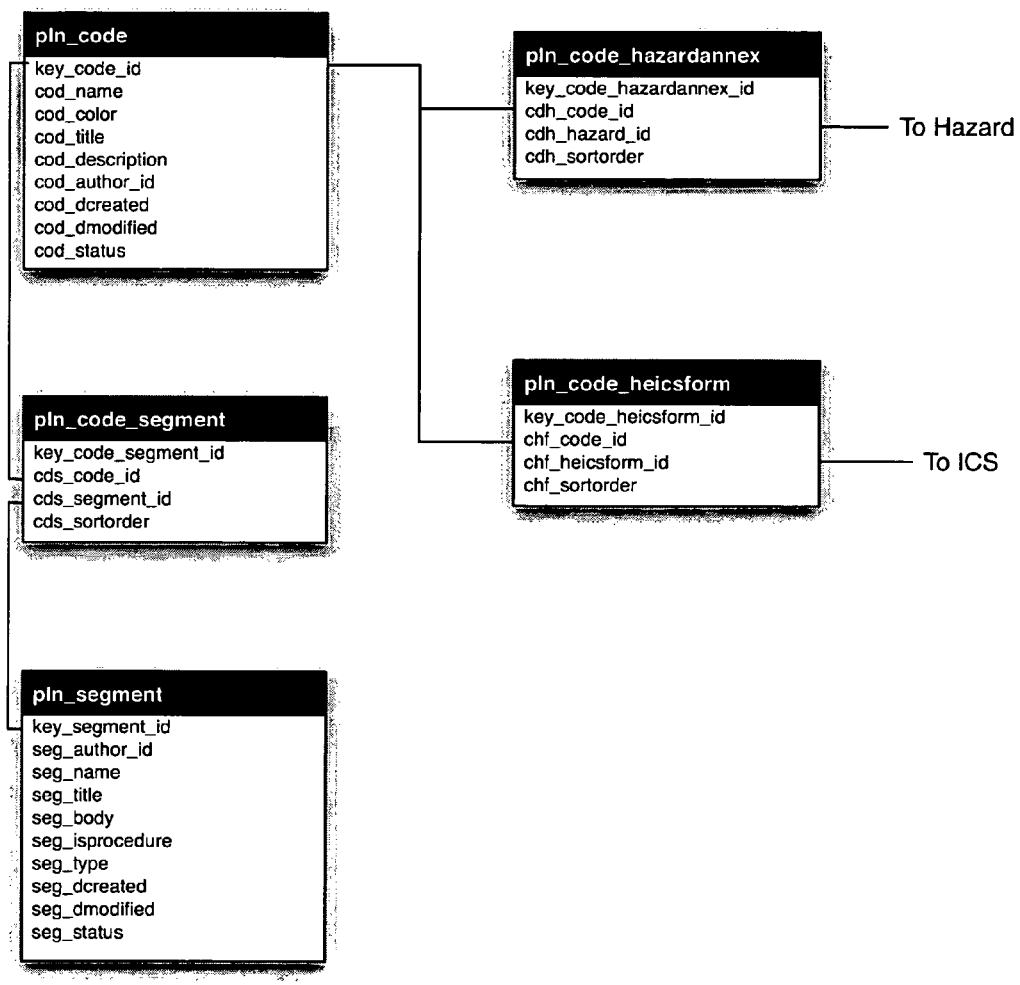

FIG. 14: Database tables—Policy Table Structure

Figure 15:
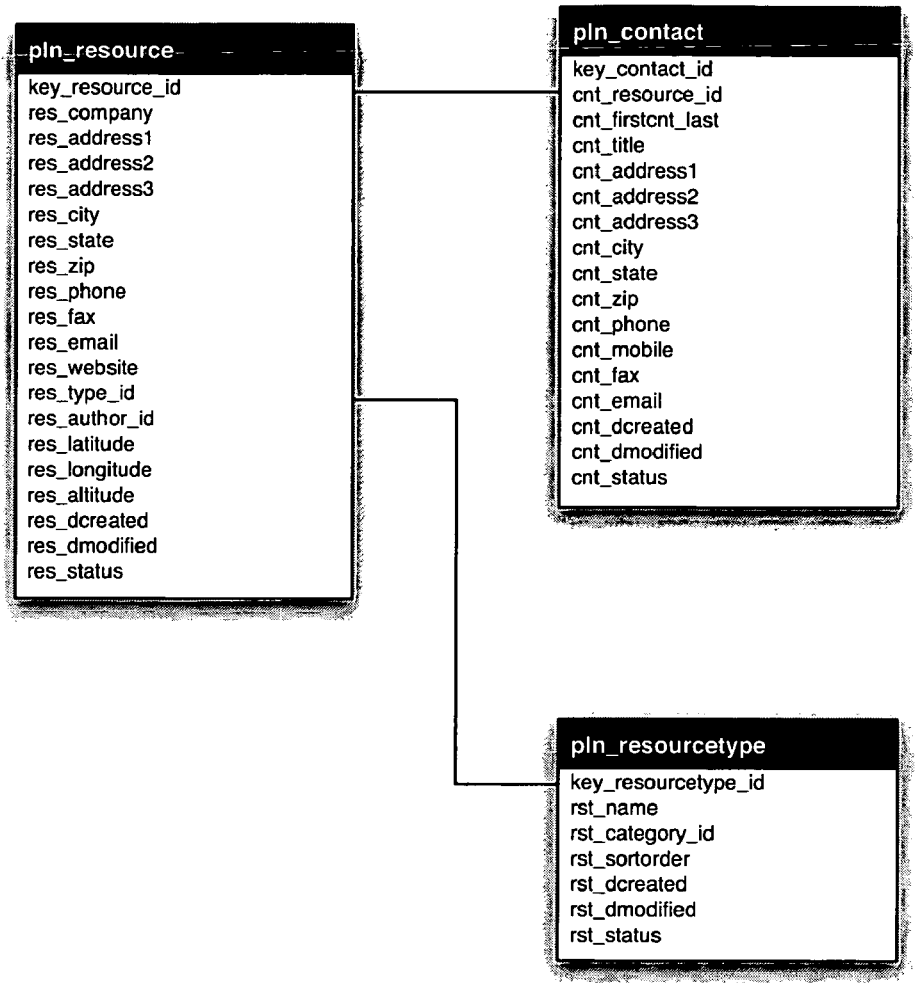

FIG. 15: Database tables—Resource Table Structure

Figure 16:
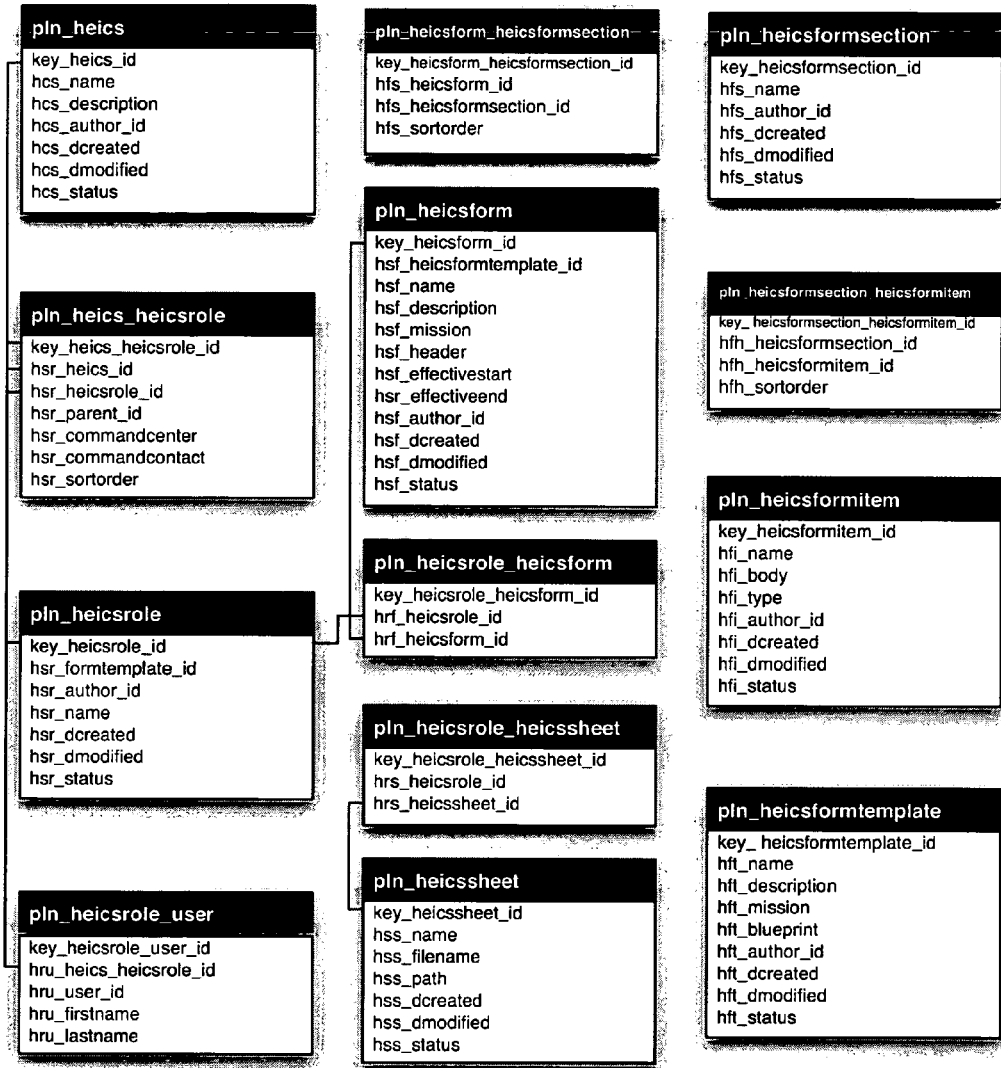

FIG. 16: Database tables—Incident Command System Table Structure

Figure 17:
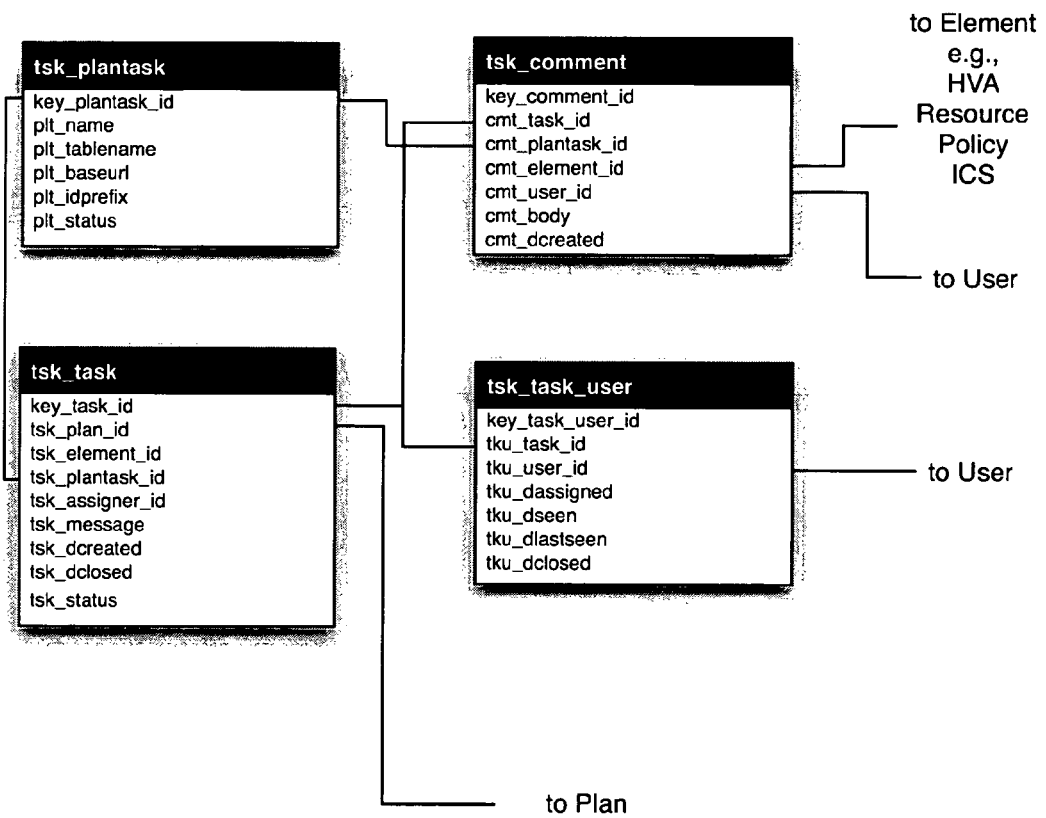

FIG. 17: Database tables—Emergency Planning Committee Task table structure

Figure 18:
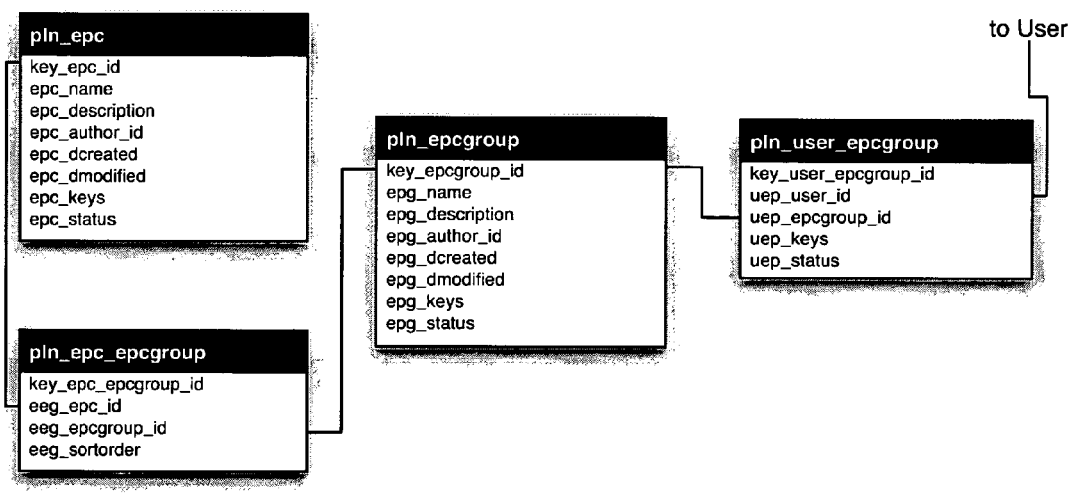

FIG. 18: Database tables—Emergency Planning Committee table structure

Figure 19:
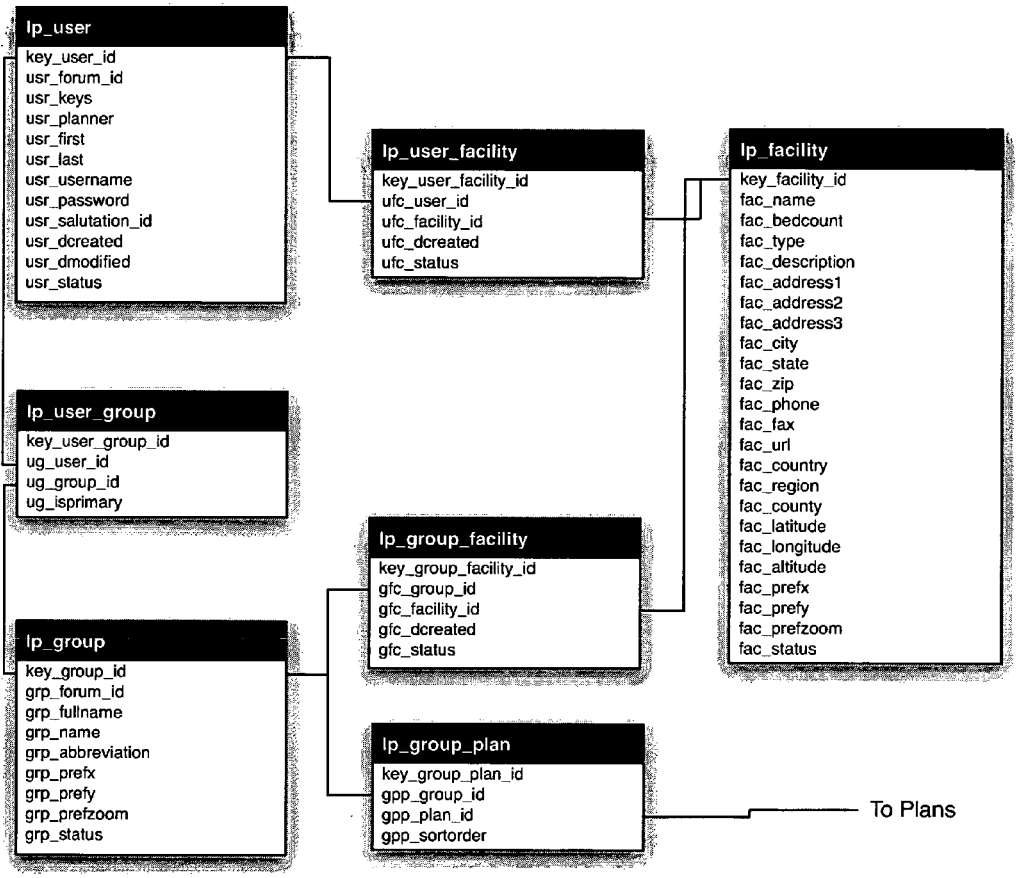

FIG. 19: Database tables—User Facility table structure

FIGS. 20-64: Scenario Screenshots (see scenario section)

Figure 65:
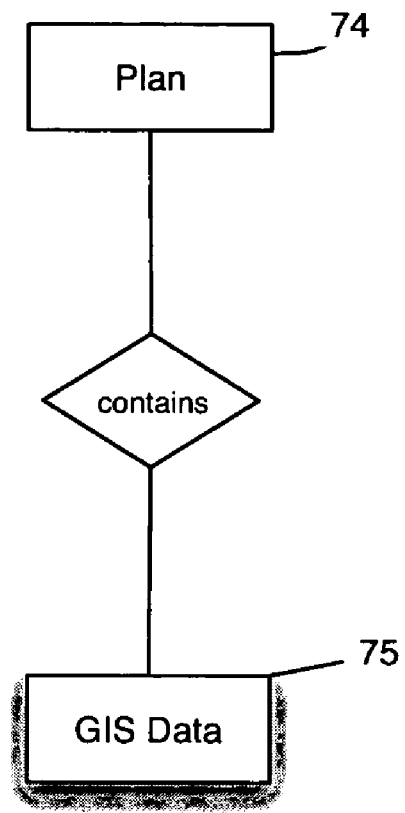

FIG. 65: Plan ERD—Plan (74) contains GIS Data information (75)

Figure 66:
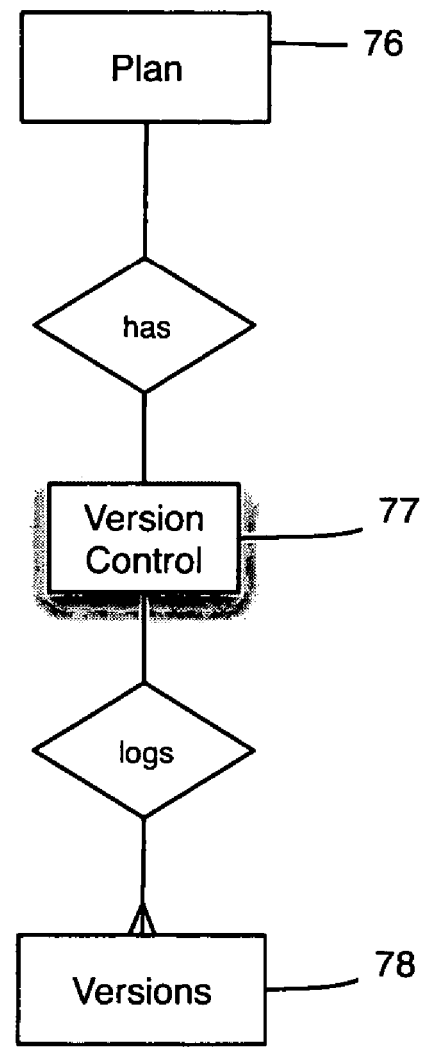

FIG. 66: Plan ERD—Plan (76) contains version log (77) of version records (78).

Figure 67:
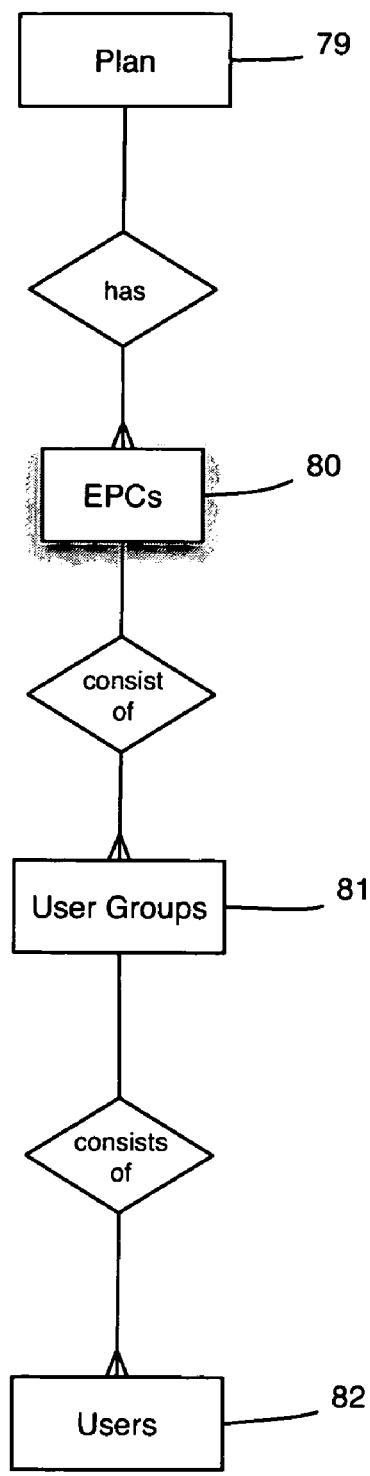

FIG. 67: Plan ERD—Plan (79) contains Emergency Planning Committees (80) which contain multiple user groups (81) each of which may contain multiple users (82).

Figure 68:
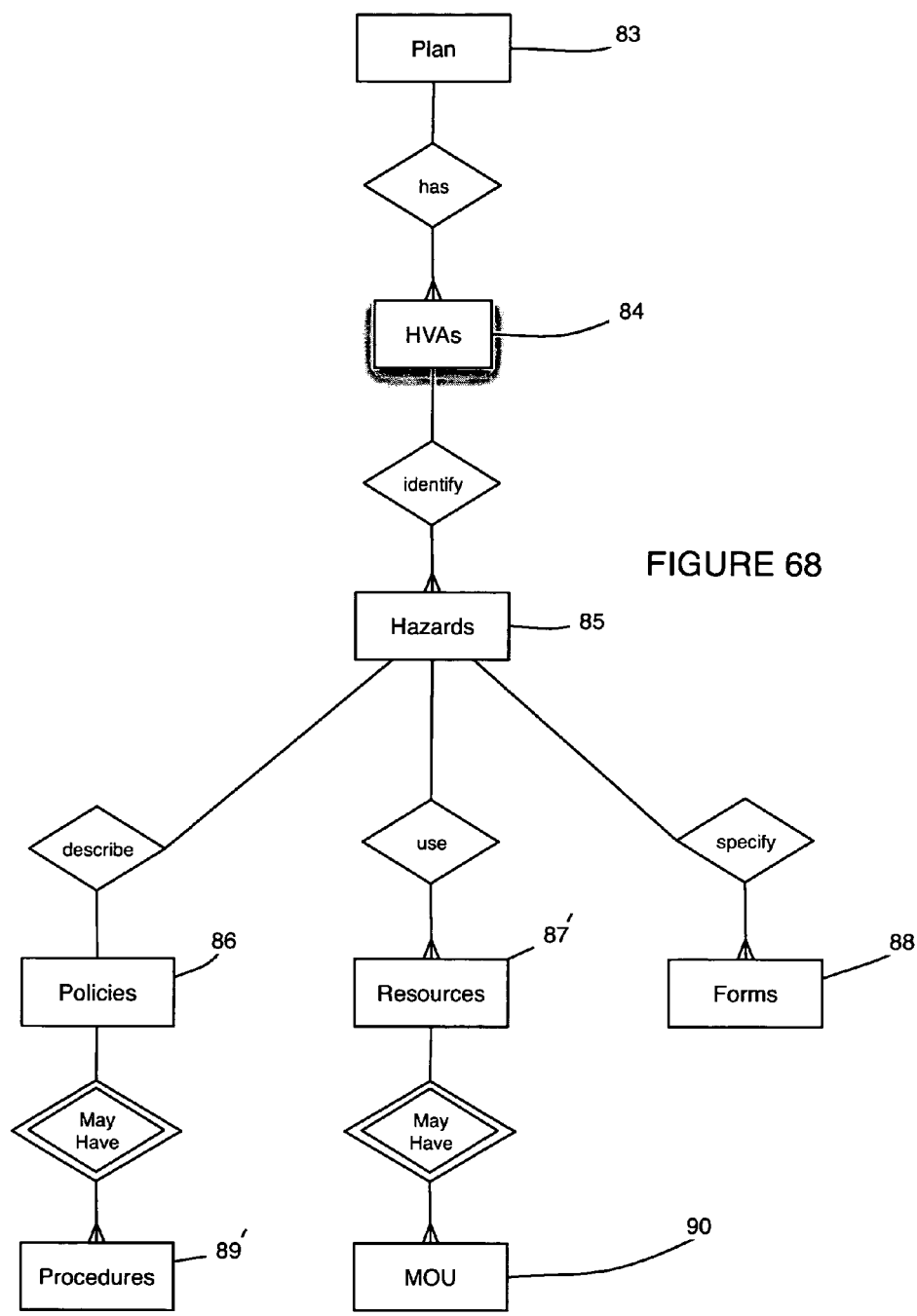

FIG. 68: Plan ERD—Plan (83) may contain multiple HVAs, each of which identify a multitude of Hazards (85), each of which may contain Policies (86), Resources (87) and Forms(88). Policies may have Procedures associated with them (89), and resources may have specific forms associated with them such as Memoranda of Undersatandings (MOU) (90).

Figure 69:
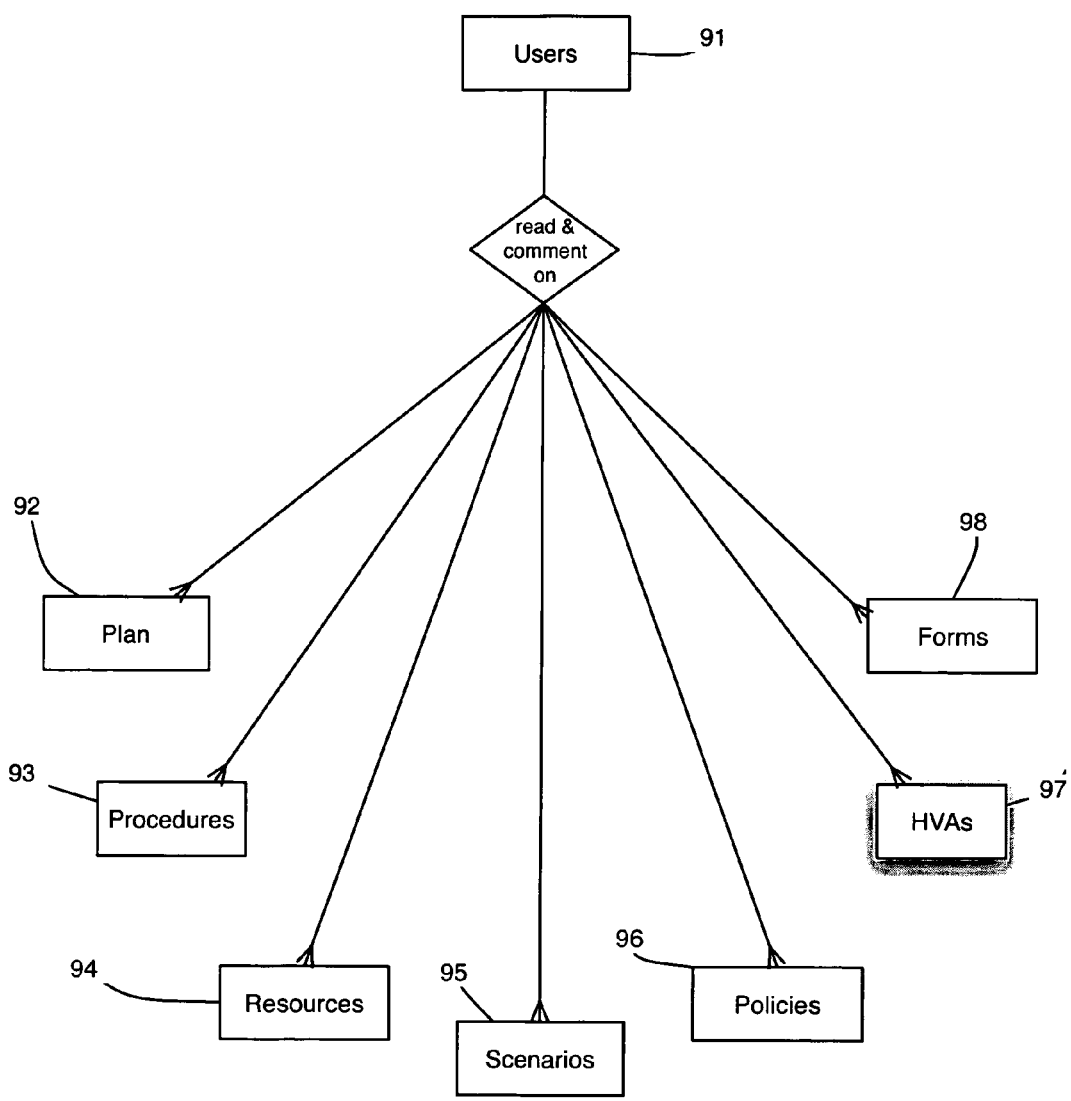

FIG. 69: Users have abilities according to their permission level. Users (91) may variously view, edit, or comment on: Plans(92), Procedures(93), resources(94), Training Scenarios (95), Policies (96), HVAs (97), and Forms (98).

Figure 70:
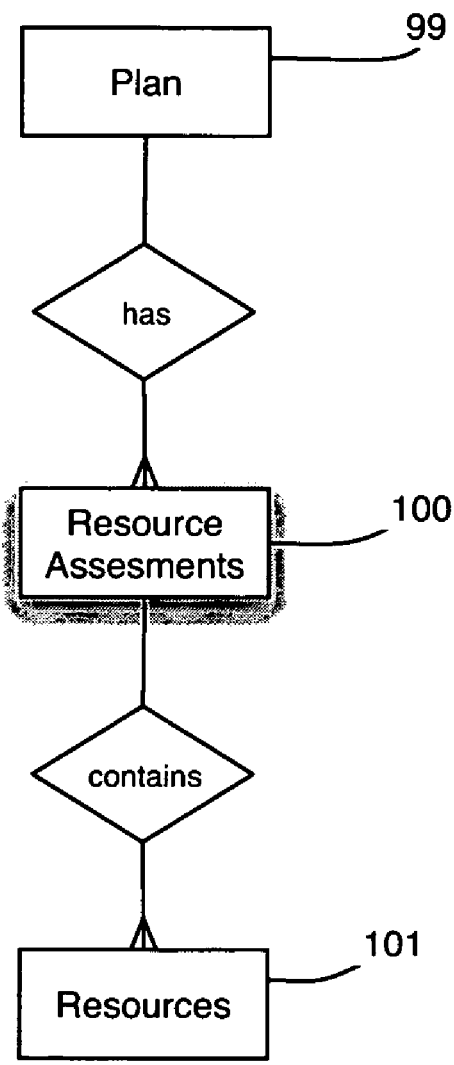

FIG. 70: The Plan (99) may contain one or many resource assessments (100), each of which may contain Resources (101).

Figure 71:
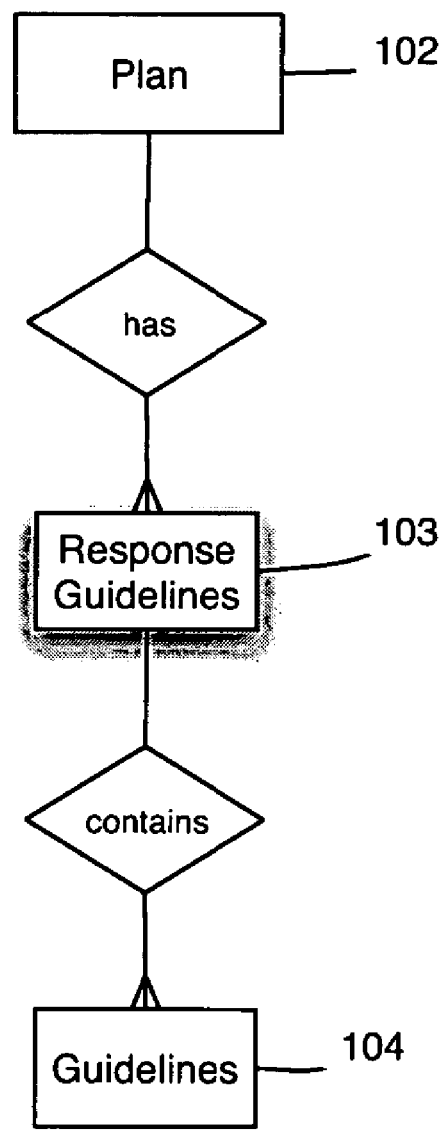

FIG. 71: The emergency plan (102) may contain one or many Response Guidelines (103) each of which may contain a single guideline (104).

Figure 72:
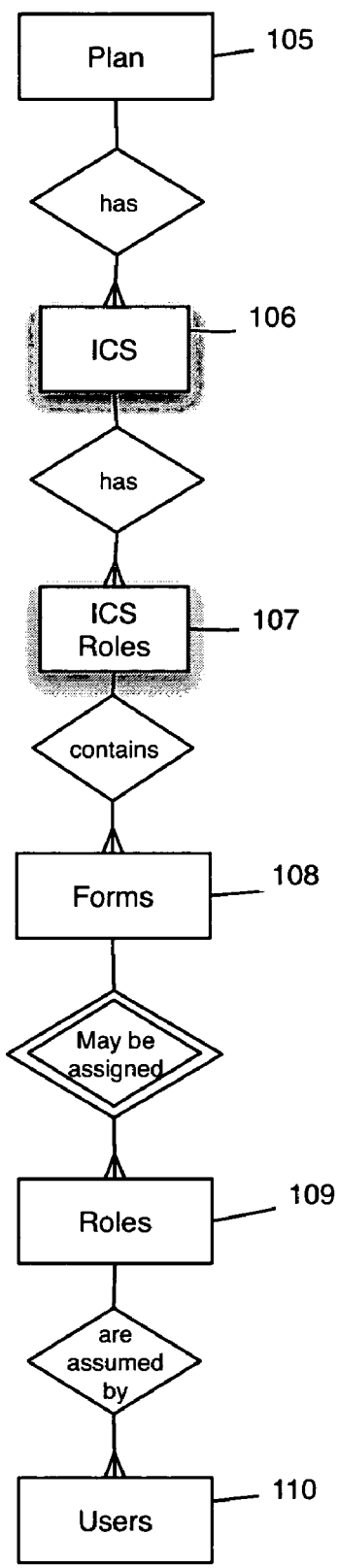

FIG. 72: The emergency plan (105) contains one or more organization charts representing an ICS, each of which designates ICS Roles (107), each role may contain references to specific forms (108) used by that role in the ICS. Roles (107,109) may be assigned to one or more Users (110).

Figure 73:
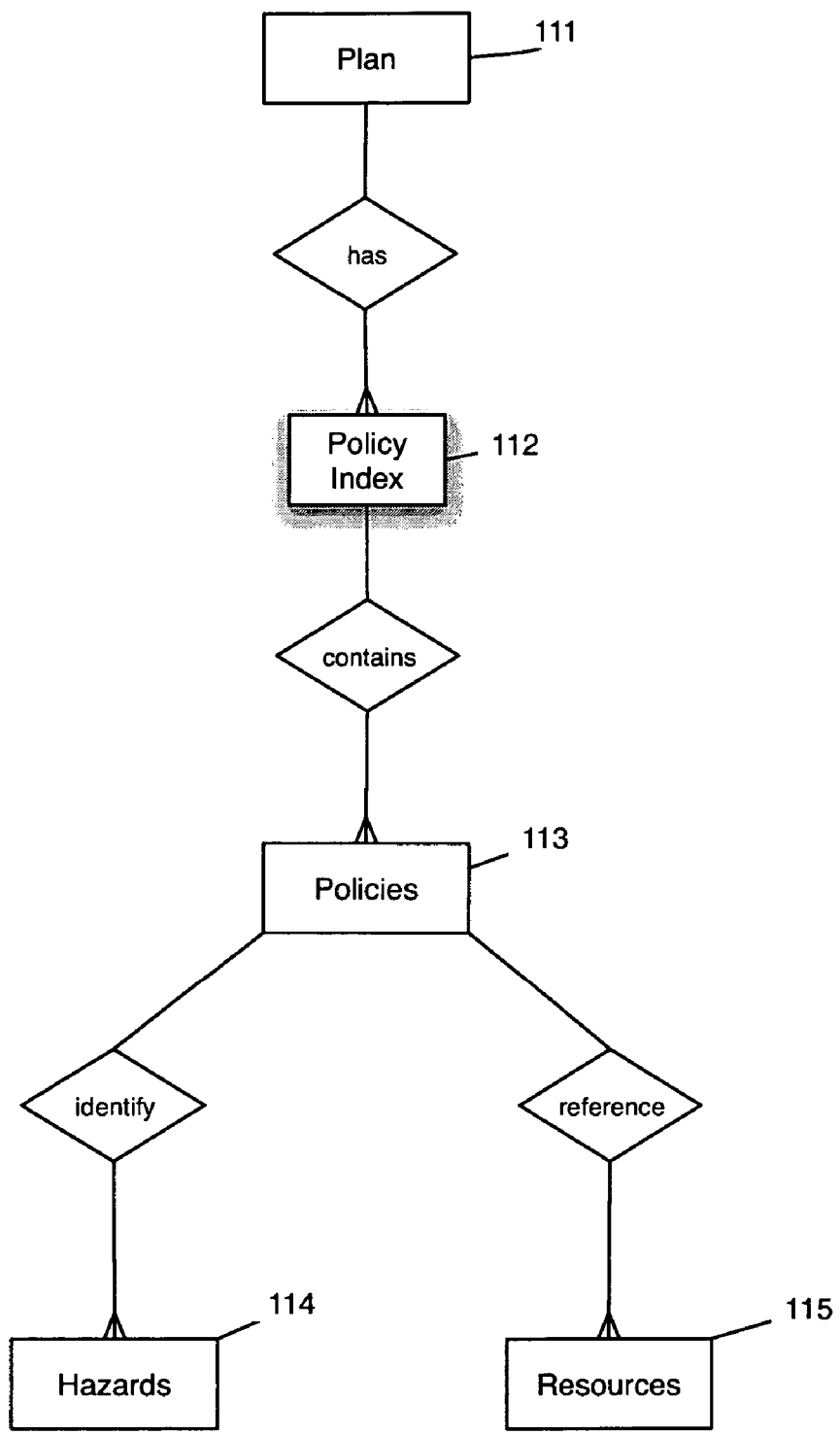

FIG. 73: The emergency plan (111) has a collection of policies, a poly index (112) which contains one or many pollicies (113), which may identify a related Hazard (114) and resources (115) that may be used in that policy.

Figure 74:
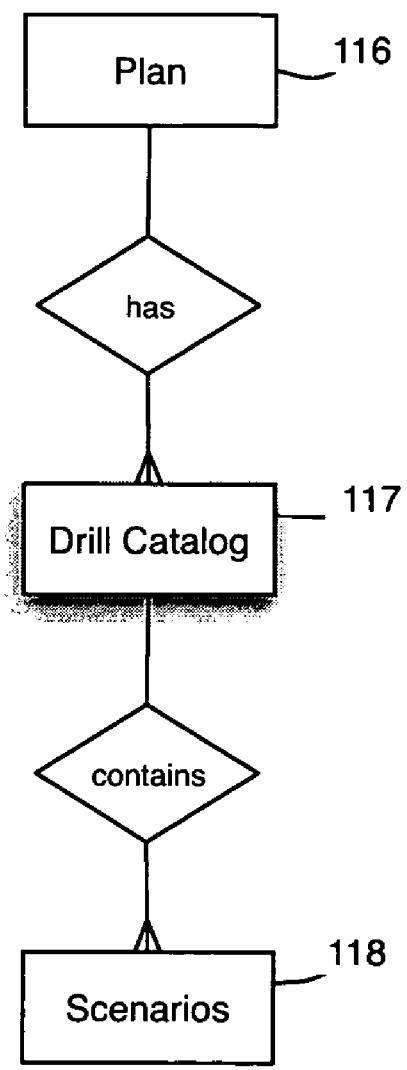

FIG. 74: The Emergency Plan has a collection of Drill catalogs (117) each of which contain one or many Drill Scenarios (118).

Figure 75:
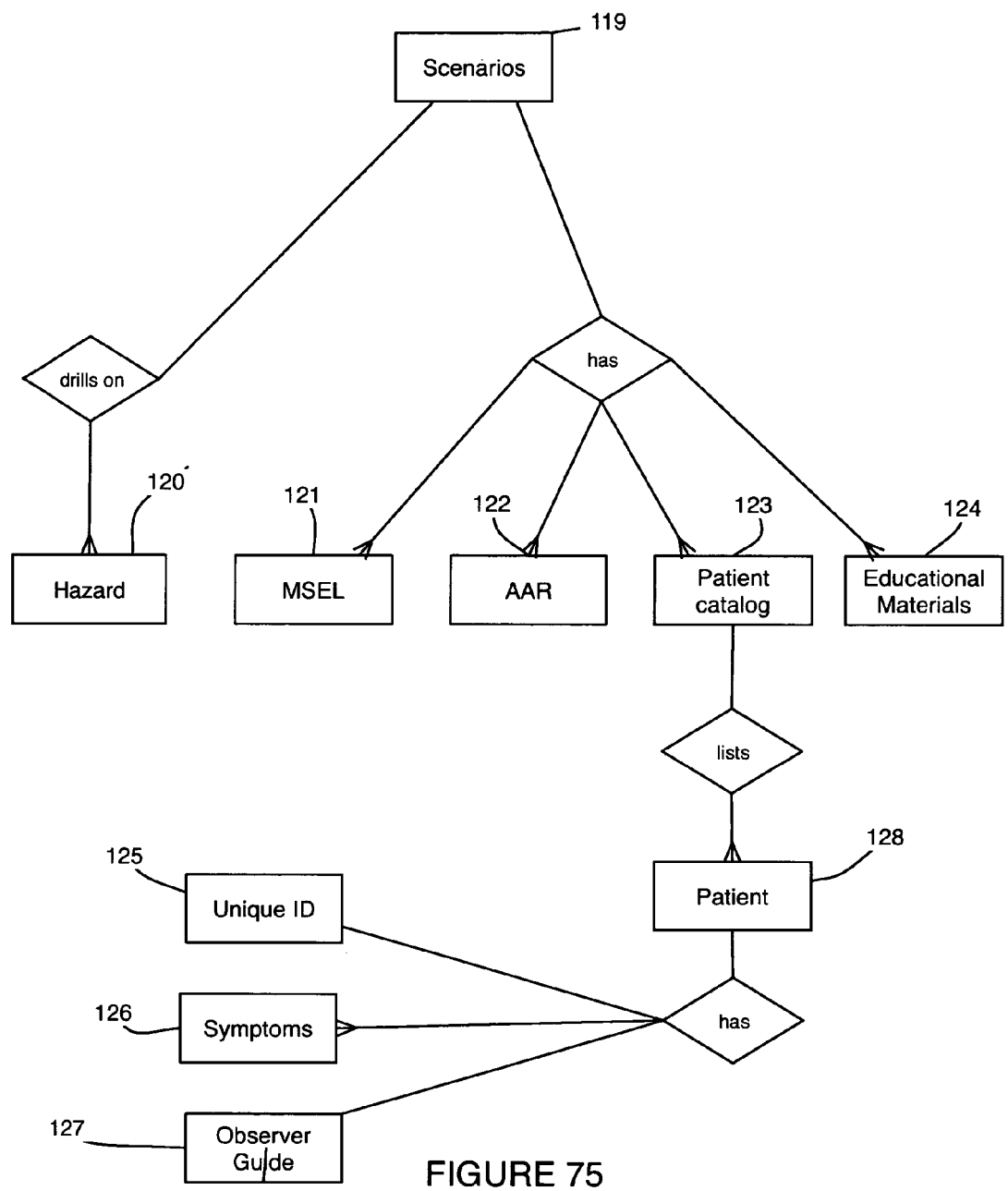

FIG. 75: Drill Scenarios may be associated to a specific hazard or hazards (120), and may contain one or many; Master Sequence of Events Lists (121), After Action Reports (122), Patient Catalogs(123) and Educational Materials (124). The Patient Catalog lists multiple patient cards (128) each with an ID (125), a list of symptoms (126) and an observer guide (127).

Figure 76:
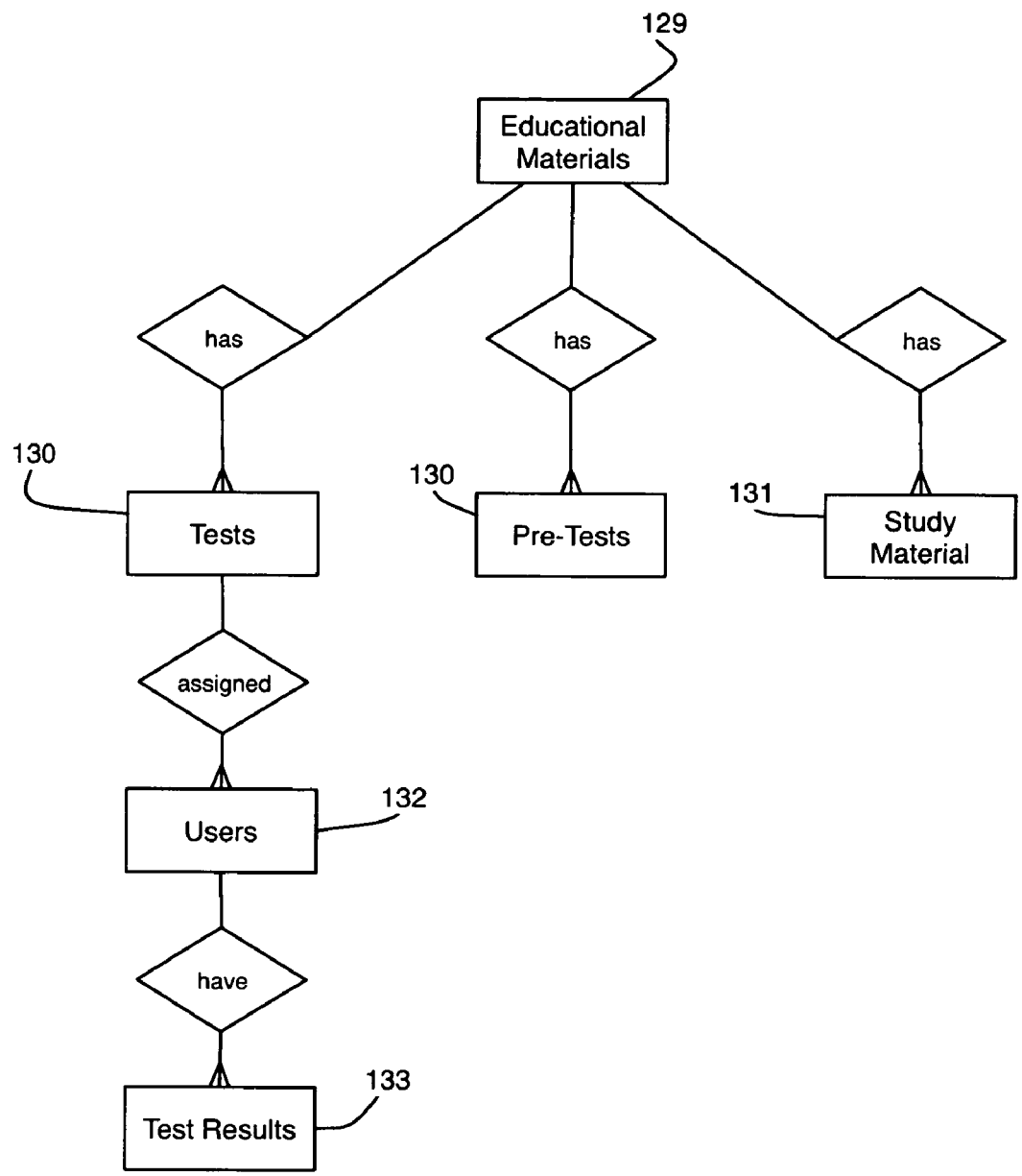

FIG. 76: Educational Materials (129) consist of Tests (130), pre-tests (130) and Study material (131). Tests have associated Users (132) and Test Results (133).

DETAILED DESCRIPTION OF THE INVENTION

I. Overview

The Networked Emergency Management System is preferably realized as a web application located on one or more servers and is accessed using standard web protocols (HTTP, HTTPS) from an internet web browser such as Microsoft Internet Explorer, Mozilla Firefox, or Apple Safari, web enabled personal digital assistants (PDAs), or web-enabled wireless telephones.

The present invention allows the user, through a secure login, to access the platform according to permission level, from emergency planner (FIGS. 1-2) to member of the general public (FIGS. 1-6). What the user sees, and what they are allowed to do with the present invention, relies on the amount of permissions they have been granted on the system. The Emergency Planner has the highest level of permissions and will be presented with the tools needed to create, update and maintain an emergency management plan for a facility of network of facilities.

Figure 10:
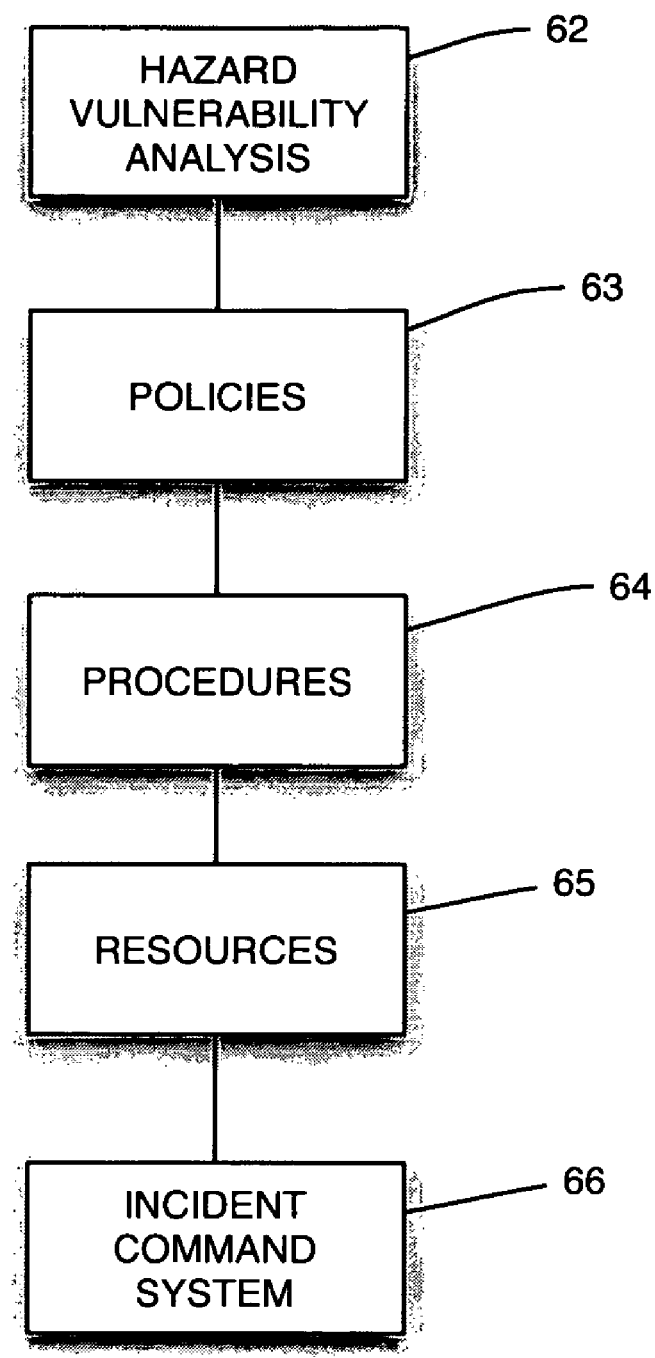
Figure 24:
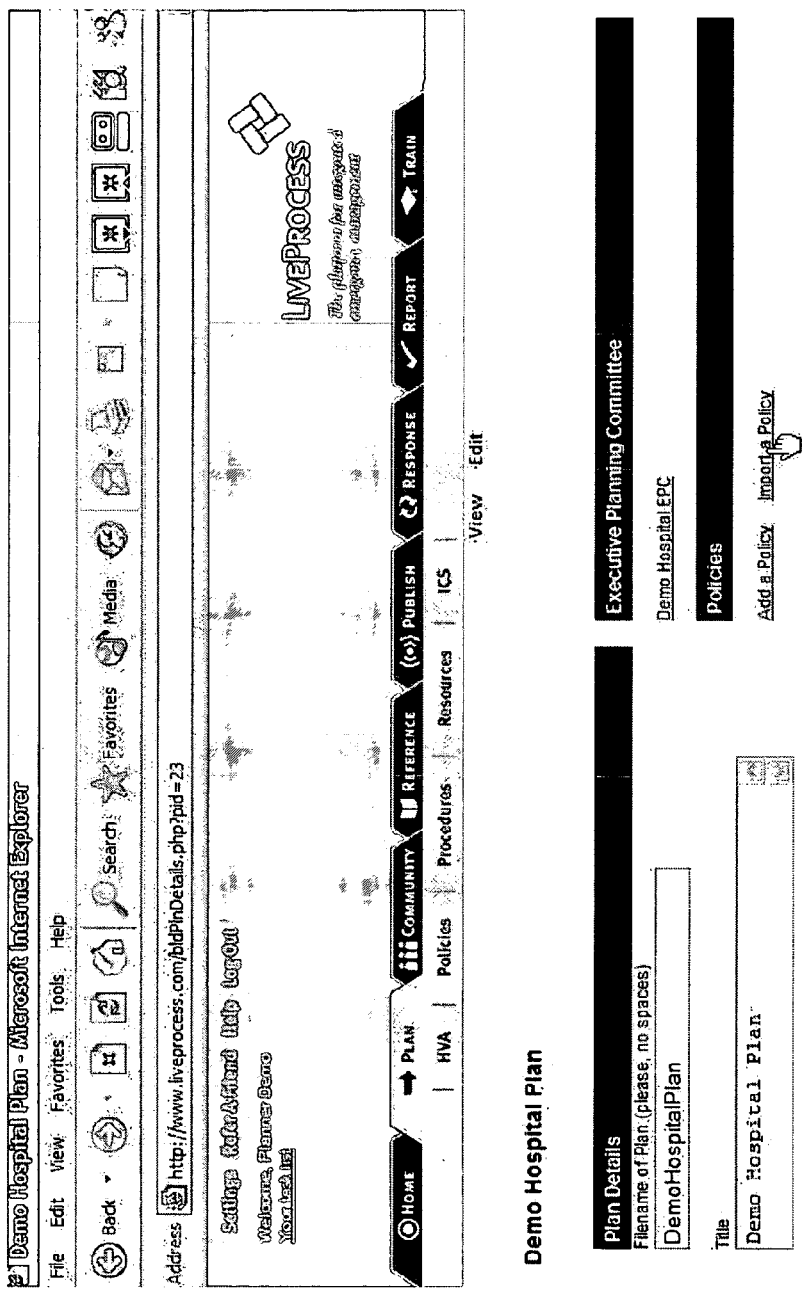
Figure 25:
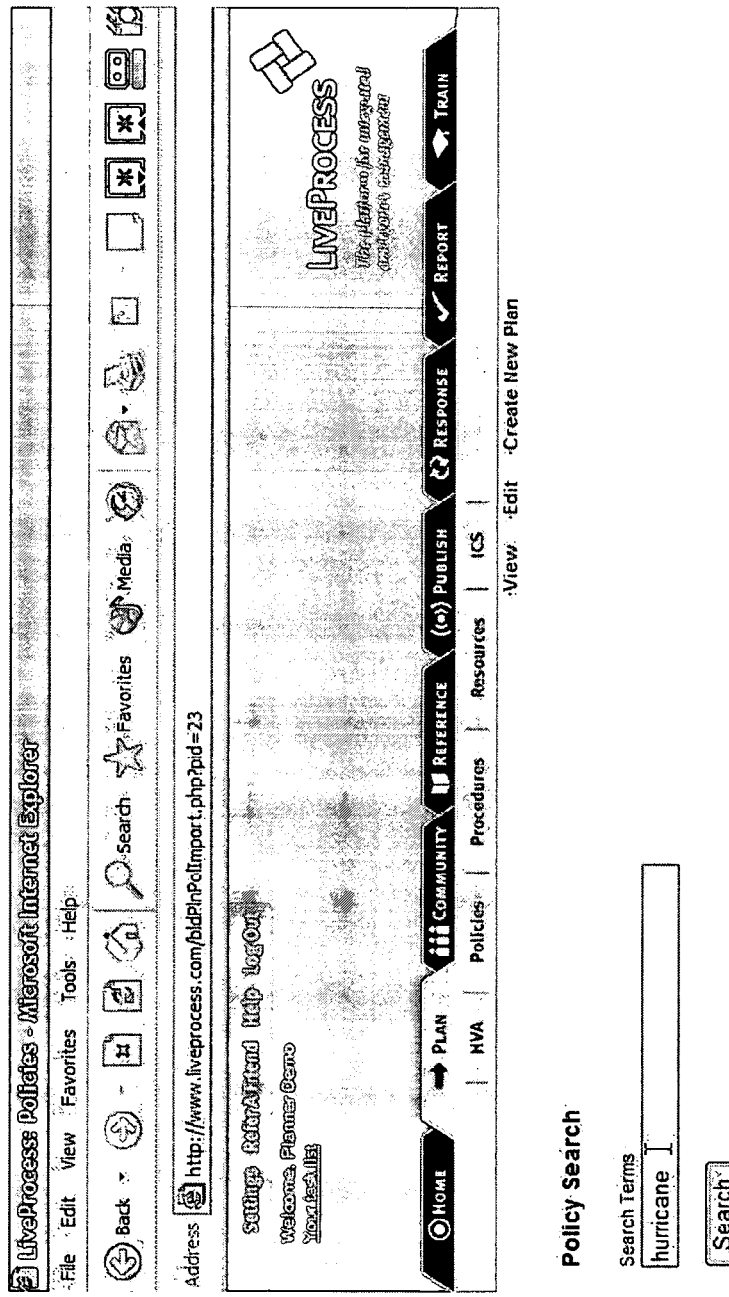
Figure 26:
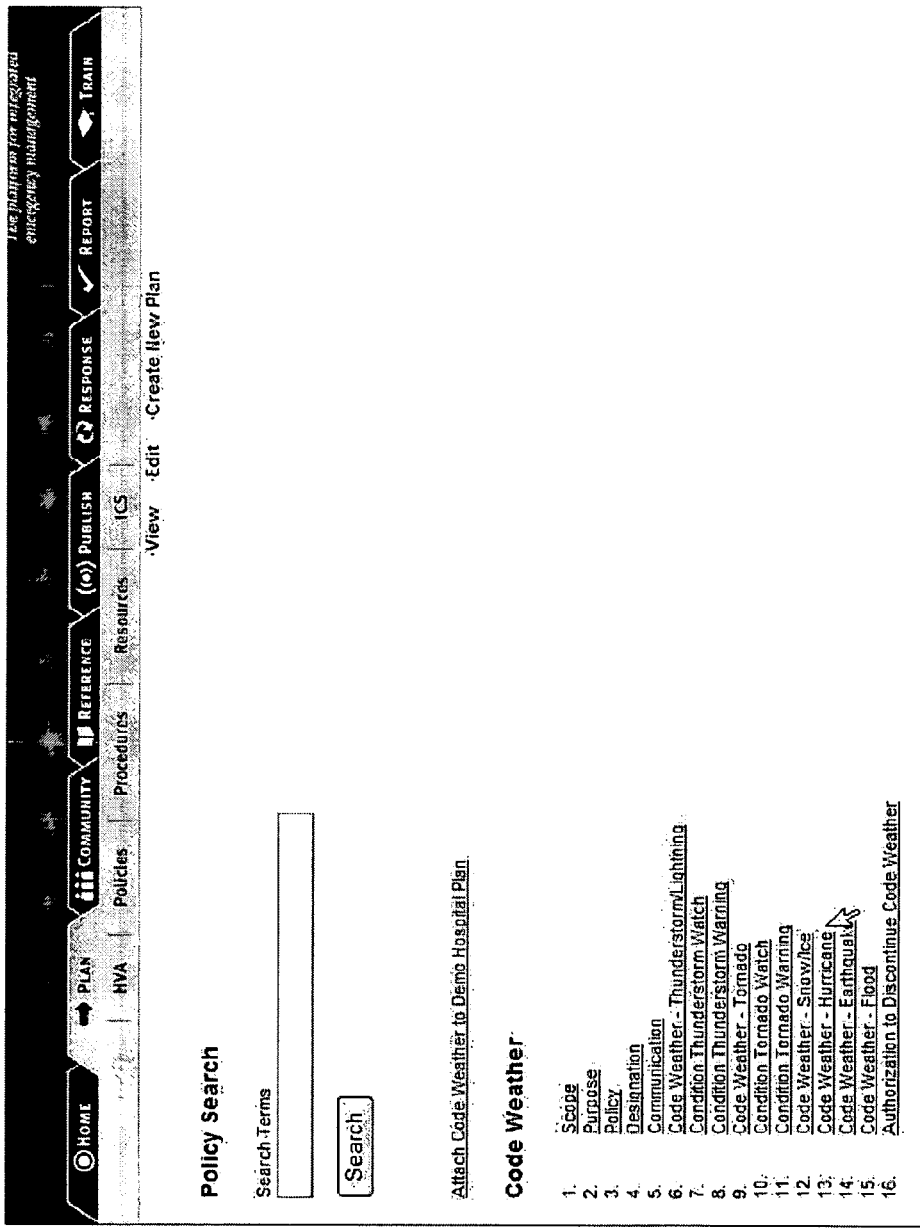

Emergency Planners use the system to exchange emergency management information centered around a standardized emergency plan and each of the plans component parts; the Hazard Vulnerability Analysis (HVA), Policies, Procedures, Resources and a detailed Incident Command System. (FIG. 10) For example, the emergency planner may wish to import a policy from a facility that has more experience with a particular kind of hazard. Using the present invention, they may do so instantly (FIGS. 24-26).

The HVA (FIGS. 10-62) is a standard tool of the emergency planner. The advantage of the present invention's implementation of the HVA is the standardization of the format used in calculation of risk, allowing all emergency planners to use the same basis of risk. It also standardizes the hazards risk is calculated for. The function used to calculate risk is $$r = (p/\text{maxtotal}\_p) * ((\text{sum\_impacts})/\text{maxtotal\_impacts}) * 100$$

where
r is risk in terms of a percentage
p is likelihood
maxtotal_p is sum of maximum possible likelihoods
sum_impacts is a summation of all impact scores
maxtotal_impacts is a sum of the maximum possible impacts This function may be seen in use in the HVA (FIG. 39) In addition, the present invention provides an optional simple method of entering information into the HVA, intended to simplify use by the new or inexperienced planner. (FIG. 38). This method asks the planner a series of questions, the answers to which inform the results of the HVA. When the questionnaire is complete, the user is shown the completed HVA. (FIG. 37).

Policies (FIG. 10-63) in the framework of the present invention constitute all of the textual material of the plan with the present invention and provide two important advantages, namely, the ability to interchange policies between plans with a single click (FIG. 24), and the ability to label a segment of the Policy as a Procedure, allowing it to be listed separately with other policies for rapid review during an emergency drill or actual response.

Procedures (FIGS. 10-64) are sections of policies that directly correspond with steps or instructions that must be taken in an emergency plan. An example of a procedure is "How to don protective gear in a hazardous materials response". Such instructions would be labeled a Procedure in the present invention and added to the facilities emergency management plan. Since these instructions have been labeled, a procedure allows them to be listed separately in the Procedures area, and may be read with a single click.

Resources in the present invention address the need to collect records of all emergency management resources available to the emergency plan in the event of an emergency, a drill, or during planning or recovery phase to estimate the financial expense of an emergency. These resources list the type of resource (fire department, pharmaceutical supplies, or bed availability), details on the resource, number, contact information, and the geospatial location of those resources so that they may be plotted on a map (FIG. 52).

Figure 57:
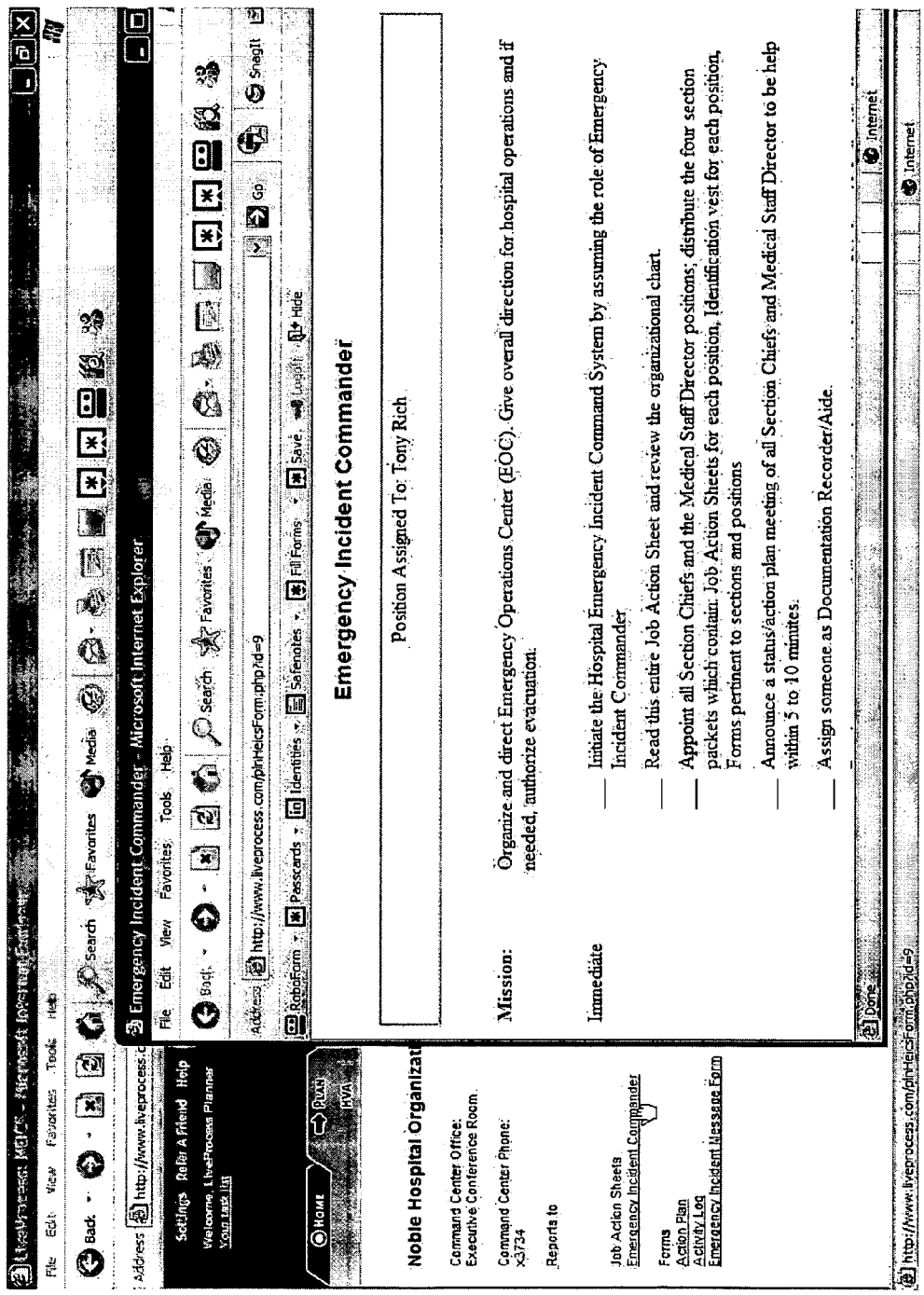

The Incident Command System is an organizational chart specifically for use in emergency management. It lists all roles in the emergency response, their titles and hierarchical relationship to each other. (FIG. 54) The advantage that the present invention provides, besides providing all relevant emergency information in one place in the form of HVA, policies, procedures, resources and ICS, is that each role of the ICS may be edited. This allows the emergency planner to edit any chosen role in the ICS, and change the specifics of their role, such as the title of that role, its mission or any of its responsibilities or forms that are required by the role. (FIG. 57).

The Emergency Planner has access to all areas of the system: Home/Map, Plan, Community, Reference, Publish, response, Report, and Train. The Home mapping area is used by the planner to visualize the status of the network and to determine the geospatial importance of the facility's location, the location of potential hazards, the location of existing or potential physical features, and geospatial historical data, such as flood, hurricane or earthquake risk. (FIG. 53, FIG. 52)

Figure 22:
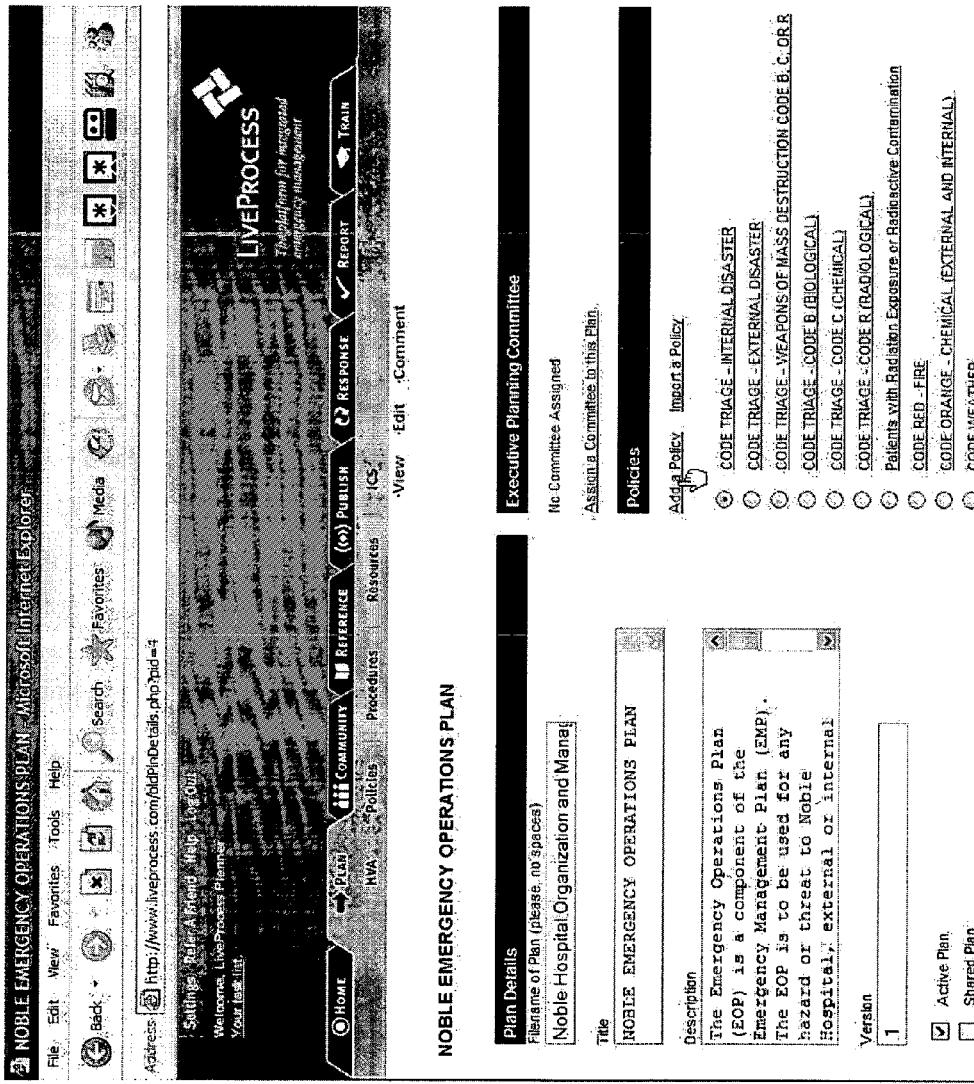

The Plan area offers the emergency planner access to all components of the emergency plan via a tabbed graphic user interface. (FIG. 22). Each area of the plan listed in FIG. 10 may be accessed.

Emergency Planners may communicate with each other using the common interface of a bulletin board in the Community area. (FIG. 60) This area is available only to users with emergency planner permissions, and is organized into emergency management related forums such as "Disasters & Events" and "Public Health". Forums may be used to post messages between emergency planner, facilitating cooperation between organizations.

Figure 61:
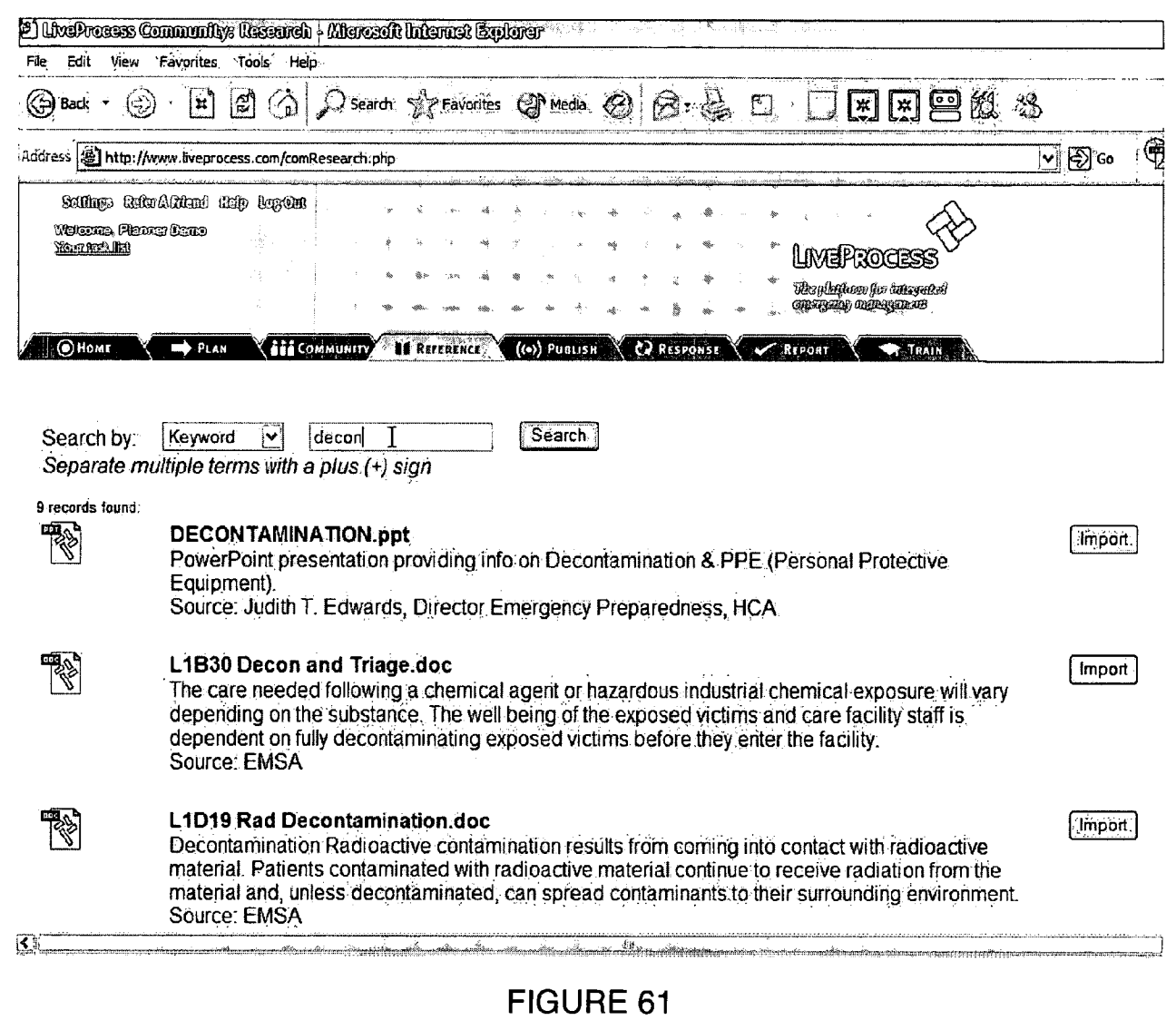
Figure 62:
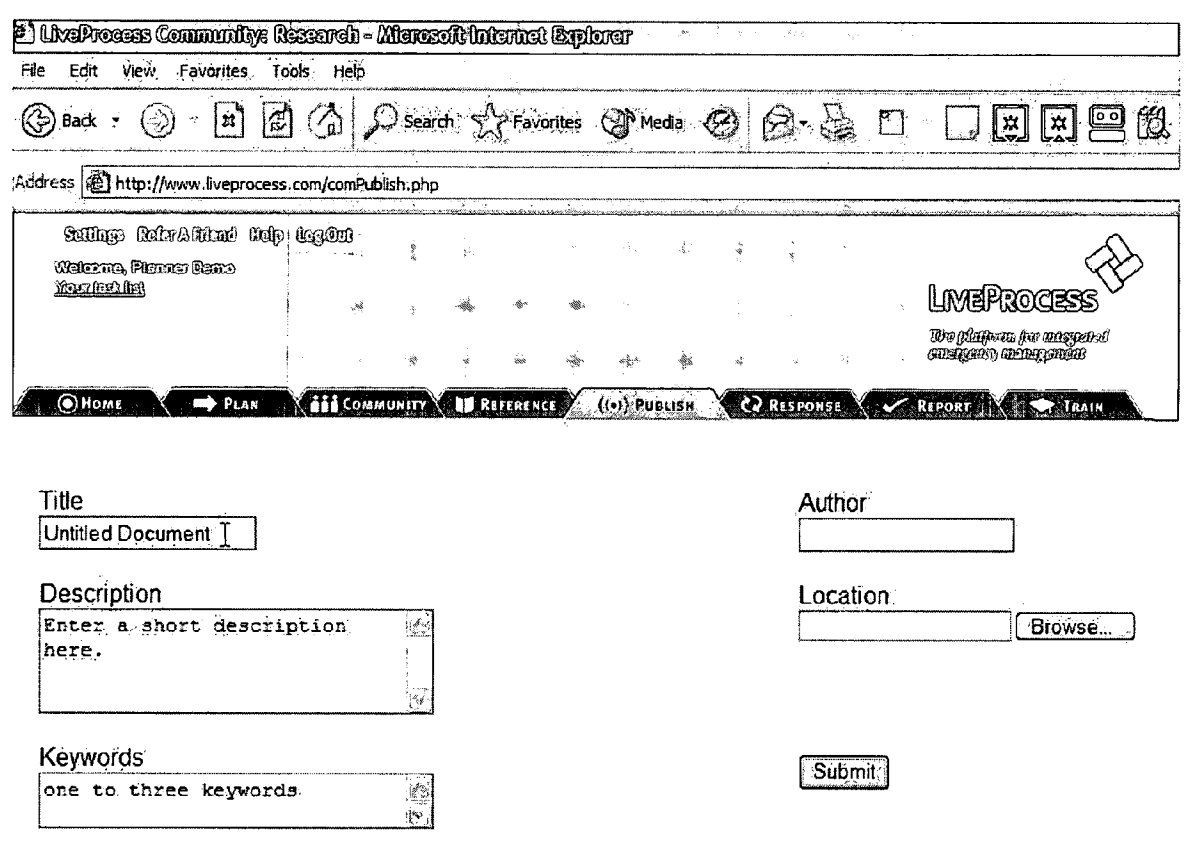

The Reference area (FIG. 61) allows the emergency planner to search the internal database for information published by others on the network. Users may search by means of keyword, facility type, facility size, bed count and geographical location. Items in the internal database are uploaded by users on the network via the Publish area. (FIG. 62). To upload a data file, the emergency planner simply fills out the supplied fields, selects the file and presses Submit. At this point, the uploaded file may be accessed by all other planners on the network.

Figure 55:
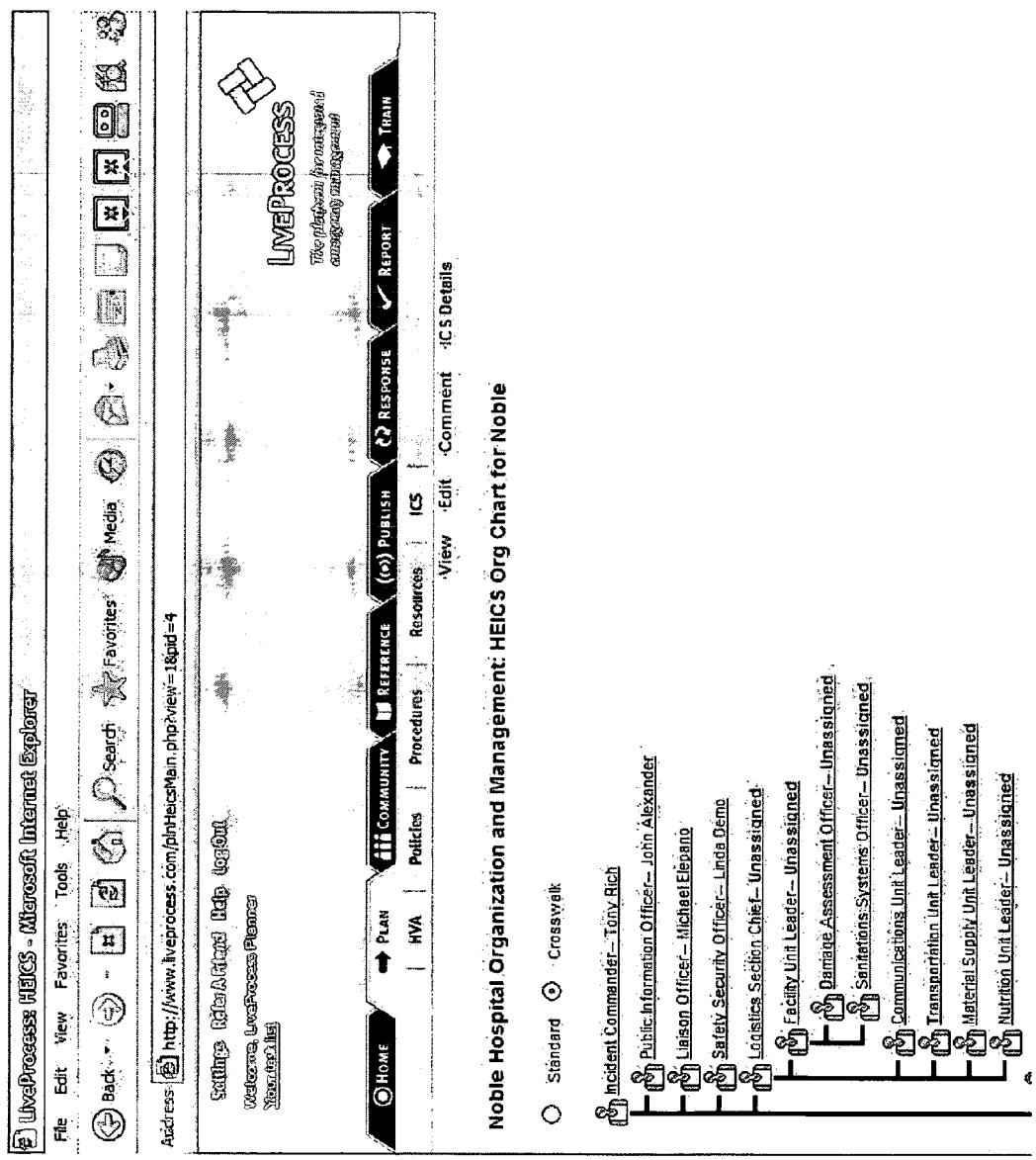

Response is used by the users of the plan with ICS permissions—this area allows them to see the portions of the plan that specifically relate to them, as they have been assigned to specific roles of the ICS. (FIG. 55, FIG. 57)

The Reporting Area allows the emergency planner to generate reports related to the emergency plan, including but not limited to: all Emergency Planning Committee comments, communication dates and times, and feedback, historical changes to the emergency plan and its component parts, audit trails of user access to the plan, actions logged during training, training test results by user or by test, After Action reports, changes and status of emergency resource inventories.

II. Database Tables 1. lp_user

This table holds every user in the LiveProcess community from Noble Trainees to LP Administrators. It is primarily tied to the LPUser class defined in classUser.php.

| | |
|---|---|
| key_user_id | int(11) |
| usr_forum_id | int(11) |
| usr_keys | smallint(6) |
| usr_planner | tinyint(4) |
| usr_first | varchar(50) |
| usr_last | varchar(50) |
| usr_username | varchar(50) |
| usr_password | varchar(50) |
| usr_salutation_id | int(11) |
| usr_dcreated | int(11) |
| usr_dmodified | int(11) |
| usr_status | tinyint(4) |

2. lp_group

This table holds the groups of the LiveProcess community. It is primarily tied to the LPGroup class defined in classGroup.php.

| | |
|---|---|
| key_group_id | int(11) |
| grp_forum_id | int(11) |
| grp_fullname | varchar(255) |
| grp_name | varchar(64) |
| grp_abbreviation | varchar(8) |
| grp_prefx | tinyint(4) |
| grp_prefy | tinyint(4) |
| grp_prefzoom | tinyint(4) |
| grp_status | tinyint(4) |

3. lp_user_group

This table links entries in the lp_user table to entries in the lp_group table. Through this table, users may belong to more than one group.

| | |
|---|---|
| key_user_group_id | int(11) |
| ug_user_id | int(11) |
| ug_group_id | int(11) |
| ug_isprimary | tinyint(4) |

4. lp_group_plan

This table links entries in the lp_group table to entries in the pln_plan table. Through this table, one group can have many plans and one plan can belong to multiple groups.

| | |
|---|---|
| key_group_plan_id | bigint(20) |
| gpp_group_id | bigint(20) |
| gpp_plan_id | bigint(20) |
| gpp_sortorder | int(11) |

5. lp_facility

This table holds all the facilities that will have a plan.

```
key_facility_id    bigint(20)
fac_name           varchar(255)
fac_bedcount       int(11)
fac_type           tinyint(4)
fac_description    text
fac_address1       varchar(255)
fac_address2       varchar(255)
fac_address3       varchar(255)
fac_city           varchar(255)
fac_state          varchar(32)
fac_zip            varchar(32)
fac_phone          varchar(64)
fac_fax            varchar(64)
fac_url            varchar(128)
fac_country        varchar(255)
fac_region         varchar(255)
fac_county         varchar(255)
fac_latitude       float(10,5)
fac_longitude      float(10,5)
fac_altitude       int(11)
fac_prefx          tinyint(4)
fac_prefy          tinyint(4)
fac_prefzoom       tinyint(4)
fac_status         tinyint(4)
```

6. lp_group_facility

This table joins facilities to groups

```
key_group_facility_id  bigint(20)
gfc_group_id           bigint(20)
gfc_facility_id        bigint(20)
gfc_dcreated           int(11)
gfc_status             tinyint(4)
```

7. lp_user_facility

This table joins users to facilities. This will be helpful in picking out which users sees which plans.

```
key_user_facility_id   bigint(20)
ufc_user_id            bigint(20)
ufc_facility_id        bigint(20)
ufc_dcreated           int(11)
ufc_status             tinyint(4)
```

8. lp_potentialclient

This table holds contact information of people who filled in our join page form during the early summer of 2004 before our SalesForce connection was implemented. This table is now obsolete.

```
key_potentialclient_id   int(11)
pc_first                 varchar(255)
pc_last                  varchar(255)
pc_email                 varchar(255)
pc_status                int(11)
```

9. lp_profile

This table holds the profile information used to create our profile page. This table is used primarily by classProfile.php.

```
key_profile_id       int(11)
pro_user_id          int(11)
pro_type_id          int(11)
pro_name             varchar(255)
pro_title            varchar(255)
pro_facility         varchar(255)
pro_body             text
pro_snippet          text
pro_photo_name       varchar(255)
pro_thumbnail_name   varchar(254)
pro_logo_name        varchar(255)
pro_photo_caption    text
pro_date_published   int(11)
pro_status           tinyint(4)
```

10. lp_salutation

This table holds all the salutations. It links to the lp_user.usr_salutaion_id cell for each user.

```
key_salutation_id   int(11)
sal_name            varchar(50)
sal_sortorder       tinyint(4)
```

Plan Tables

11. pln_plan

This table lists all the plans available on the LiveProcess Community. It is used primarily by the LPPlan class in classPlan.php.

```
key_plan_id        bigint(20)
pln_name           varchar(255)
pln_title          varchar(255)
pln_path           text
pln_filename       varchar(255)
pln_description    text
pln_author_id      bigint(20)
pln_overview_id    bigint(20)
pln_heics_id       bigint(20)
pln_dcreated       int(11)
pln_dmodified      int(11)
pln_version        varchar(255)
pln_status         tinyint(4)
```

12. pln_overview

This table holds all the overviews for LiveProcess plans. It is not being used currently.

```
key_overview_id    bigint(20)
ovr_name           varchar(255)
ovr_title          varchar(255)
ovr_copy           text
ovr_description    text
ovr_author_id      bigint(20)
ovr_dcreated       int(11)
ovr_dmodified      int(11)
ovr_status         tinyint(4)
```

13. pln_plan_epc

This table links executive planning committees (EPCs) to plans. Through this table, EPCs can look at multiple plans and plans can be reviewed by more than one EPC.

```
key_plan_epc_id    bigint(20)
ple_plan_id        bigint(20)
ple_epc_id         bigint(20)
```

14. pln_plan_heics

This table links HEICS systems to plans. Through this table, one plan can hold one or many HEICS or one HEICS can belong to one or many plans.

```
key_plan_heics_id  bigint(20)
plh_plan_id        bigint(20)
plh_heics_id       bigint(20)
```

15. pln_plan_hva

This table links HVAs to plans. Through this table, one plan can hold one or many HVAs or one HVA can belong to one or many plans.

```
key_plan_hva_id    bigint(20)
phv_plan_id        bigint(20)
phv_hva_id         bigint(20)
phv_sortorder      int(11)
```

16. pln_plan_resource

This table links resources to plans. Through this table, one plan can hold one or many resources or one resource can belong to one or many plans.

```
key_plan_resource_id  bigint(20)
plr_plan_id           bigint(20)
plr_resource_id       bigint(20)
```

17. pln_plan_facility

```
key_plan_facility_id  bigint(20)
plf_plan_id           bigint(20)
plf_facility_id       bigint(20)
```

EPC Tables

18. pln_epc

This table describes an EPC. It is primarily used by the LPEpc class defined in classEPC.php.

```
key_epc_id       bigint(20)
epc_name         varchar(255)
epc_description  text
epc_author_id    bigint(20)
epc_dcreated     int(11)
epc_dmodified    int(11)
epc_keys         int(11)
epc_status       tinyint(4)
```

19. pln_epcgroup

This table describes an EPC group. It is primarily used by the LPEpcgroup class in classEPC.php.

```
key_epcgroup_id  bigint(20)
epg_name         varchar(255)
epg_description  text
epg_author_id    bigint(20)
epg_dcreated     bigint(20)
epg_dmodified    bigint(20)
epg_keys         int(11)
epg_status       tinyint(4)
```

20. pln_user_epcgroup

This table joins users to an EPC group. Through this table an EPC group can have multiple users and one user can belong to multiple EPC groups.

```
key_user_epcgroup_id  bigint(20)
uep_user_id           bigint(20)
uep_epcgroup_id       bigint(20)
uep_keys              int(11)
uep_status            tinyint(4)
```

21. pln_epc_epcgroup

This table joins EPCs and EPC groups. Through this table, an EPC can have one or many EPC groups and one EPC group can belong to one or many EPCs.

```
key_epc_epcgroup_id  bigint(20)
eeg_epc_id           bigint(20)
eeg_epcgroup_id      bigint(20)
eeg_sortorder        int(11)
```

Incident Tables

22. inc_incident

This table is used by the response section of the platform which will allow incident commanders to create the incident and general staff to view the various states of the incident. Reports can be created from the data in this table as well.

```
key_incident_id   bigint(20)
inc_facility_id   bigint(20)
inc_code_id       bigint(20)
inc_tier_id       bigint(20)
inc_dstart        int(11)
inc_dend          int(11)
inc_dstatus       tinyint(4)
```

HEICS Tables

23. pln_heics

```
key_heics_id     bigint(20)
hcs_name         varchar(255)
hcs_description  text
hcs_author_id    bigint(20)
hcs_dcreated     int(11)
hcs_dmodified    int(11)
hcs_status       bigint(20)
```

24. pln_heicsrole

| | |
|---|---|
| key_heicsrole_id | bigint(20) |
| hsr_formtemplate_id | bigint(20) |
| hsr_author_id | bigint(20) |
| hsr_name | varchar(255) |
| hsr_dcreated | int(11) |
| hsr_dmodified | int(11) |
| hsr_status | tinyint(4) |

25. pln_heics_heicsrole

| | |
|---|---|
| key_heics_heicsrole_id | bigint(20) |
| hsr_heics_id | bigint(20) |
| hsr_heicsrole_id | bigint(20) |
| hsr_parent_id | bigint(20) |
| hsr_commandcenter | varchar(255) |
| hsr_commandcontact | varchar(255) |
| hsr_sortorder | int(11) |

26. pln_heicsrole_user

| | |
|---|---|
| key_heicsrole_user_id | bigint(20) |
| hru_heics_heicsrole_id | bigint(20) |
| hru_user_id | bigint(20) |
| hru_firstname | varchar(255) |
| hru_lastname | varchar(255) |

27. pln_heicsformtemplate

| | |
|---|---|
| key_heicsformtemplate_id | bigint(20) |
| hft_name | varchar(255) |
| hft_description | text |
| hft_mission | text |
| hft_blueprint | text |
| hft_author_id | bigint(20) |
| hft_dcreated | int(11) |
| hft_dmodified | int(11) |
| hft_status | tinyint(4) |

28. pln_heicsform

| | |
|---|---|
| key_heicsform_id | bigint(20) |
| hsf_heicsformtemplate_id | bigint(20) |
| hsf_name | varchar(255) |
| hsf_description | text |
| hsf_mission | text |
| hsf_header | text |
| hsf_effectivestart | varchar(255) |
| hsr_effectiveend | varchar(255) |
| hsf_author_id | bigint(20) |
| hsf_dcreated | int(11) |
| hsf_dmodified | int(11) |
| hsf_status | tinyint(4) |

29. pln_heicssheet

| | |
|---|---|
| key_heicssheet_id | bigint(20) |
| hss_name | varchar(255) |
| hss_filename | varchar(255) |
| hss_path | varchar(255) |
| hss_dcreated | int(11) |

-continued

| | |
|---|---|
| hss_dmodified | int(11) |
| hss_status | tinyint(4) |

30. pln_heicsrole_heicsform

| | |
|---|---|
| key_heicsrole_heicsform_id | bigint(20) |
| hrf_heicsrole_id | bigint(20) |
| hrf_heicsform_id | bigint(20) |

31. pln_heicsrole_heicssheet

| | |
|---|---|
| key_heicsrole_heicssheet_id | bigint(20) |
| hrs_heicsrole_id | bigint(20) |
| hrs_heicssheet_id | bigint(20) |

32. pln_heicsformsection

| | |
|---|---|
| key_heicsformsection_id | bigint(20) |
| hfs_name | varchar(255) |
| hfs_author_id | bigint(20) |
| hfs_dcreated | int(11) |
| hfs_dmodified | int(11) |
| hfs_status | tinyint(4) |

33. pln_heicsform_heicsformsection

| | |
|---|---|
| key_heicsform_heicsformsection_id | bigint(20) |
| hfs_heicsform_id | bigint(20) |
| hfs_heicsformsection_id | bigint(20) |
| hfs_sortorder | int(11) |

34. pln_heicsformitem

| | |
|---|---|
| key_heicsformitem_id | bigint(20) |
| hfi_name | varchar(255) |
| hfi_body | text |
| hfi_type | tinyint(4) |
| hfi_author_id | bigint(20) |
| hfi_dcreated | int(11) |
| hfi_dmodified | int(11) |
| hfi_status | tinyint(4) |

35. pln_heicsformsection_heicsformitem

| | |
|---|---|
| key_heicsformsection_heicsformitem_id | bigint(20) |
| hfh_heicsformsection_id | bigint(20) |
| hfh_heicsformitem_id | bigint(20) |
| hfh_sortorder | int(11) |

36. pln_heicstemplate

| | |
|---|---|
| key_heicstemplate_id | bigint(20) |
| hst_name | varchar(255) |
| hst_title | varchar(255) |

-continued

```
hst_description              text
hst_heics_heicsrole_chain    text
hst_heicsformtemplate_heicsrole_chain    text
hst_heicssheet_heicsrole_chain    text
hst_author_id                bigint(20)
hst_dcreated                 int(11)
hst_dmodified                int(11)
hst_status                   tinyint(4)
```

Task Tables
37. tsk_plantask

```
key_plantask_id    bigint(20)
plt_name           varchar(255)
plt_tablename      varchar(255)
pit_baseurl        text
plt_idprefix       varchar(8)
plt_status         tinyint(4)
```

38. tsk_task

```
key_task_id        bigint(20)
tsk_plan_id        bigint(20)
tsk_element_id     bigint(20)
tsk_plantask_id    bigint(20)
tsk_assigner_id    bigint(20)
tsk_message        text
tsk_dcreated       int(11)
tsk_dclosed        int(11)
tsk_status         tinyint(4)
```

39. tsk_task_user

```
key_task_user_id   bigint(20)
tku_task_id        bigint(20)
tku_user_id        bigint(20)
tku_dassigned      int(11)
tku_dseen          int(11)
tku_dlastseen      int(11)
tku_dclosed        int(11)
```

40. tsk_comment

```
key_comment_id     bigint(20)
cmt_task_id        bigint(20)
cmt_plantask_id    bigint(20)
cmt_element_id     bigint(20)
cmt_user_id        bigint(20)
cmt_body           text
cmt_dcreated       int(11)
```

Tables for HVA
41. hva_analysis

```
key_analysis_id         int(11)
anl_name                varchar(255)
anl_description         text
anl_version             varchar(255)
anl_facility_name       varchar(255)
anl_facility_bedsize    int(11)
anl_author_id           int(11)
anl_dcreated            int(11)
anl_dmodified           int(11)
anl_status              int(11)
```

42. hva_analysis_section

```
key_analysis_section_id    bigint(20)
ans_analysis_id            bigint(20)
ans_section_id             bigint(20)
ans_sortorder              int(11)
```

43. hva_analysis_template

```
key_analysis_template_id   int(11)
ant_name                   varchar(255)
ant_description            text
ant_hazardlist             text
ant_vulnerabilitylist      text
ant_author_id              int(11)
```

44. hva_hazard

```
key_hazard_id      int(11)
haz_name           varchar(255)
haz_description    text
haz_category_id    int(11)
haz_author_id      int(11)
haz_status         int(11)
```

45. hva_hazard_analysis

```
key_hazard_analysis_id   int(11)
hza_section_id           bigint(20)
hza_hazard_id            int(11)
hza_analysis_id          int(11)
hza_sortorder            int(11)
```

46. hva_hazard_category

```
key_hazard_category_id   int(11)
hzc_name                 varchar(255)
hzc_status               int(11)
```

47. hva_section

```
key_section_id     bigint(20)
sec_name           varchar(255)
sec_author_id      bigint(20)
sec_dcreated       int(11)
sec_dmodified      lint(11)
sec_status         tinyint(4)
```

48. hva_vulnerability

```
key_vulnerability_id    int(11)
vul_type                varchar(255)
vul_label               varchar(255)
vul_ismitigation        tinyint(4)
vul_min                 int(11)
vul_max                 int(11)
vul_question            text
vul_author_id           int(11)
vul_sortorder           int(11)
vul_status              int(11)
```

49. hva_vulnerability_analysis

```
key_vulnerability_analysis_id   int(11)
vla_hza_id                      int(11)
vla_vulnerability_id            int(11)
vla_value                       varchar(255)
```

Tables for Resources 50. pln_resource

```
key_resource_id    bigint(20)
res_company        varchar(255)
res_address1       varchar(255)
res_address2       varchar(255)
res_address3       varchar(255)
res_city           varchar(255)
res_state          varchar(8)
res_zip            varchar(32)
res_phone          varchar(64)
res_fax            varchar(64)
res_email          varchar(255)
res_website        varchar(255)
res_type_id        bigint(20)
res_author_id      bigint(20)
res_latitude       float(10,5)
res_longitude      float(10,5)
res_altitude       decimal(10,0)
res_dcreated       int(11)
res_dmodified      int(11)
res_status         int(11)
```

51. pln_resourcetype

```
key_resource_type_id   bigint(20)
rst_name               varchar(255)
rst_category_id        int(11)
rst_sortorder          int(11)
rst_dcreated           int(11)
rst_dmodified          int(11)
rst_status             int(11)
```

52. pln_contact

```
key_contact_id     bigint(20)
cnt_resource_id    bigint(20)
cnt_first          varchar(255)
cnt_last           varchar(255)
cnt_title          varchar(255)
cnt_address1       varchar(255)
cnt_address2       varchar(255)
cnt_address3       varchar(255)
```

-continued

```
cnt_city           varchar(255)
cnt_state          varchar(8)
cnt_zip            varchar(16)
cnt_phone          varchar(64)
cnt_mobile         varchar(64)
cnt_fax            varchar(64)
cnt_email          varchar(255)
cnt_dcreated       int(11)
cnt_dmodified      int(11)
cnt_status         int(11)
```

Tables for Codes 53. pln_code

```
key_code_id
cod_name
cod_color
cod_title
cod_description
cod_author_id
cod_dcreated
cod_dmodified
cod_status
```

54. pln_plan_code

```
key_plan_code_id
plc_plan_id
plc_code_id
plc_sortorder
```

55. pln_segment

```
key_segment_id
seg_author_id
seg_name
seg_title
seg_body
seg_isprocedure
seg_type
seg_dcreated
seg_dmodified
seg_status
```

56. pln_code_hazardannex

```
key_code_hazardannex_id
cdh_code_id
cdh_hazard_id
cdh_sortorder
```

57. pln_code_segment

```
key_code_segment_id
cds_code_id
cds_segment_id
cds_sortorder
```

58. pin_code_heicsform

>       key_code_heicsform_id
>       chf_code_id
>       chf_heicsform_id
>       chf_sortorder Training Tables 59. tm_patient >       key_patient_id
>       pnt_first
>       pnt_last
>       pnt_sex
>       pnt_age
>       pnt_dob
>       pnt_race
>       pnt_address
>       pnt_city
>       pnt_state
>       pnt_complaint
>       pnt_presenting
>       pnt_meds
>       pnt_presentillness
>       pnt_historymed
>       pnt_historysoc
>       pnt_exam
>       pnt_pulse
>       pnt_resp
>       pnt_bp
>       pnt_temp
>       pnt_spo2
>       pnt_author_id
>       pnt_dcreated
>       pnt_dmodified
>       pnt_status III. Scenarios 1. Introduction This section will provide usage scenarios for the LiveProcess platform.

Key features of LiveProcess include:

1. Easily create, maintain and update an accurate, current and facility specific all-hazards HEICS-based plan.
2. Provide a clear understanding of potential roles and responsibilities in any incident as well as reports that is so simple anyone can be an incident commander.
3. Provide role-specific, immediate 24/7 secure access anywhere to the most current plan and real-time response activation.
4. Ability to quantify actual and potential losses and therefore value the mitigation effort.
5. Reduce time away from the worksite for training.
6. Ability to more quickly develop a broad range of customized drills.
7. Effectively and efficiently integrate into regional plan without rewriting your facility's plan.

2. Documentation of Usage Scenarios 2.1 S1 Create New Plan 2.1.1 Scenario Definition A user wishes to create an emergency management plan for his facility and have it available online for authorized users to view.

2.1.2 Description

Figure 20:
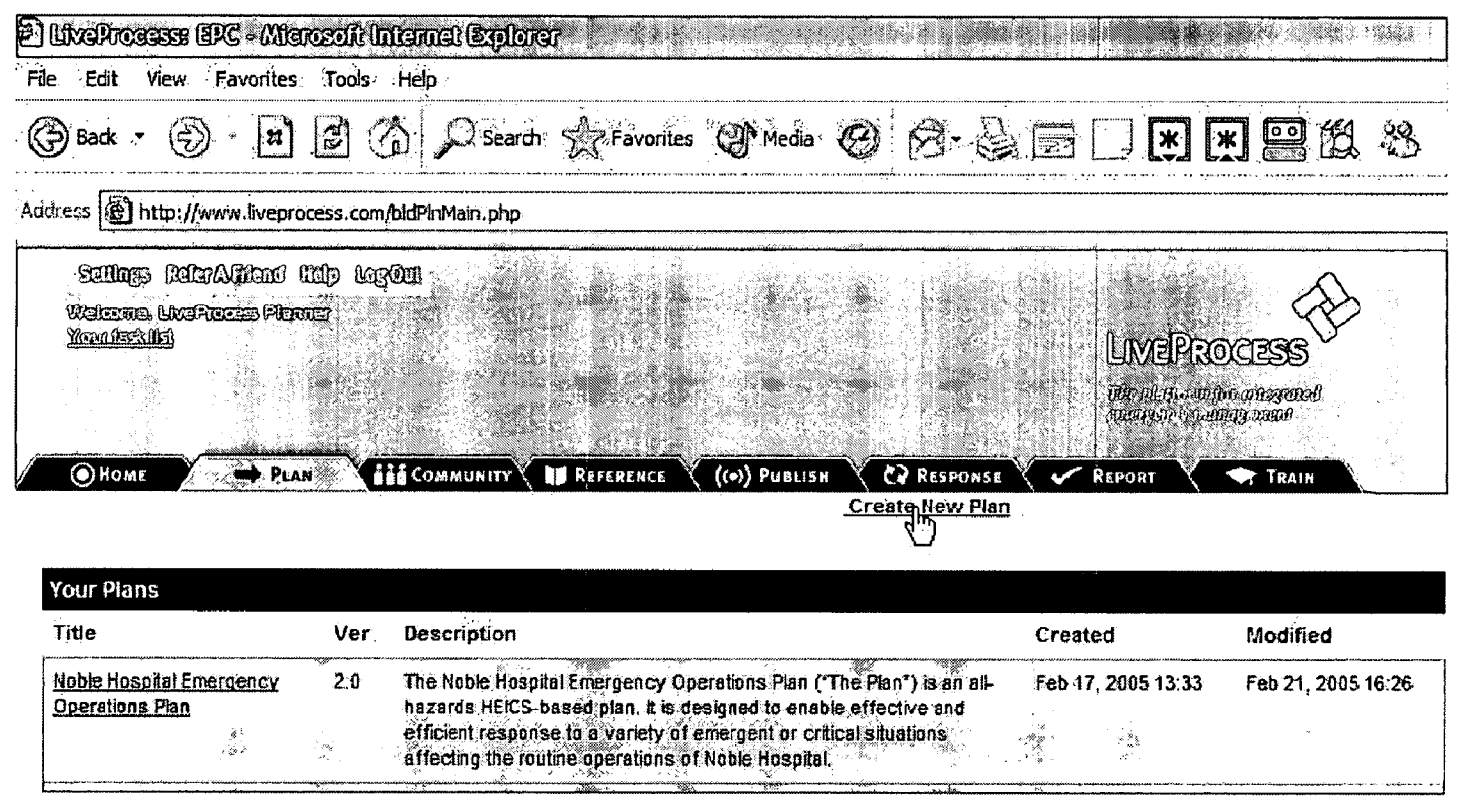

To create a new plan, the user would log into LiveProcess, click on the "PLAN" tab, and then on the "Create New Plan" link as illustrated in FIG. 1. This would bring up the "Add New Plan" page, where the user would fill in a filename, title, description, and version number for the plan and then click "Submit." A corresponding screenshot is shown in FIG. 20.

2.2 S2 Select Plan/Open Plan 2.2.1 Scenario Definition

A user wishes to select and open an existing emergency management plan for his facility so that he can view and edit the content.

2.2.2 Description

Figure 21:
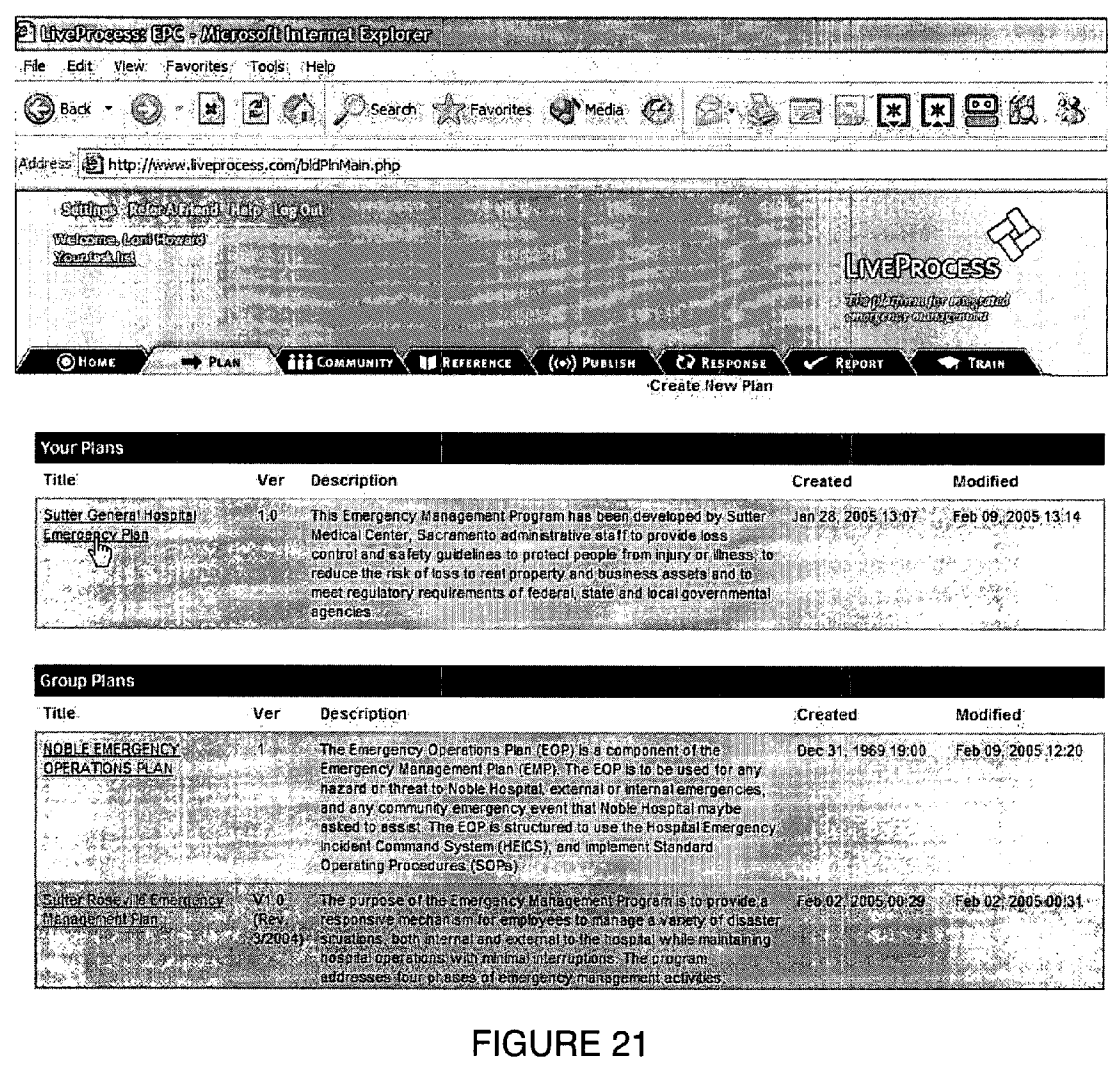

To select and open a previously saved version of a plan, the user would click on the "PLAN" tab. This would bring up the plan main page, where he could view a list of available plans, categorized into sections entitled "Your Plans" and "Group Plans." To open a plan, he would click on the plan title, as illustrated in FIG. 2. This would bring up the plan details page shown in FIG. 3. A corresponding screenshot is shown in FIG. 21.

2.3 S3 Add a Policy 2.3.1 Scenario Definition

The user wishes to add a policy to his emergency management plan. He may already have the policy content in a Microsoft Word document or an Adobe Acrobat PDF but would like it to be available online at LiveProcess where authorized users may access it.

2.3.2 Description

Figure 3:
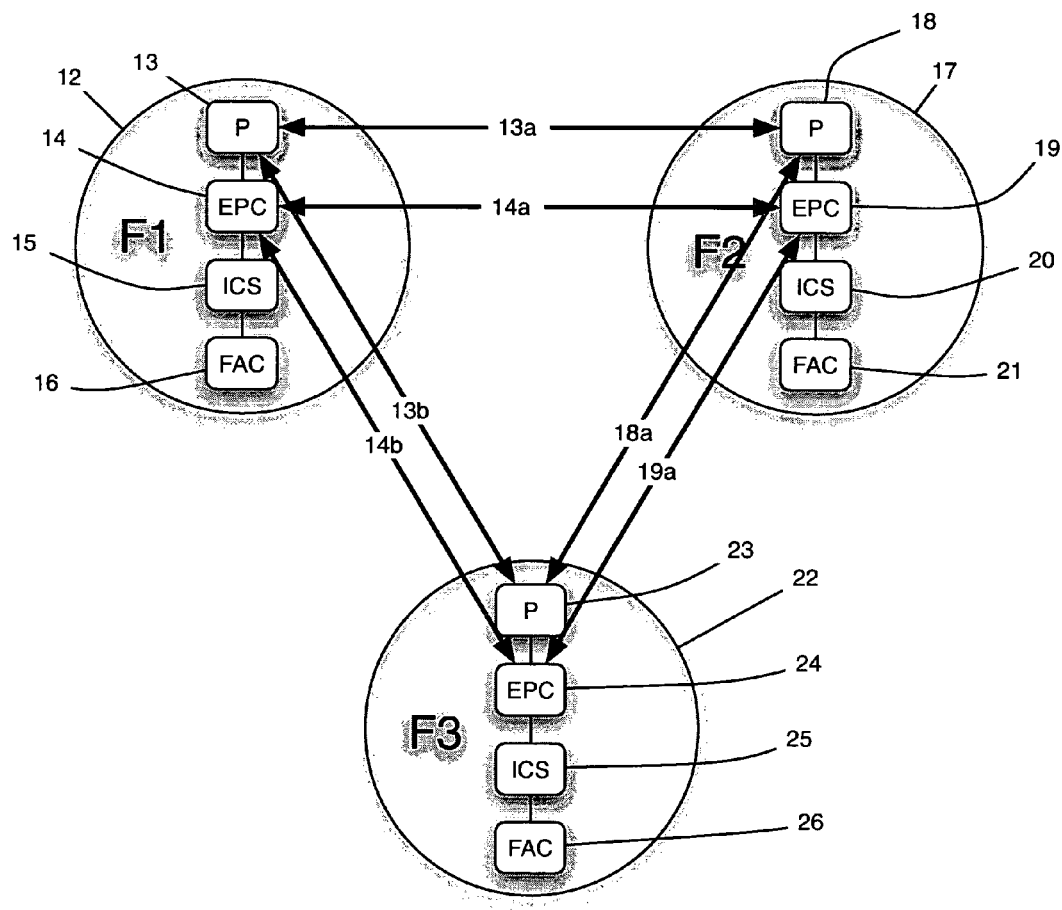
Figure 4:
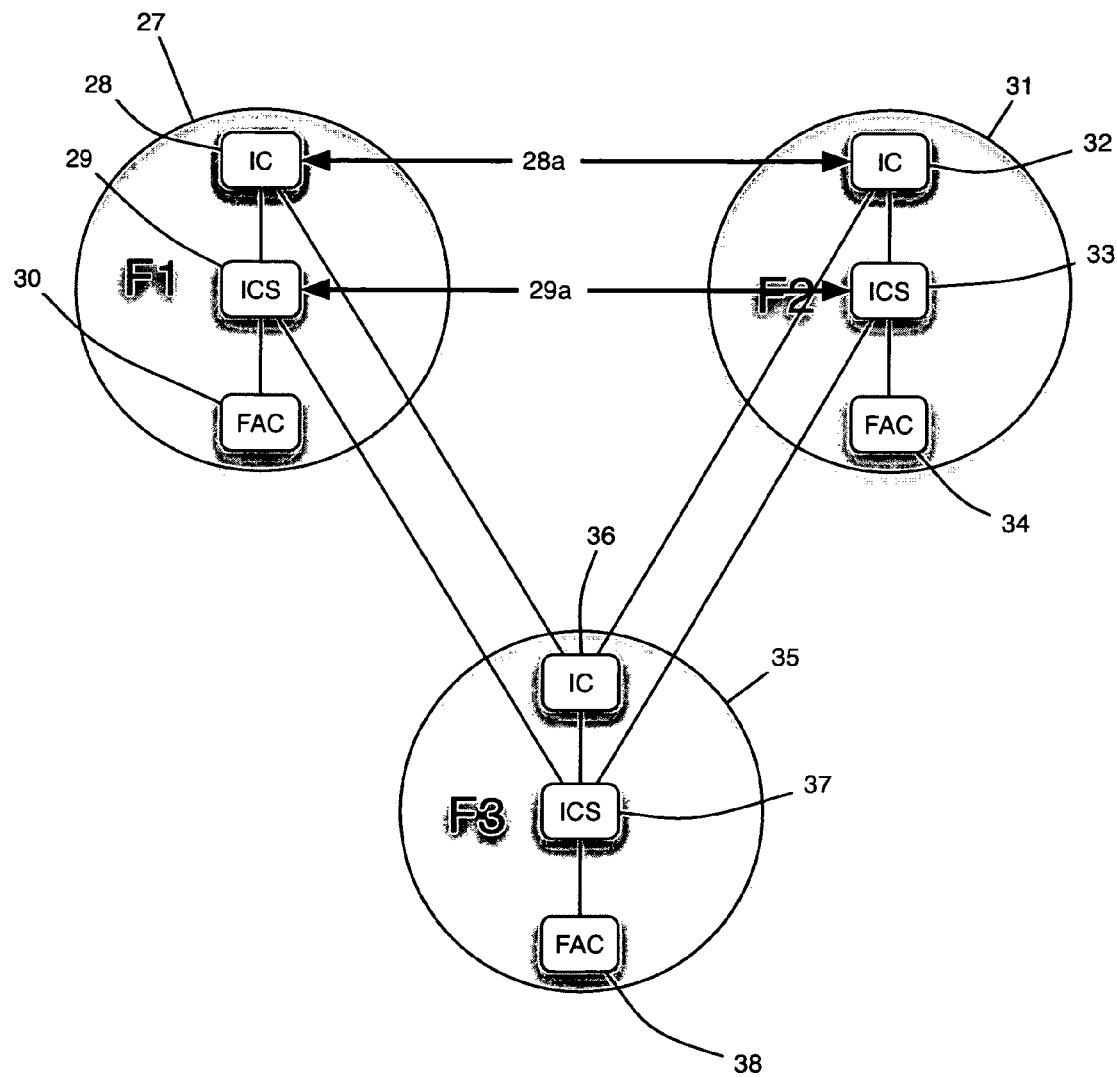
Figure 23:
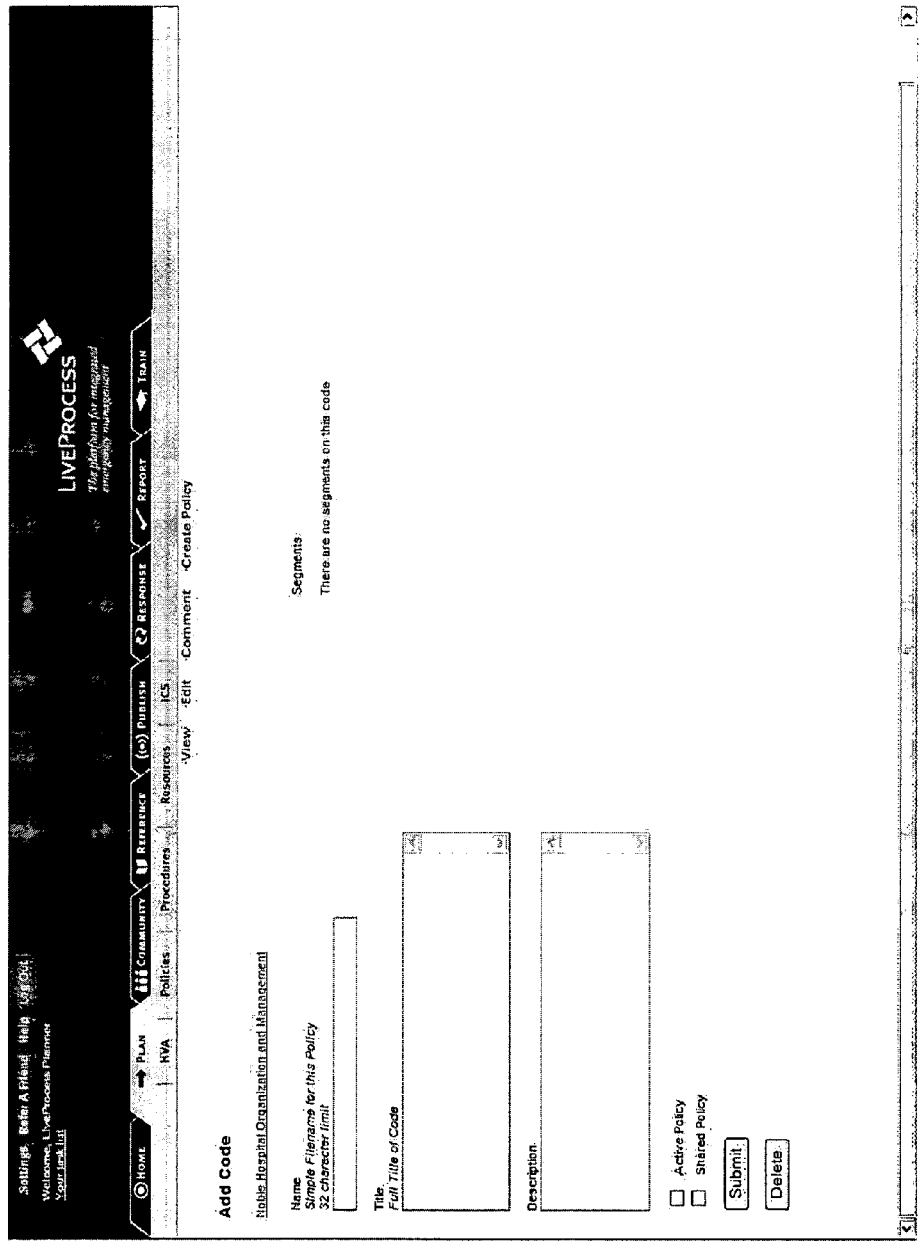

Once a user has created a plan, he is able to add policies to it. To add a policy, the user would click on the "PLAN" tab, select and open a plan, and then click on the "Add a Policy" link located on the plan details page, as illustrated in FIG. 3. This would take the user to the "Add Code" page, shown in FIG. 4, where he would input a title and description for the policy. The "Add Code" page also enables him to indicate whether the policy is an "Active Policy" and/or a "Shared Policy." After filling in the information, the user would click "Submit" to save the new policy. Corresponding screenshots are shown in FIGS. 22 and 23.

2.4 S4 Import a Policy 2.4.1 Scenario Definition

The user wishes to import a policy created by another hospital or user, into his own emergency management plan.

2.4.2 Description

Figure 5:
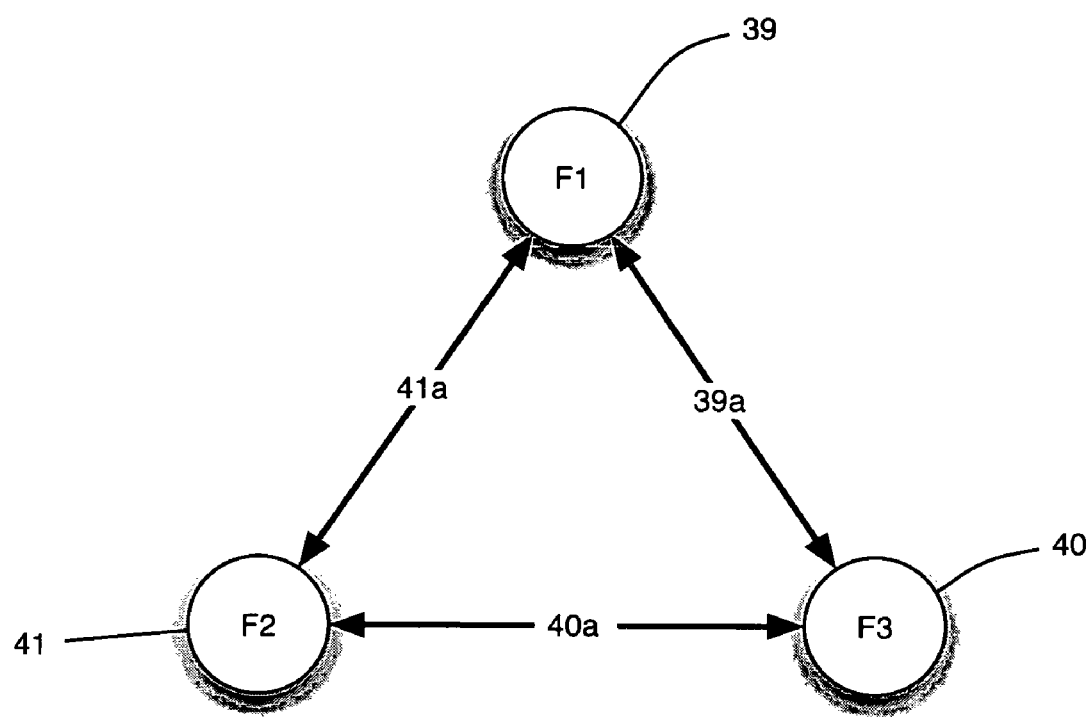
Figure 7:
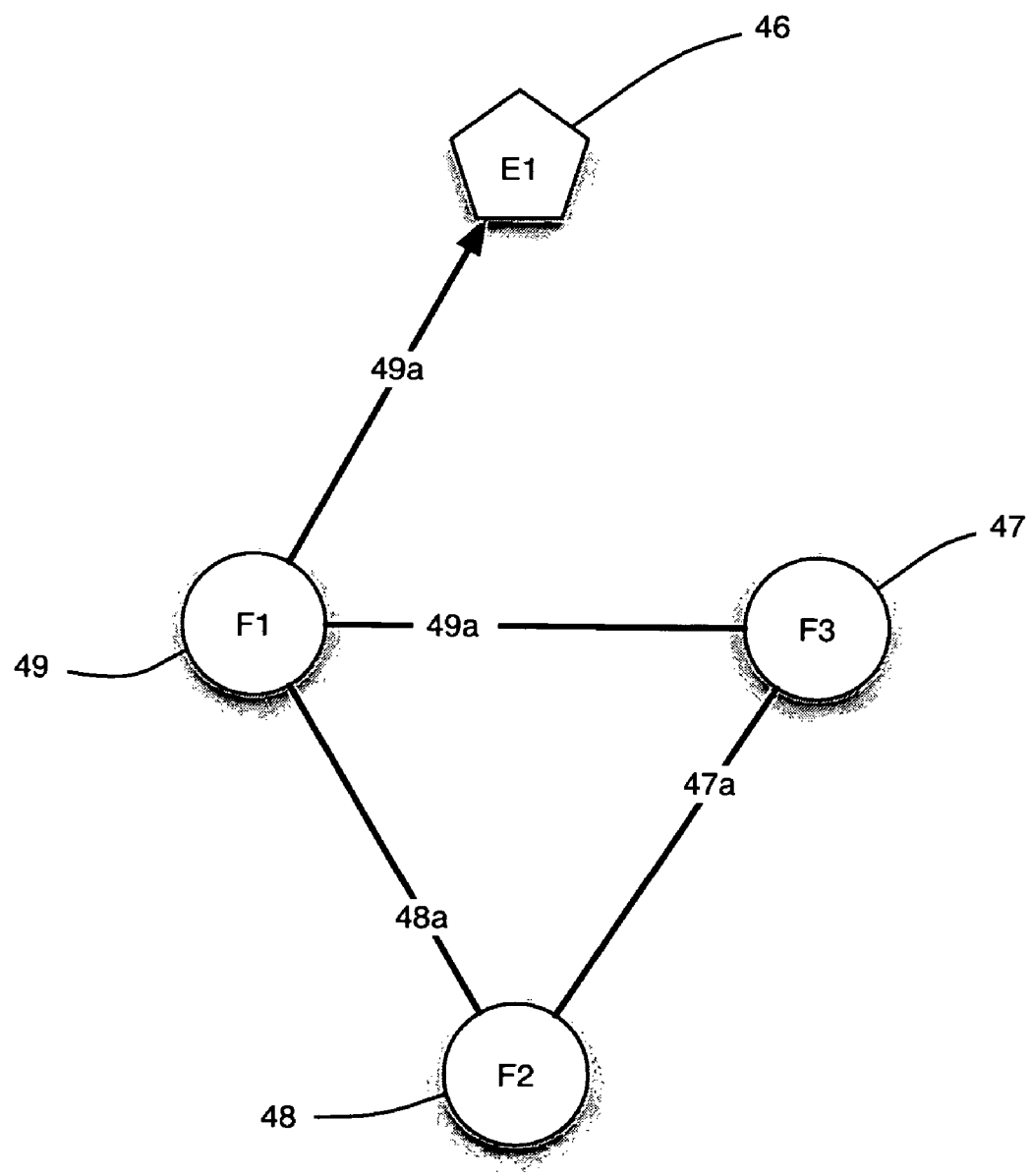

When a user adds a policy to his plan, he has the option to make it private or to share the policy with other users of LiveProcess. If a policy has been made public, other users may import it into their own plans. To import a policy, the user would click on the "PLAN" tab, select and open a plan, and then click on the "Import a Policy" link located on the plan details page, as illustrated in FIG. 5. This would take the user to the "Policy Search" page, shown in FIG. 6, where he would input keywords to search for a policy. After hitting "Search" the user will see a list of search results. He would then click on one of the policies to view it, as shown in FIG. 7. To import the policy into his plan, he would click on the "Attach (Policy Name)" link. The policy would immediately be added to his plan, where he could edit it to make it specific to his facility. Corresponding screenshots are shown in FIGS. 24-26.

2.5 S5 Add Segment

2.5.1 Scenario Definition

The user would like to add a segment, or section, to a policy in his emergency management plan.

2.5.2 Description

Figure 8:
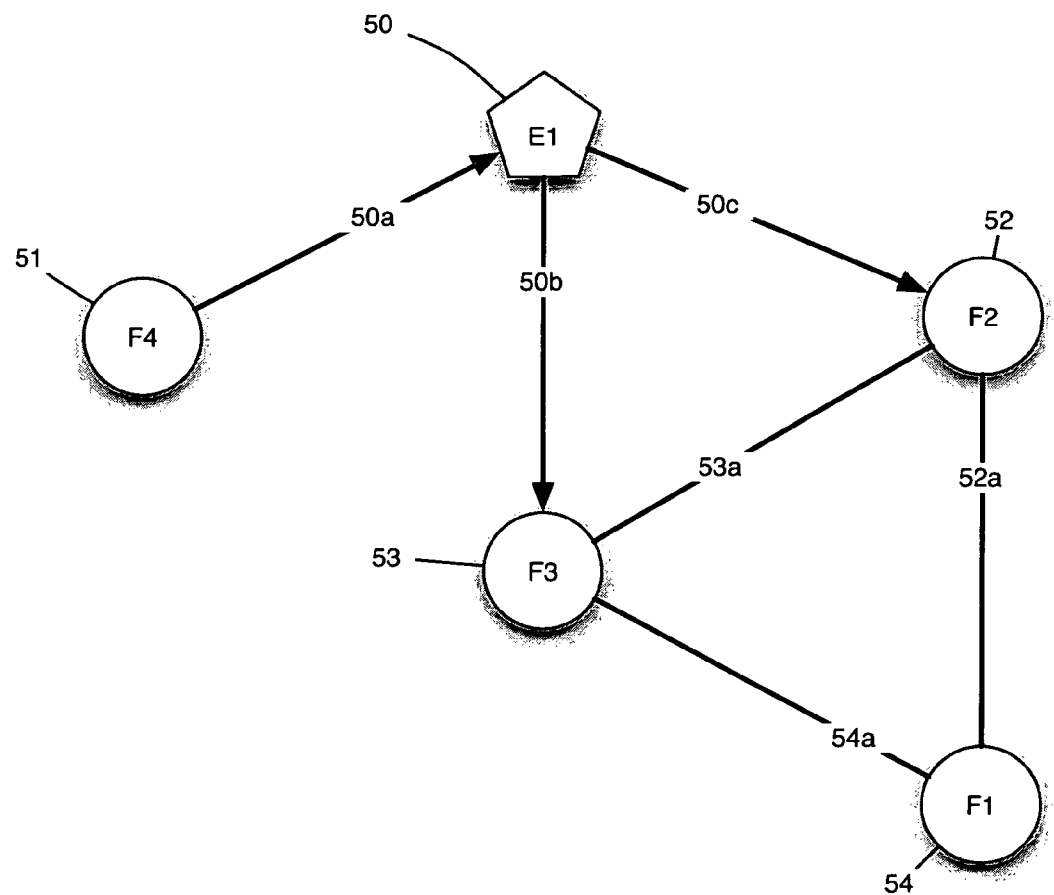
Figure 9:
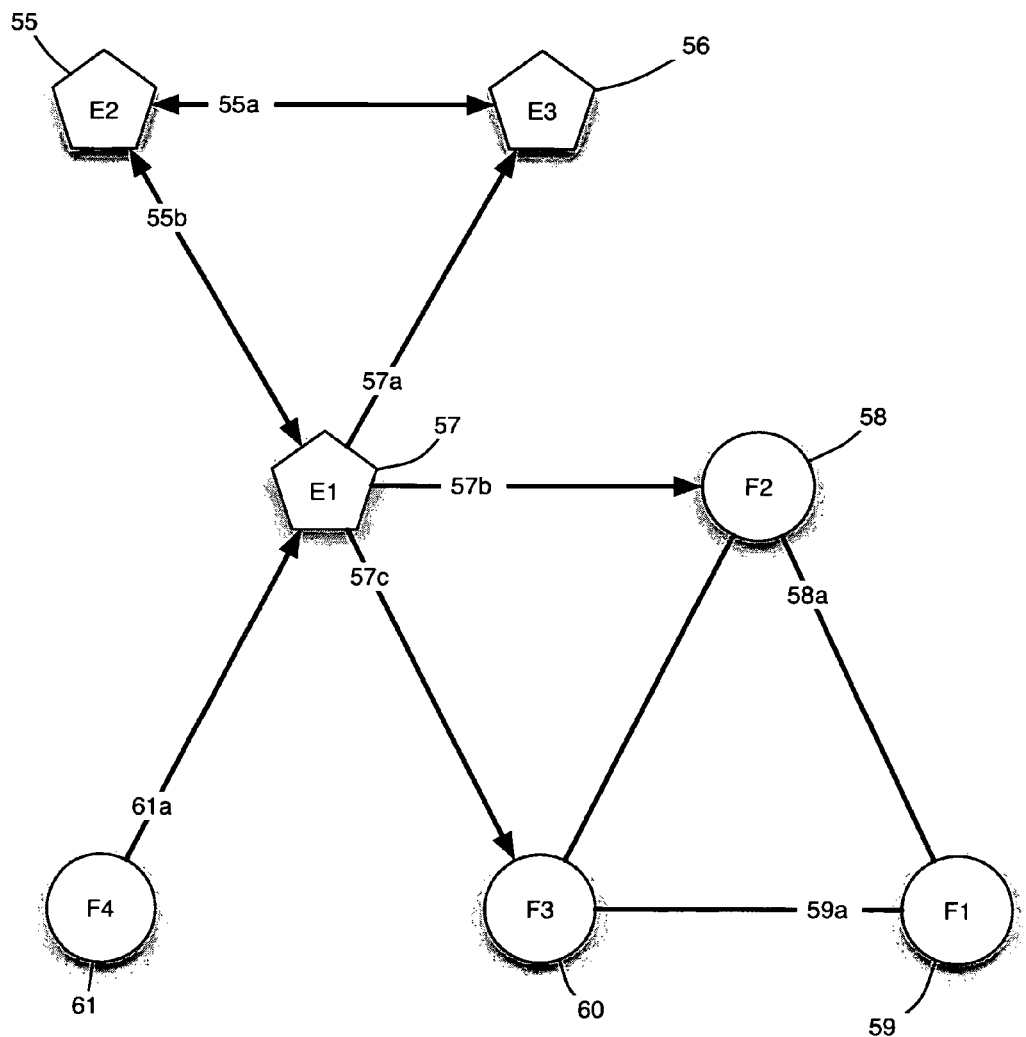
Figure 28:
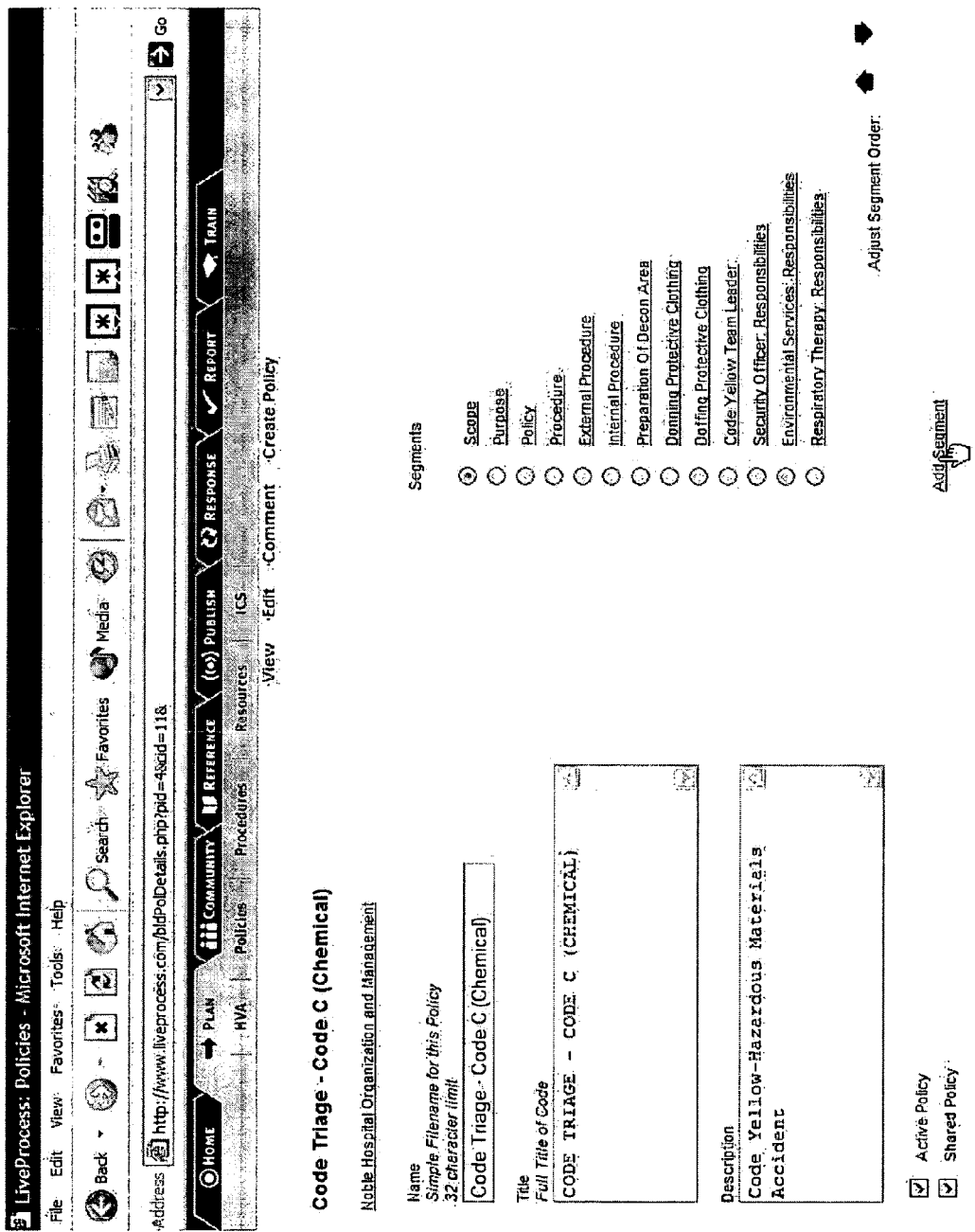
Figure 29:
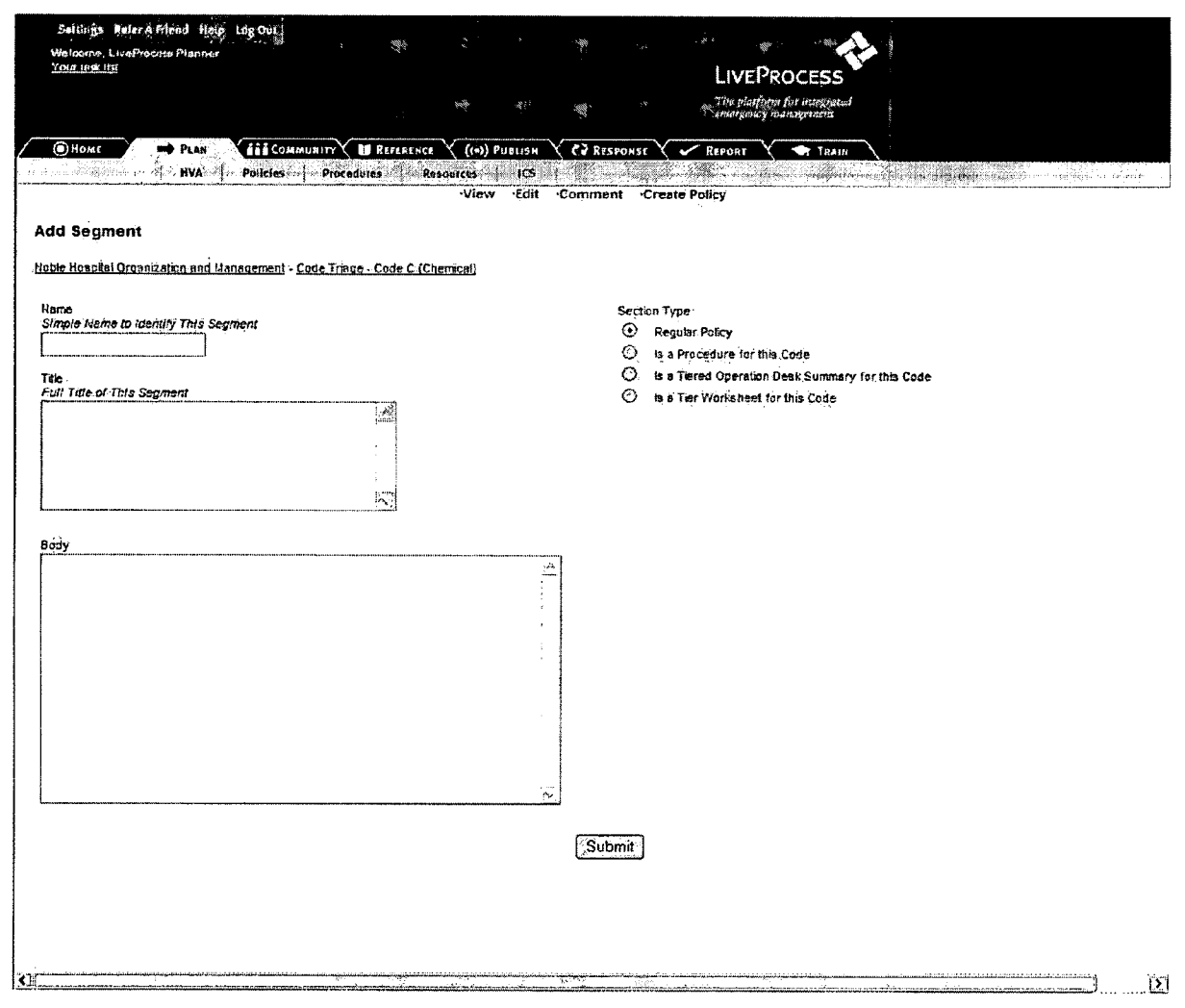

To add a segment or section to a policy, the user would click on the relevant policy, and then click on "Edit" as shown in FIG. 8. This would take him to the policy details page where he would click "Add Segment" as shown in FIG. 9. This would take him to the "Add Segment" page, shown in FIG. 10, where he would type or paste in the text of his policy segment, and then click "Submit." Corresponding screenshots are shown in FIGS. 27-29.

2.6 S6 Add Comment

2.6.1 Scenario Definition

The user wishes to post a comment on a particular policy, segment of a policy, or procedure. He wishes to send this comment to certain members of his emergency planning committee and have it time/date stamped.

2.6.2 Description

Figure 11:
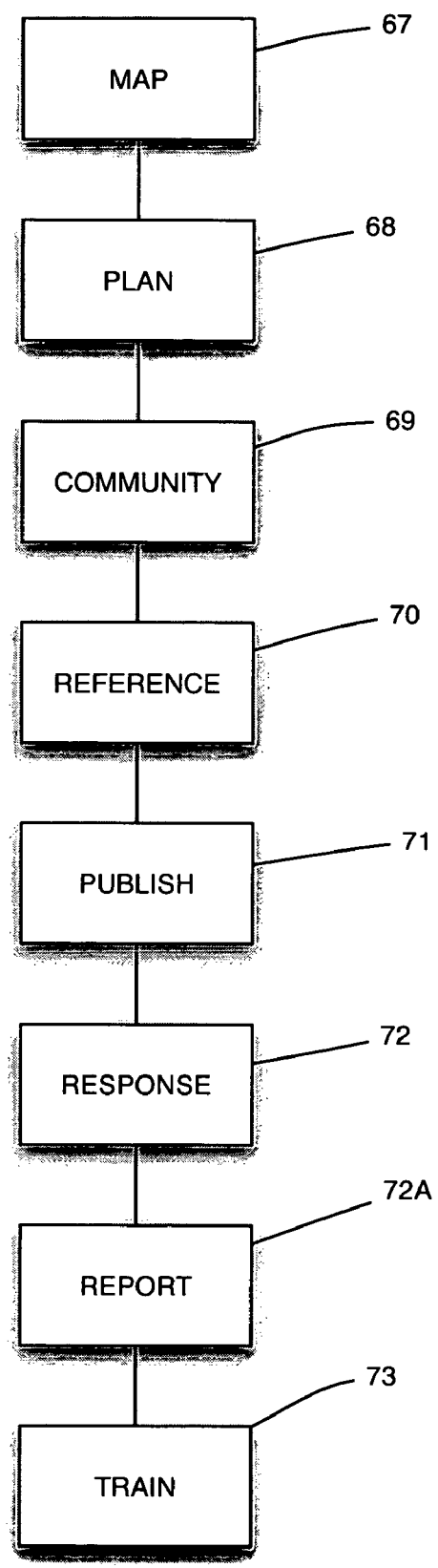
Figure 30:
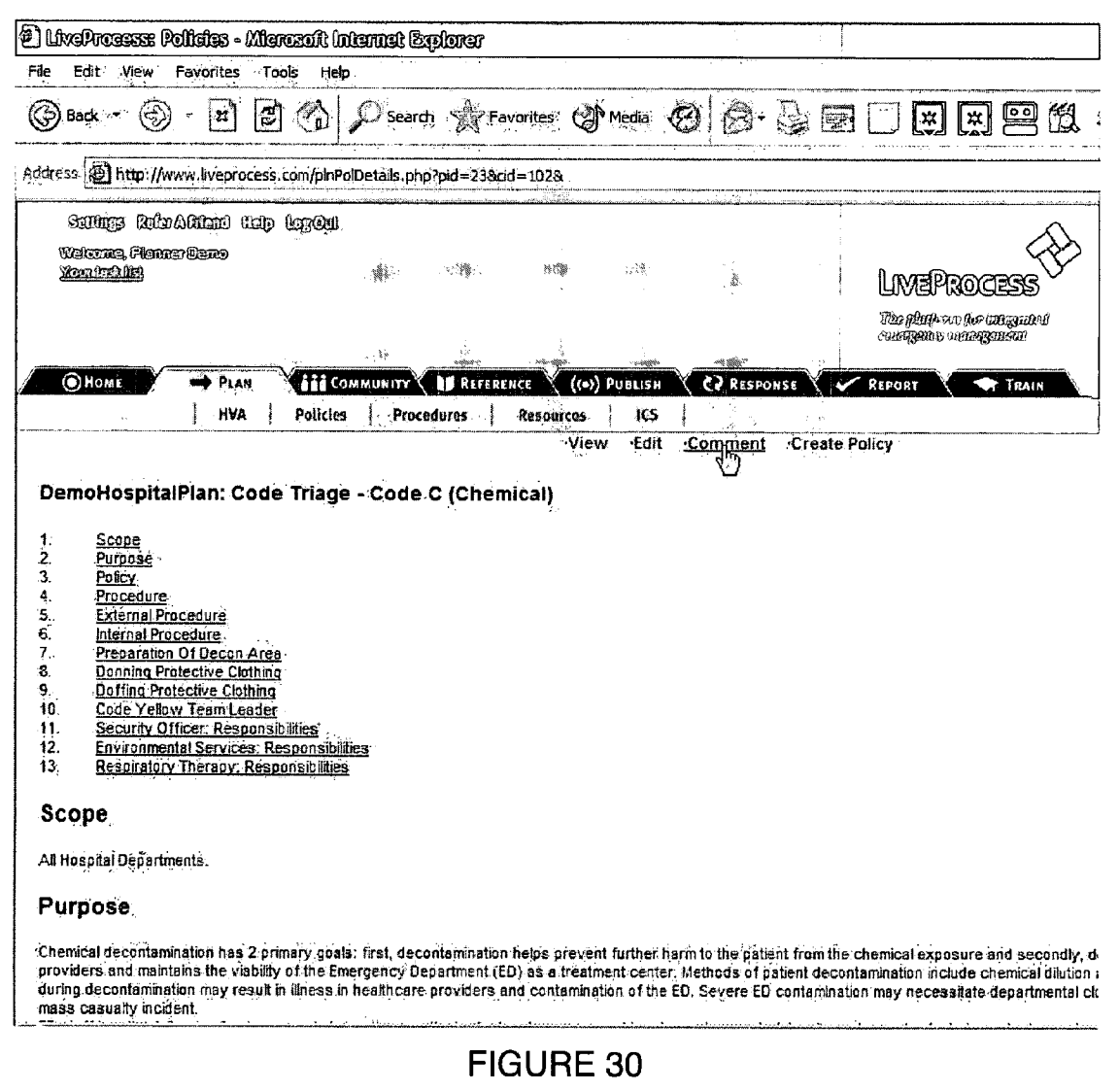
Figure 31:
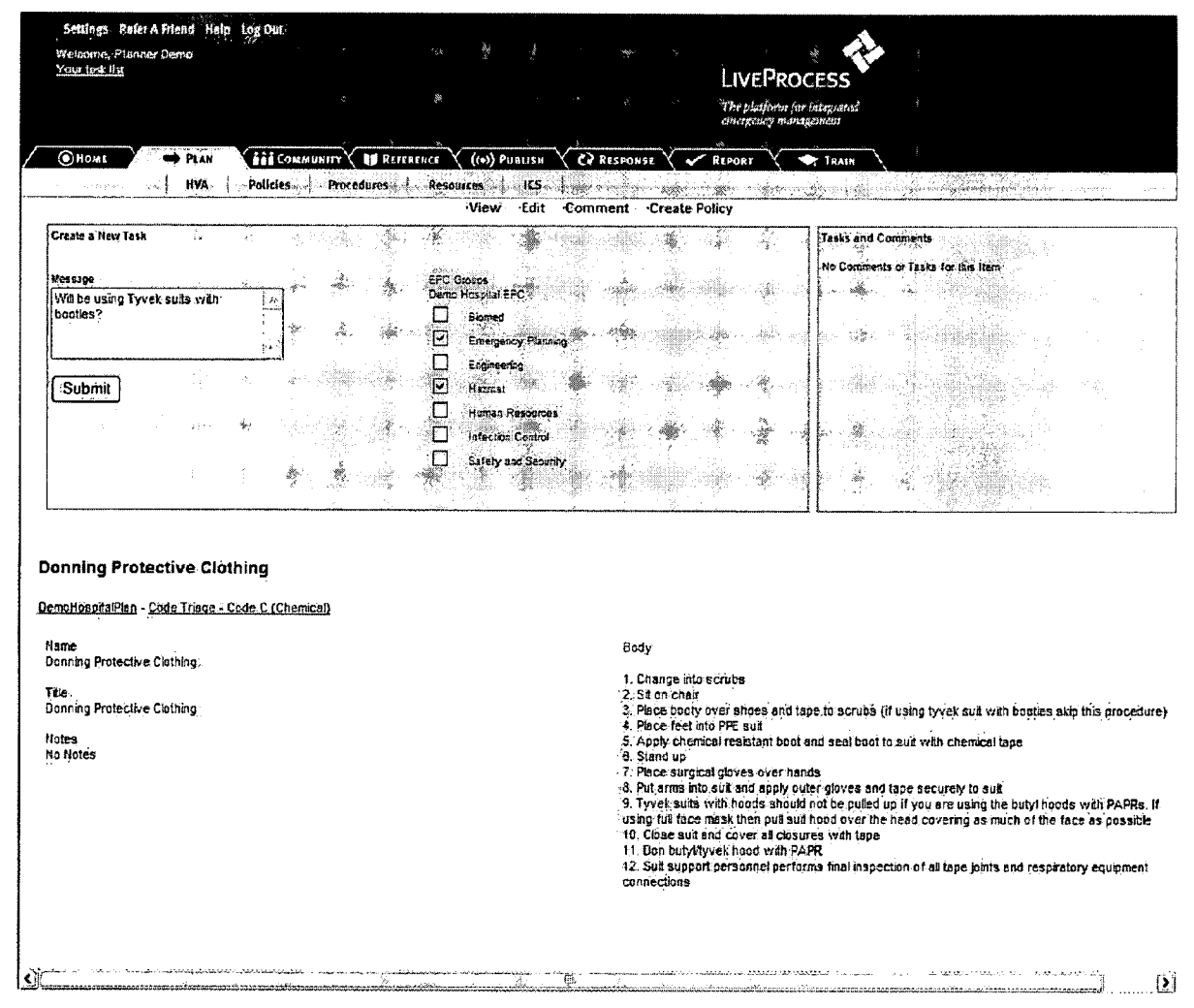

In order to post a comment, the user would first select the relevant policy, segment, or procedure, and then click "Comment," as show in FIG. 11. This would take him to the "Comment" page, shown in FIG. 12, where he could choose to comment on the entire policy or a particular segment of the policy. The user would then type in his comment or question into the "Message" box, select which committee members should receive his comment, and then click "Submit." Corresponding screenshots are shown in FIGS. 30-31.

In the example in FIG. 12 above, the user is posting a comment on the "Donning Protective Clothing" segment of the "Code Triage—Code C (Chemical) policy. Specifically, he is asking whether staff will be using "Tyvek suits with booties." He has selected that this question be sent to members of his "Emergency Planning" and "Hazmat Committees."

2.7 S7 Respond to Comment

2.7.1 Scenario Definition

A user or emergency planning committee member wishes to view and respond to comments posted on the plan.

2.7.2 Description

Figure 32:
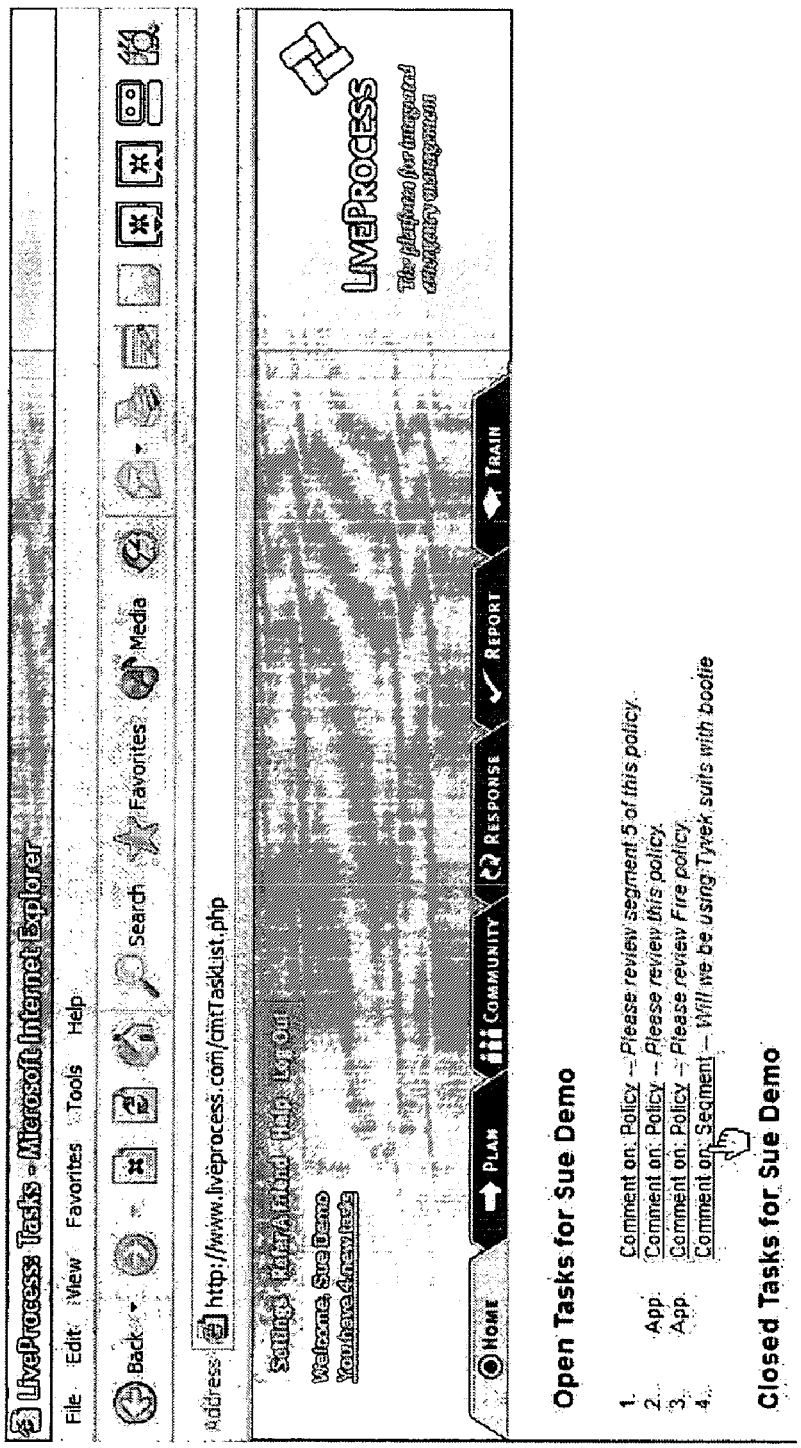

When a comment is posted on a policy, members of the selected committees receive an email indicating a comment has been made. When the committee members log into LiveProcess, they will be able to view the comment by clicking on "Your Task List." In the example shown in FIG. 13, a person named "Sue Demo" who is a member of the "Emergency Planning" committee has logged in and clicked on "Your Task List." She can now view a list of Tasks or Comments. A corresponding screenshot is shown in FIG. 32.

Figure 33:
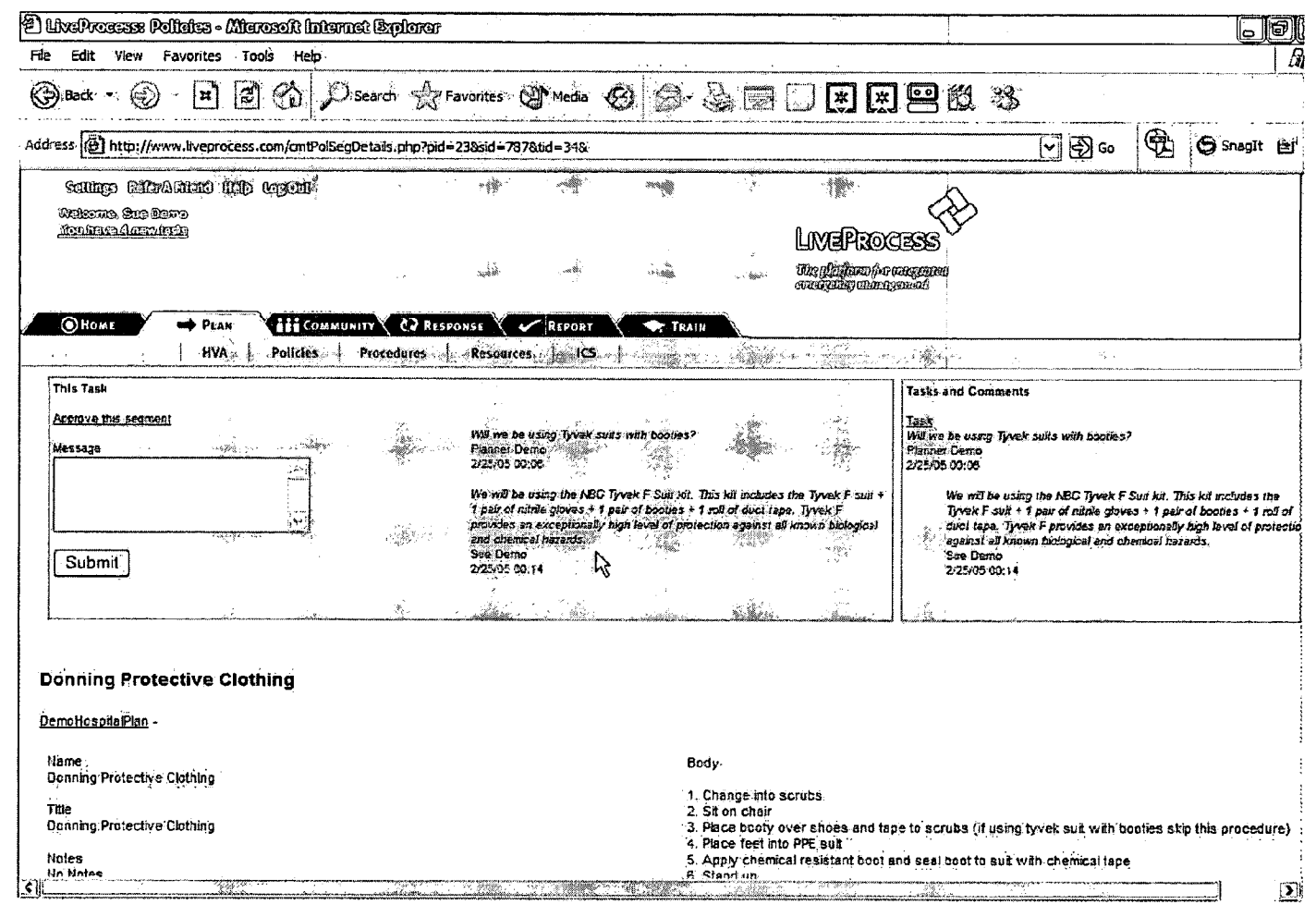

When "Sue Demo" clicks on a Comment title, she is taken to the "Comment page" where she can view the comment and respond to it by typing into the Message box and clicking "Submit." In the example shown in FIG. 14, "Sue Demo" has responded to the comment by indicating what type of Tyvek suit staff will be using. Every comment and response is time date stamped, so that a complete record of communication is kept for accrediting agencies such as JCAHO. A corresponding screenshot is shown in FIG. 33.

2.8 S8 Add a Procedure

2.8.1 Scenario Definition

The user would like to add a procedure to his emergency management plan.

2.8.2 Description

Figure 34:
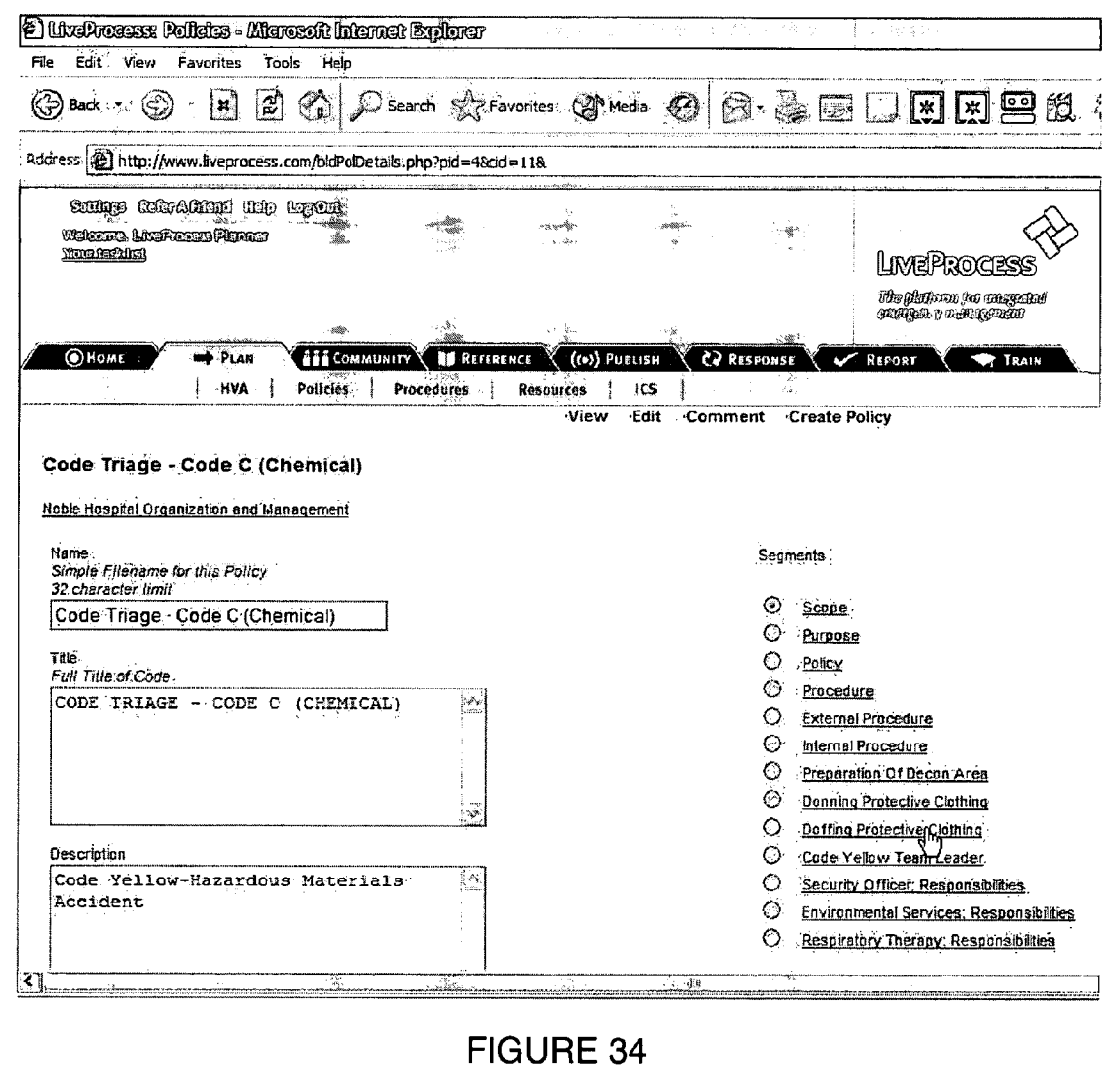
Figure 35:
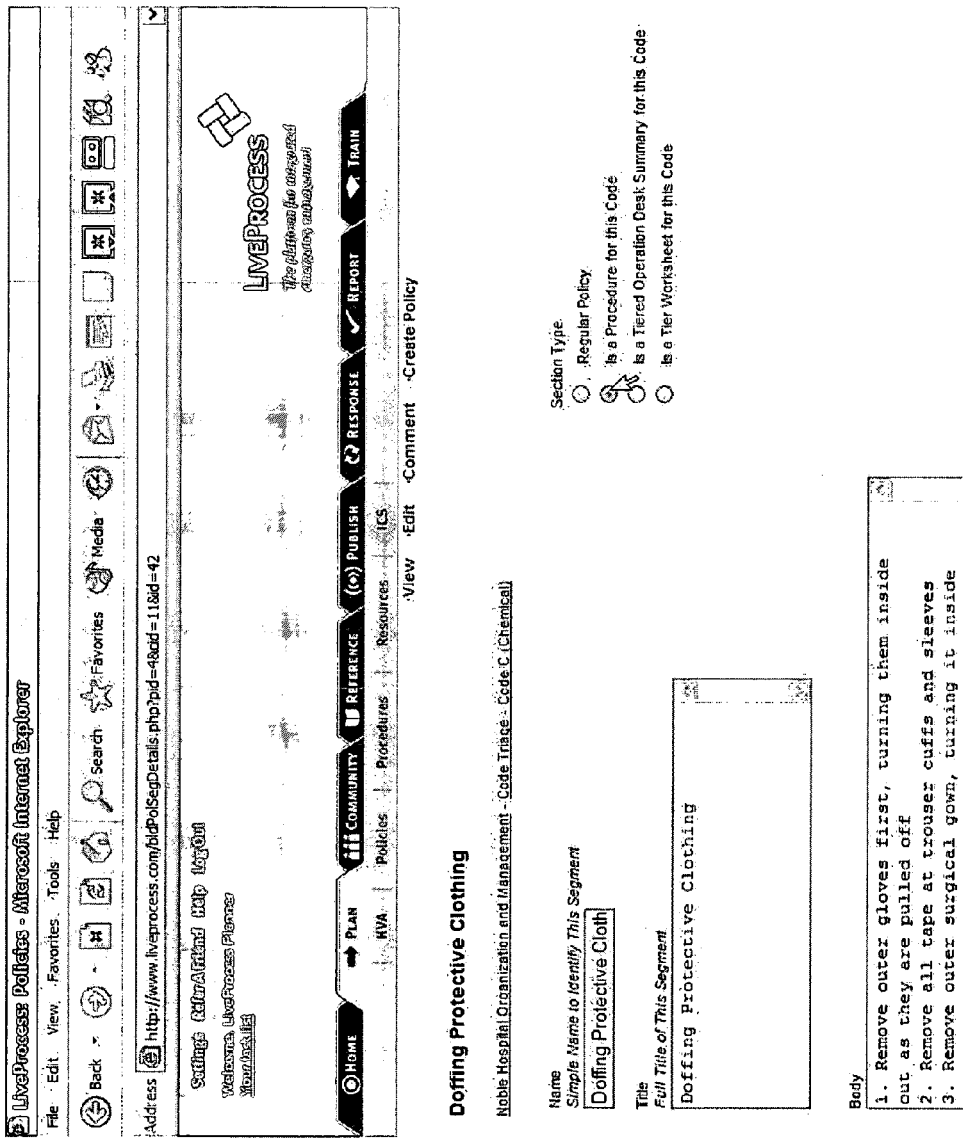
Figure 36:
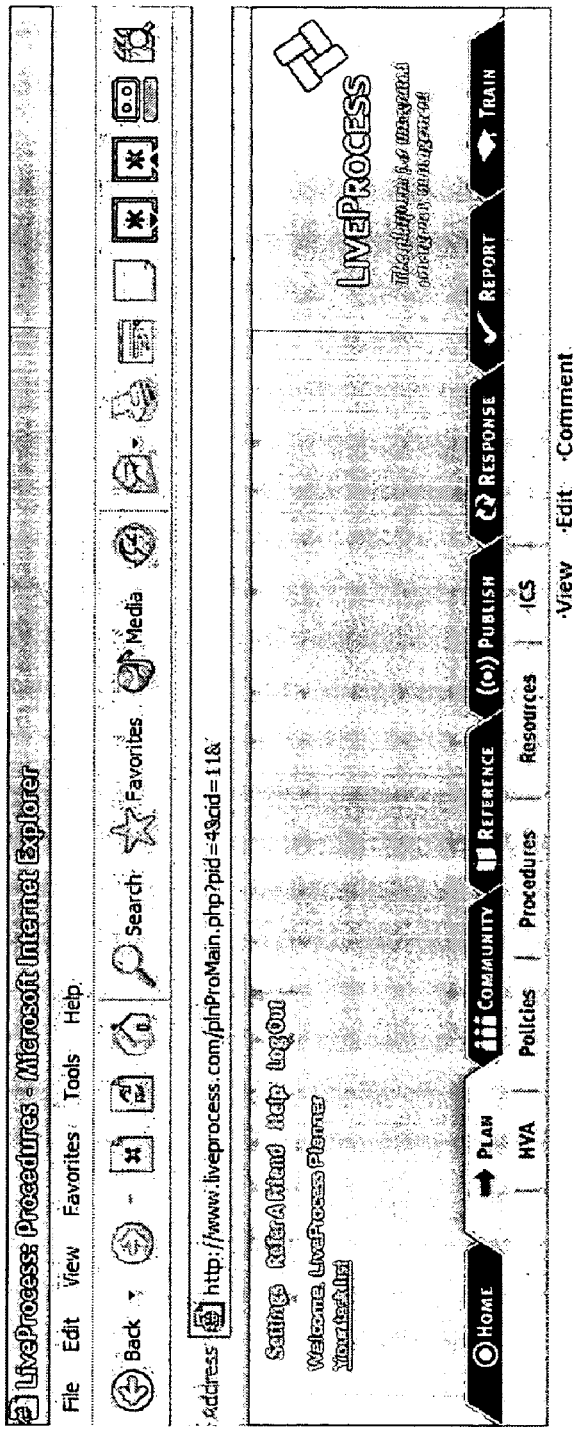

The user would like to quickly view and access the parts of his emergency plan policies that are procedures. This is done via the Procedures page. The user can add a procedure to this page by tagging it within his policies. To do this, the user would select the policy that contains the procedure, as shown in FIG. 15. The user would then put a check next to the option "Is a Procedure for this Code" as shown in FIG. 16. Corresponding screenshots are shown in FIGS. 34-35. After clicking Submit, the procedure selected will then appear on the Procedures page as show in FIG. 17. A corresponding screenshot is shown in FIG. 36.

2.9 S9 View HVA

2.9.1 Scenario Definition

A user wishes to view the HVA (Hazard Vulnerability Analysis) for his facility.

2.9.2 Description

A user would be able to view the HVA for his facility by clicking on the "PLAN" tab and then "HVA." This would display a standard Kaiser model of the facility's HVA as shown in FIG. 18. A corresponding screenshot is shown in FIG. 37.

2.10 S10 Create/Edit HVA

2.10.1 Scenario Definition

A user wishes to create or edit the HVA (Hazard Vulnerability Analysis) for his facility.

2.10.2 Description

A user would be able to create or edit the HVA for his facility by clicking on the "PLAN" tab, selecting "HVA," and then clicking either "Normal View" or "Expert View." Clicking "Normal View" presents the HVA in questionnaire format as shown in FIG. 19. Clicking on "Expert View" presents the HVA in grid format as shown in FIG. 20. Either format allows the user to edit the information. As soon as new data is entered and submitted, the "Risk" column in the HVA is automatically recalculated. Corresponding screenshots are shown in FIGS. 38-39.

2.11 S11 View Resources

2.11.1 Scenario Definition

A user wishes to view the resources available to his facility.

2.11.2 Description

Figure 40:
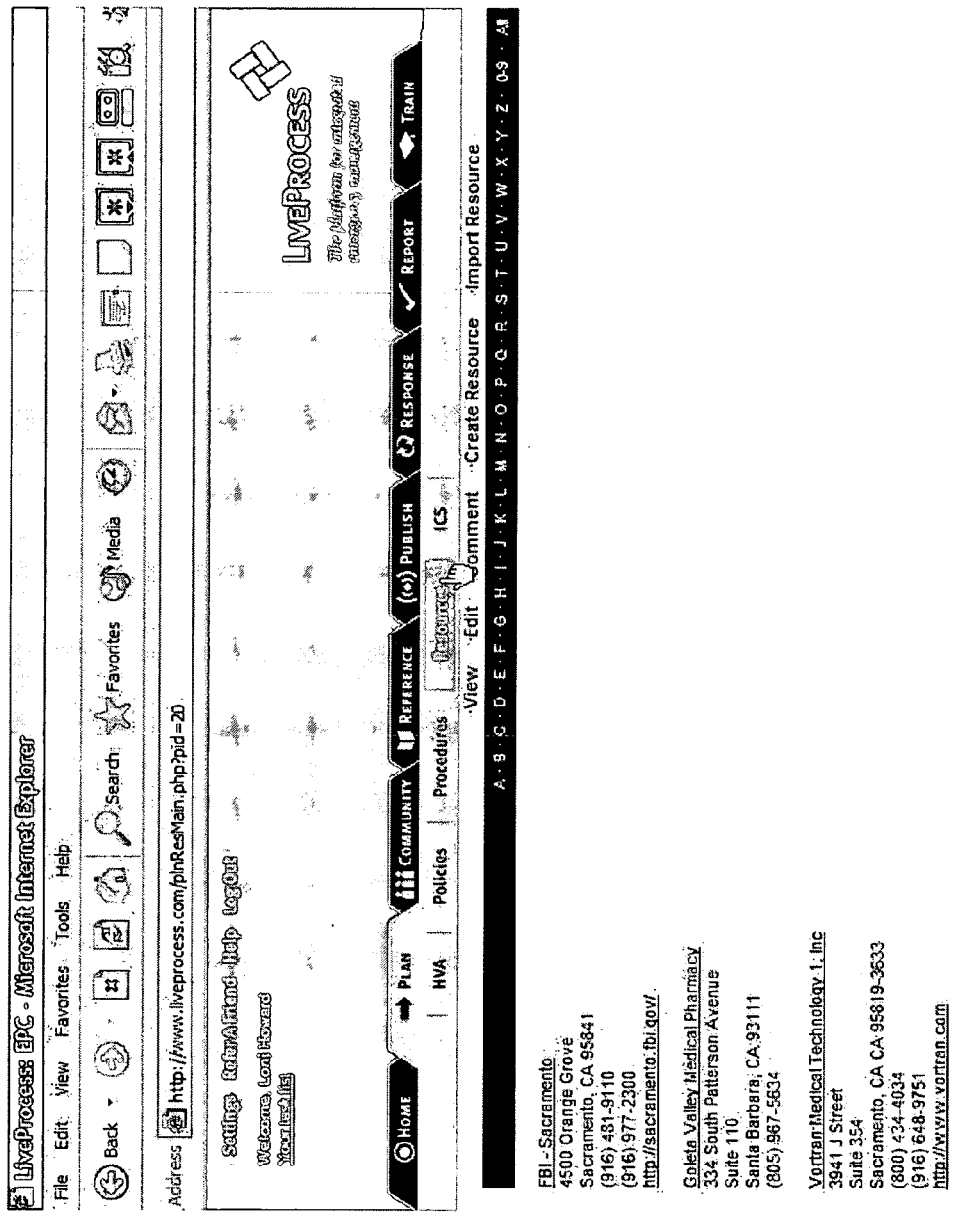

A user would be able to view the resources for his facility by clicking on the "PLAN" tab and then "Resources." This would display a list of all resources relevant to his facility, as shown in FIG. 21. The user can zoom in to resources beginning with a particular letter by clicking on the alphabet bar header at the top of the page. A corresponding screenshot is shown in FIG. 40.

2.12 S12 Create Resource

2.12.1 Scenario Definition

A user wishes to create or add new resources to the resource list in his plan.

2.12.2 Description

Figure 41:
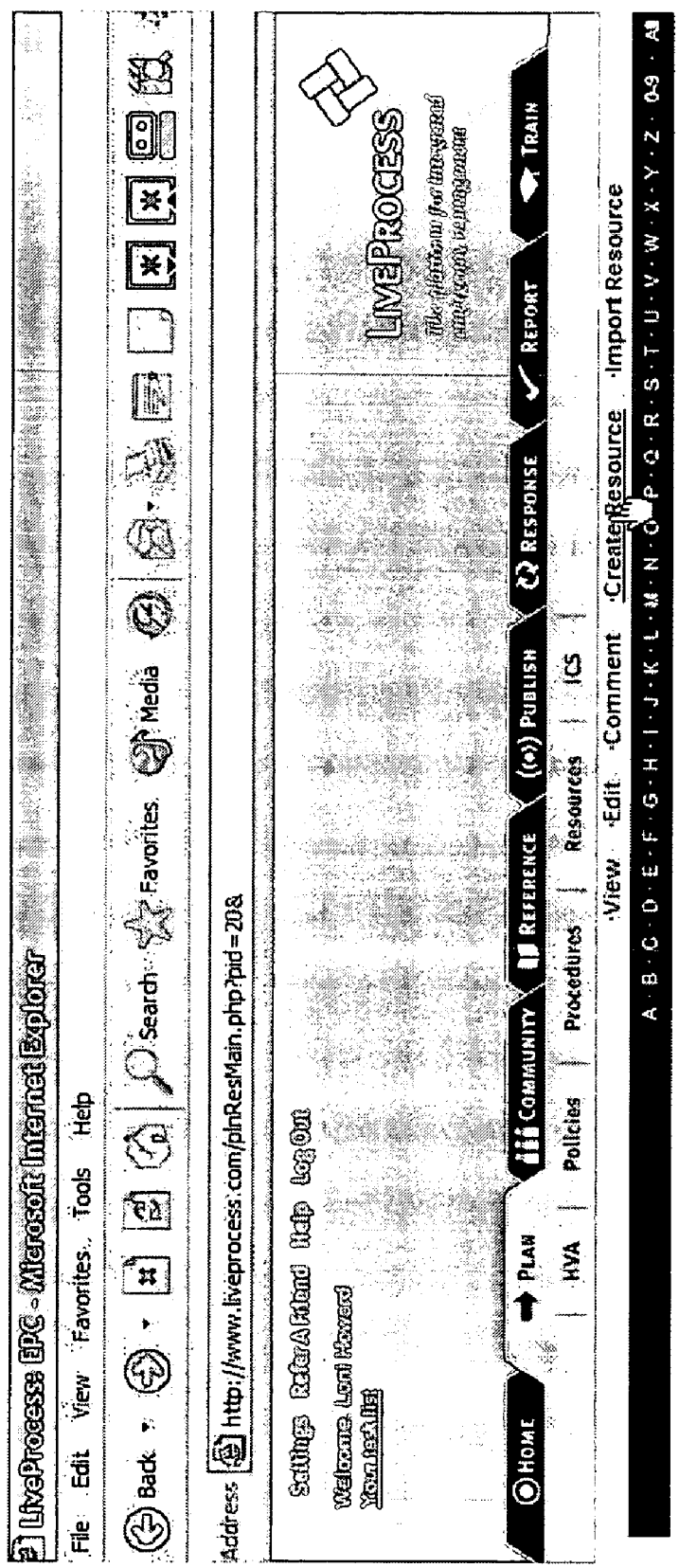
Figure 42:
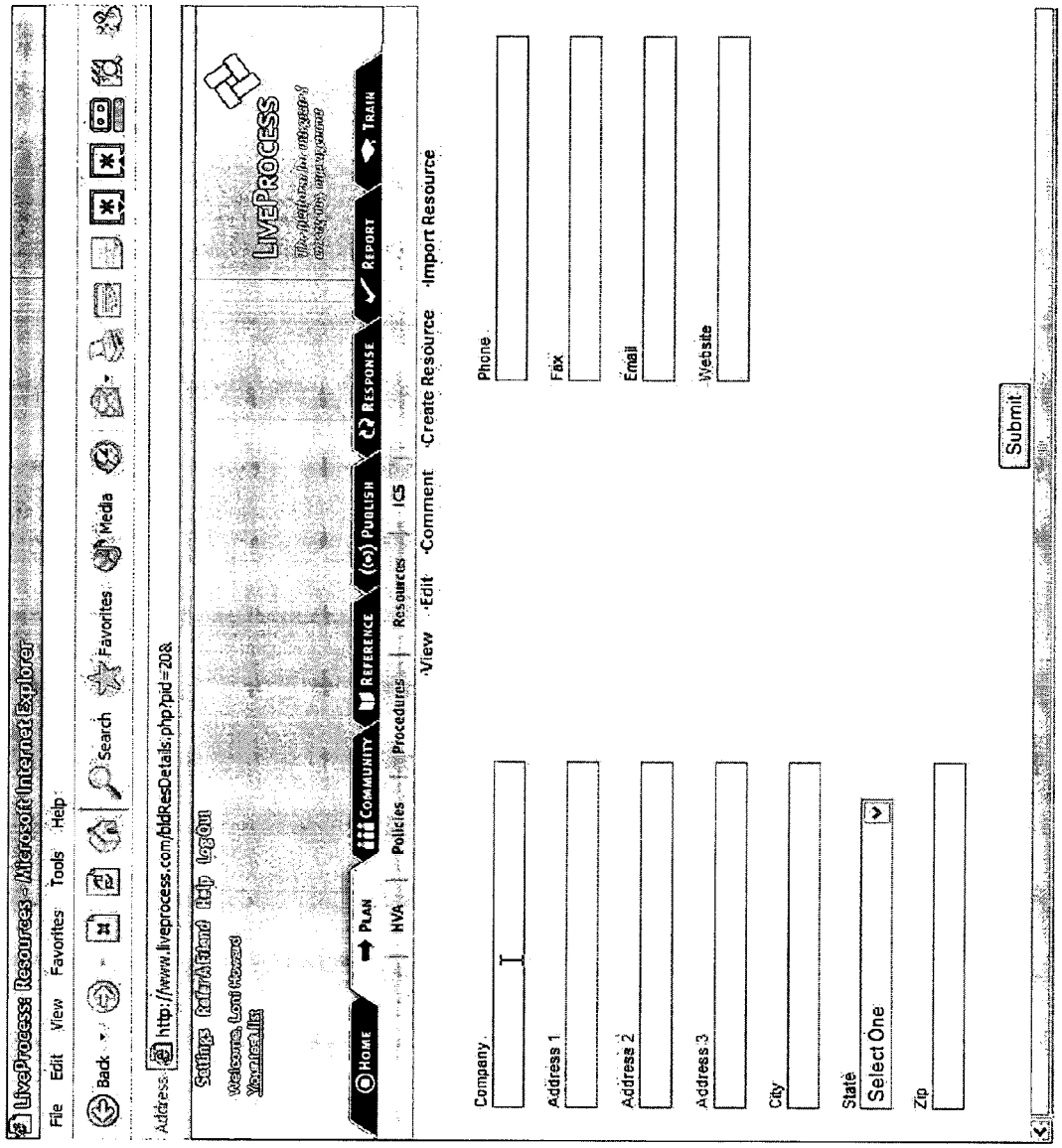

To add a new resource to his plan, the user would click on the PLAN tab, Resources, and then "Create Resource" as shown in FIG. 22. This would take him to the "Create Resource" page shown in FIG. 23, where he would enter the name, address, and contact info for the resource. Corresponding screenshots are shown in FIGS. 41-42.

2.13 S13 Import Resource

2.13.1 Scenario Definition

A user wishes to import a resource, from the existing LiveProcess database of resources, into his plan.

2.13.2 Description

Figure 43:
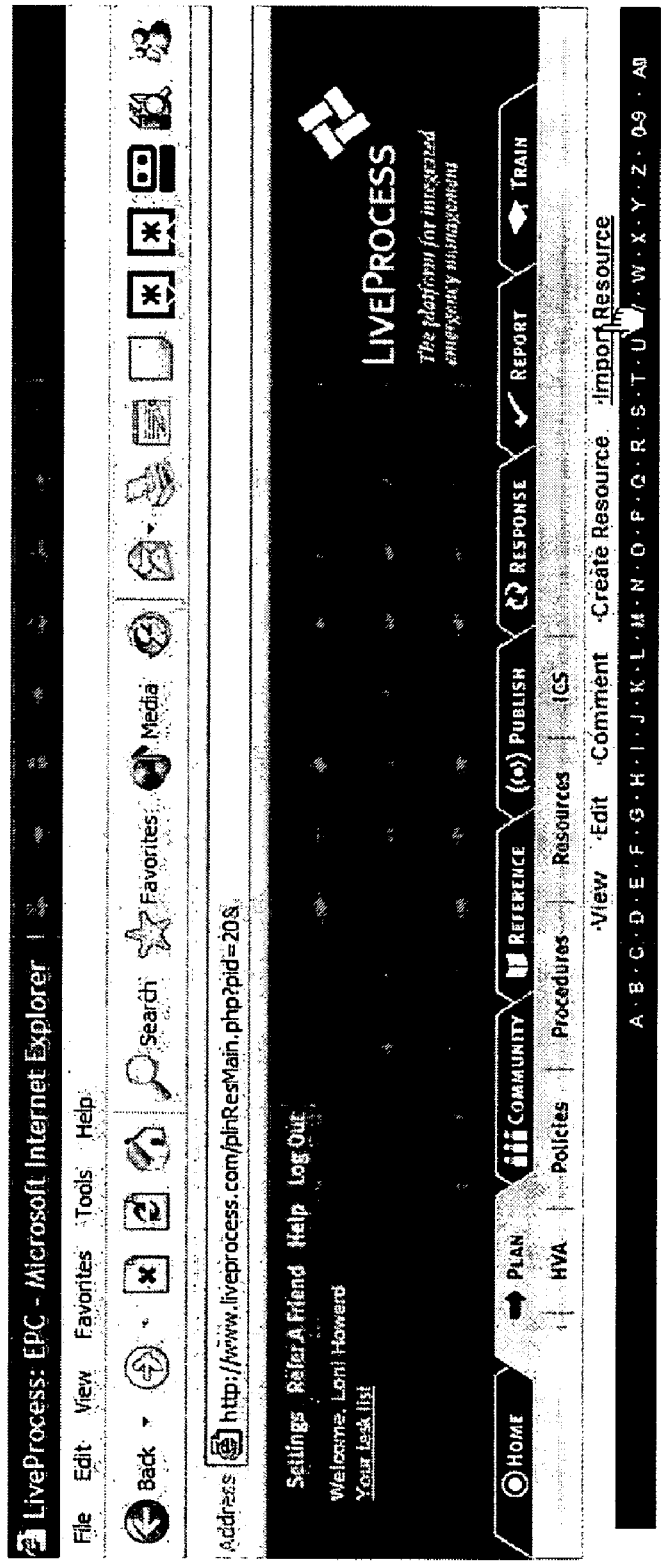

A user has the option to create his own resources or to import resources into his plan from the LiveProcess database of resources. To import a resource, he would click on the PLAN tab>Resources>Import a Resource, as shown in FIG. 24. A corresponding screenshot is shown in FIG. 43.

Figure 44:
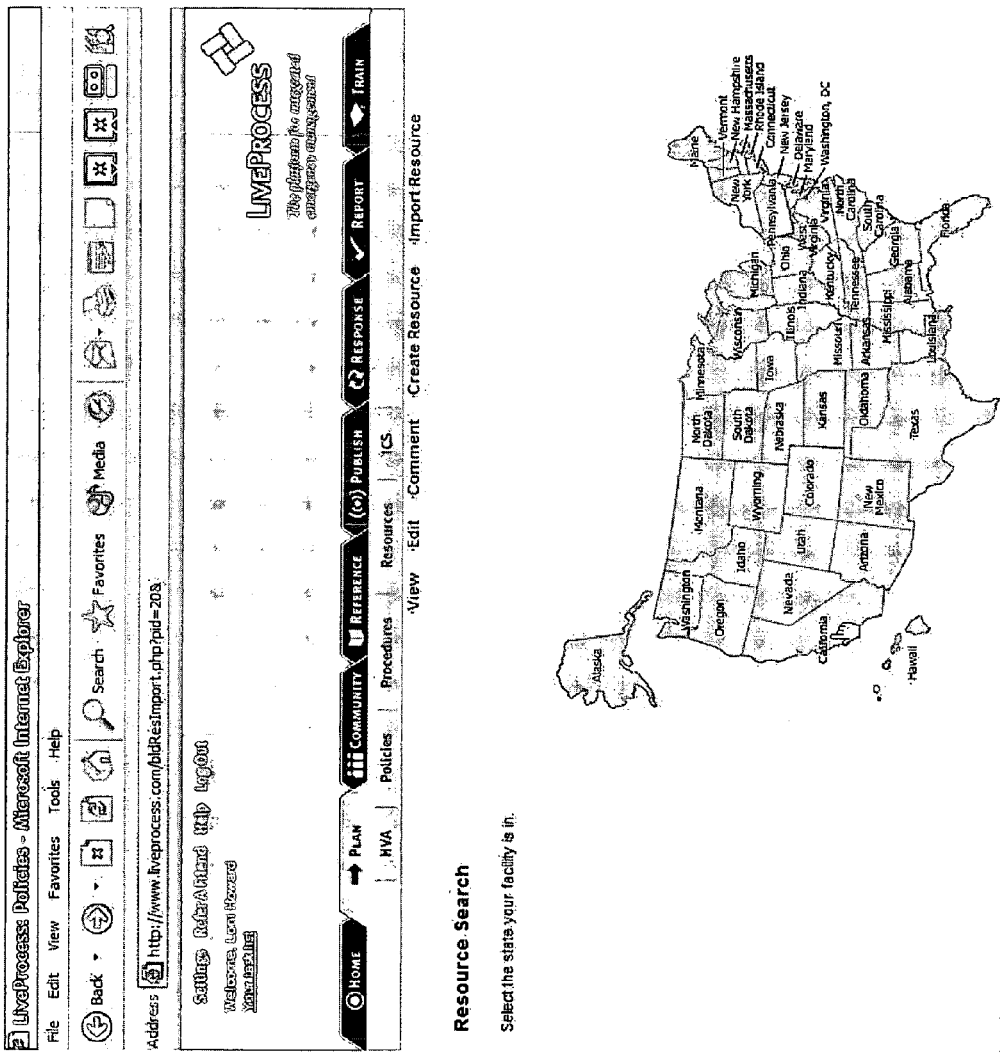

After clicking on "Import Resource," the user is taken to the "Resource Search" page, shown in FIG. 25. From here, he would click on the state in which he would like to locate an import a resource. A corresponding screenshot is shown in FIG. 44.

Figure 45:
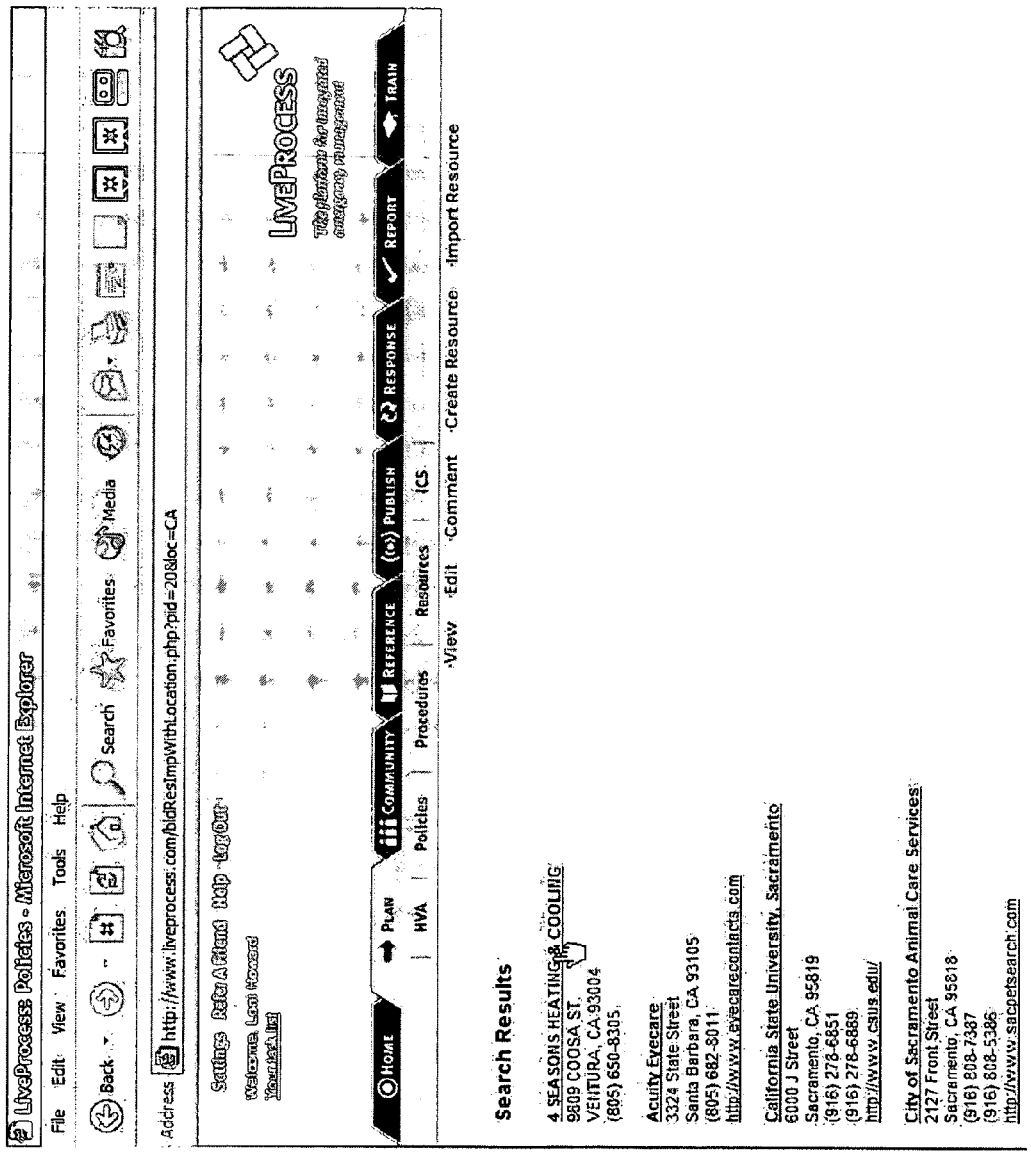

For example, if the user clicked on California, the "Search Results" page, shown in FIG. 26, would display all the California resources available in the LiveProcess Resource Database. From there, the user would simply click on a resource to add it to his plan. A corresponding screenshot is shown in FIG. 45.

2.14 S14 Create EPC

2.14.1 Scenario Definition

A user wishes to set up his emergency planning committees (EPC) in LiveProcess so that he can submit plans for review and approval.

2.14.2 Description

Figure 46:
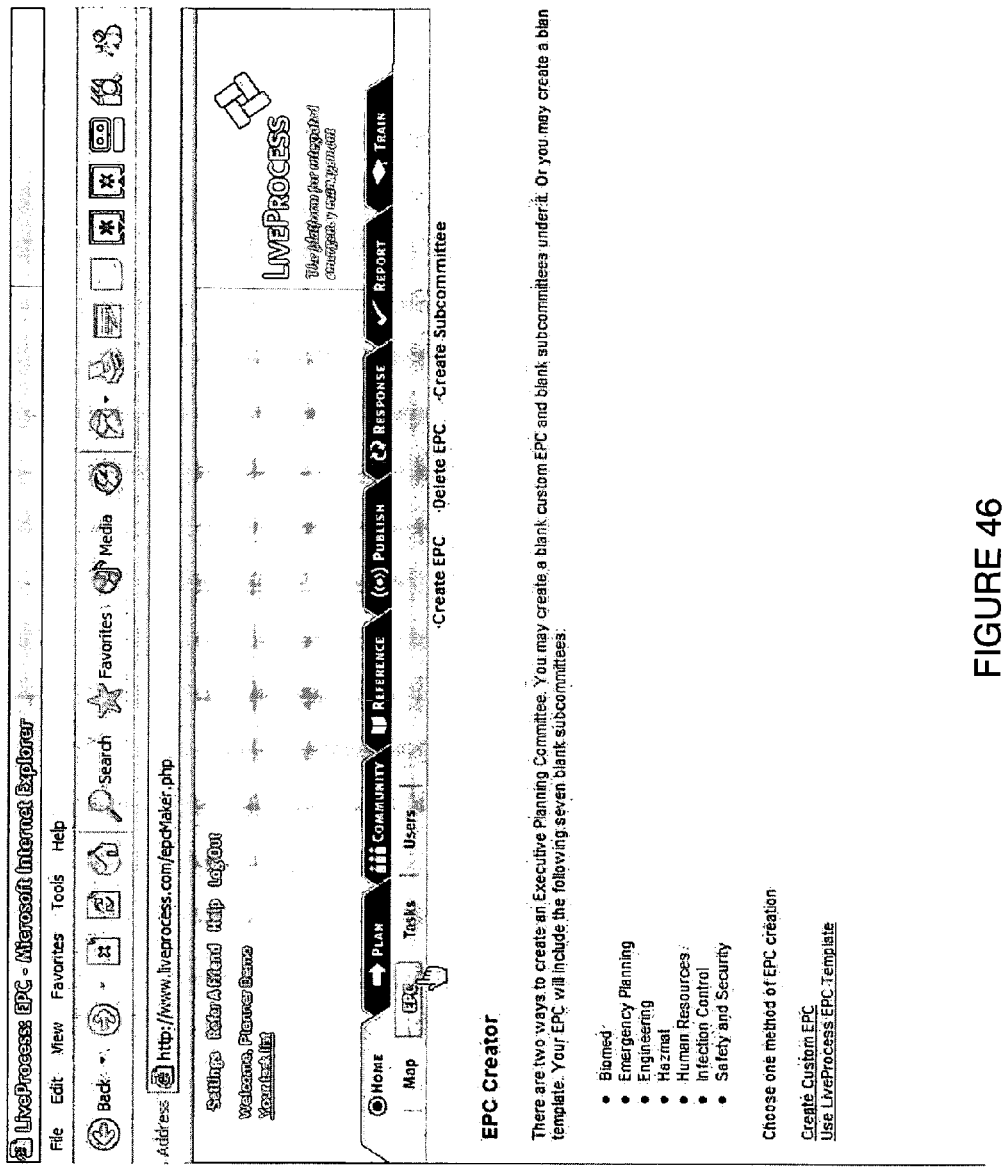

A user is able to set up his EPCs by clicking on HOME>EPC. This takes him to the EPC Creator page shown in FIG. 27. From here the user has two options, he can use the LiveProcess EPC template, which automatically sets up 7 blank committees, or he can create a custom EPC. A corresponding screenshot is shown in FIG. 46.

Figure 47:
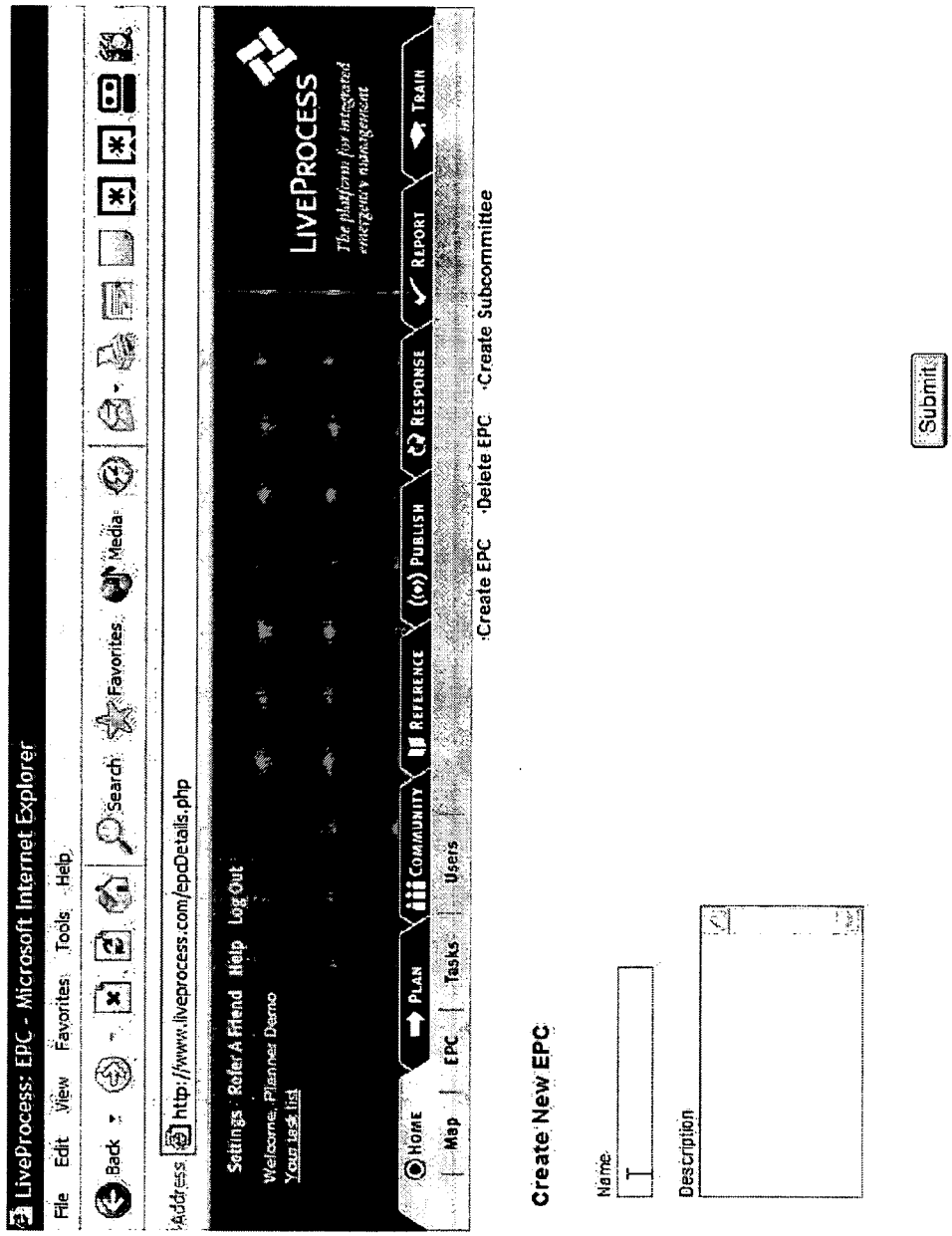

If the user chooses "Custom EPC," he is presented with the "Create New EPC" page shown in FIG. 28. A corresponding screenshot is shown in FIG. 47.

2.15 S15 Edit EPC

2.15.1 Scenario Definition

A user wishes to edit his emergency planning committees (EPC) in LiveProcess. For example, he may want to remove some people from an EPC.

2.15.2 Description

Figure 48:
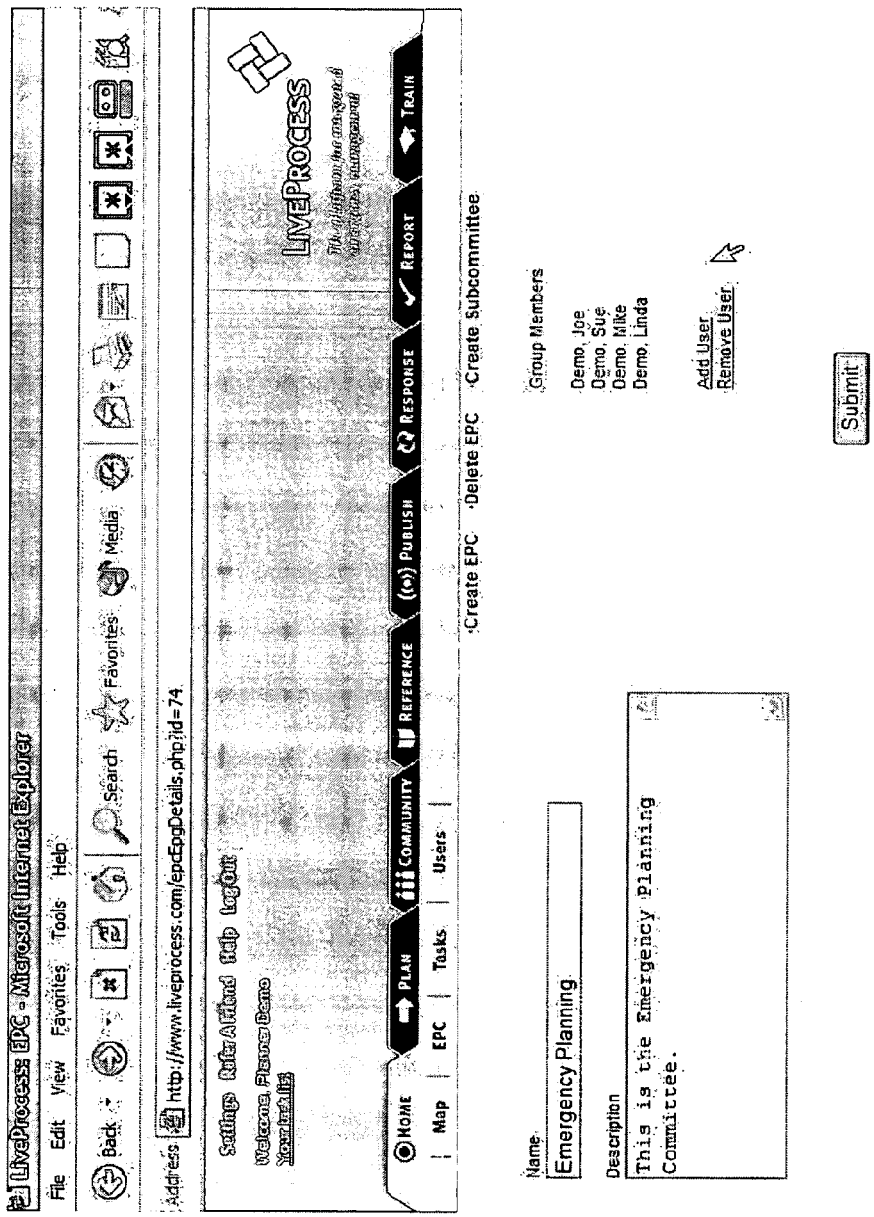

To edit an EPC, the user would click on HOME>EPC and then click on the title of the committee he would like to change. This brings up the page shown in FIG. 29. From here, he can choose to "Add User" or "Remove User." A corresponding screenshot is shown in FIG. 48.

Figure 49:
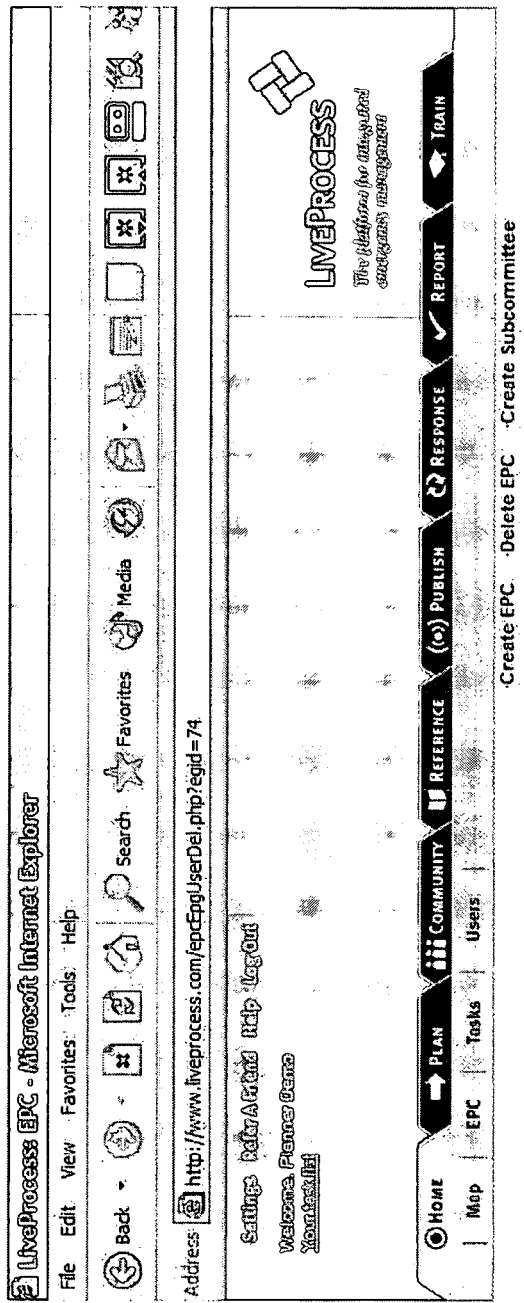

If the User clicks on "Remove User," he is taken to the page shown in FIG. 30. From here, he simply clicks on the name of the user he would like to remove. A corresponding screenshot is shown in FIG. 49.

2.16 S16 Map of Region

2.16.1 Scenario Definition

A user wishes to view a map showing his facility and local region.

2.16.2 Description

Figure 50:
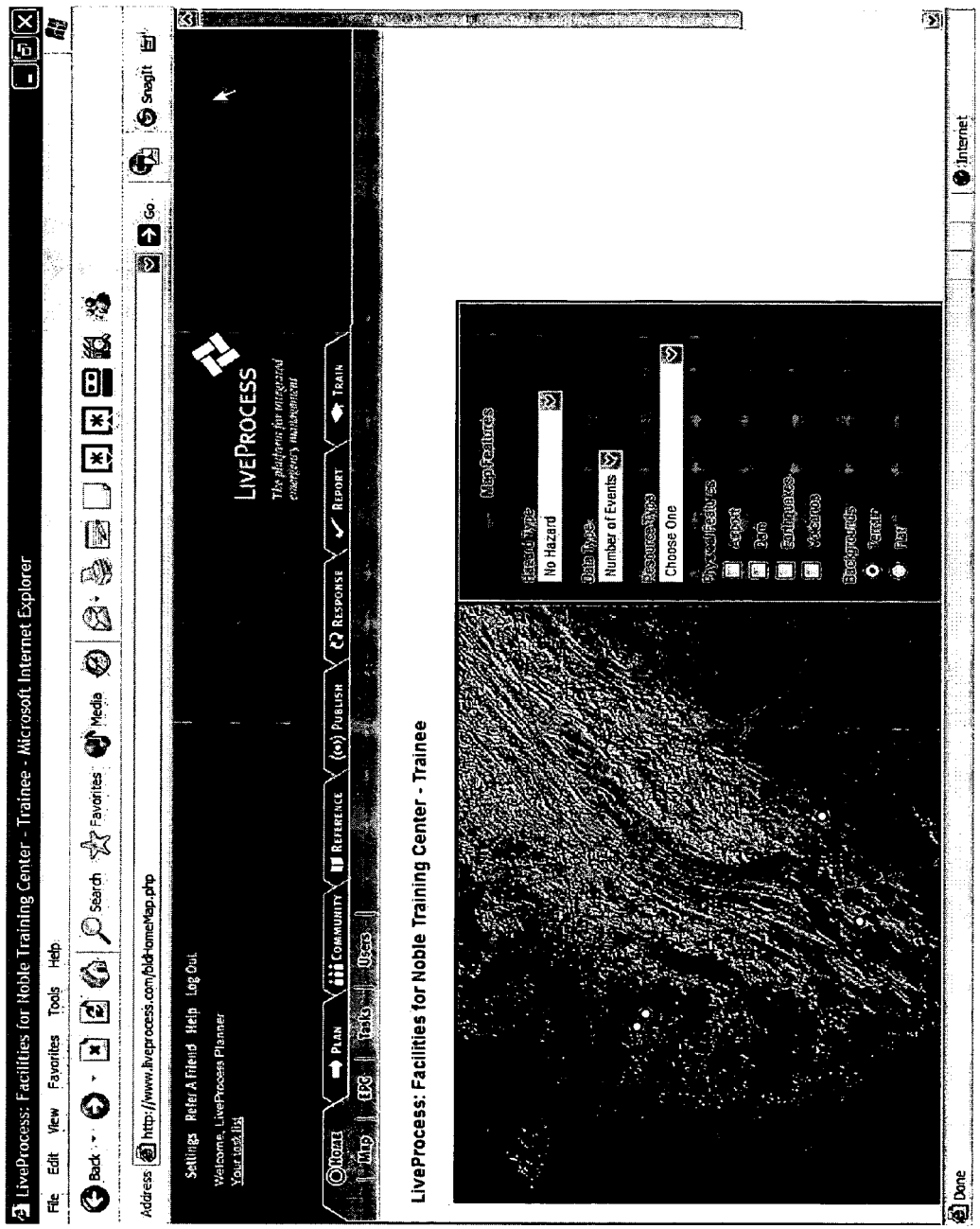

To view a map showing his facility and local region, the user would click on HOME>Map. He would automatically be shown a map specific to his region, as shown in FIG. 31. This is based on his login. A corresponding screenshot is shown in FIG. 50.

2.17 S17 Mapping Hazards

2.17.1 Scenario Definition

A user wishes to have a visual way to assess which hazard types pose a risk in a particular region or across the United States.

2.17.2 Description

Figure 51:
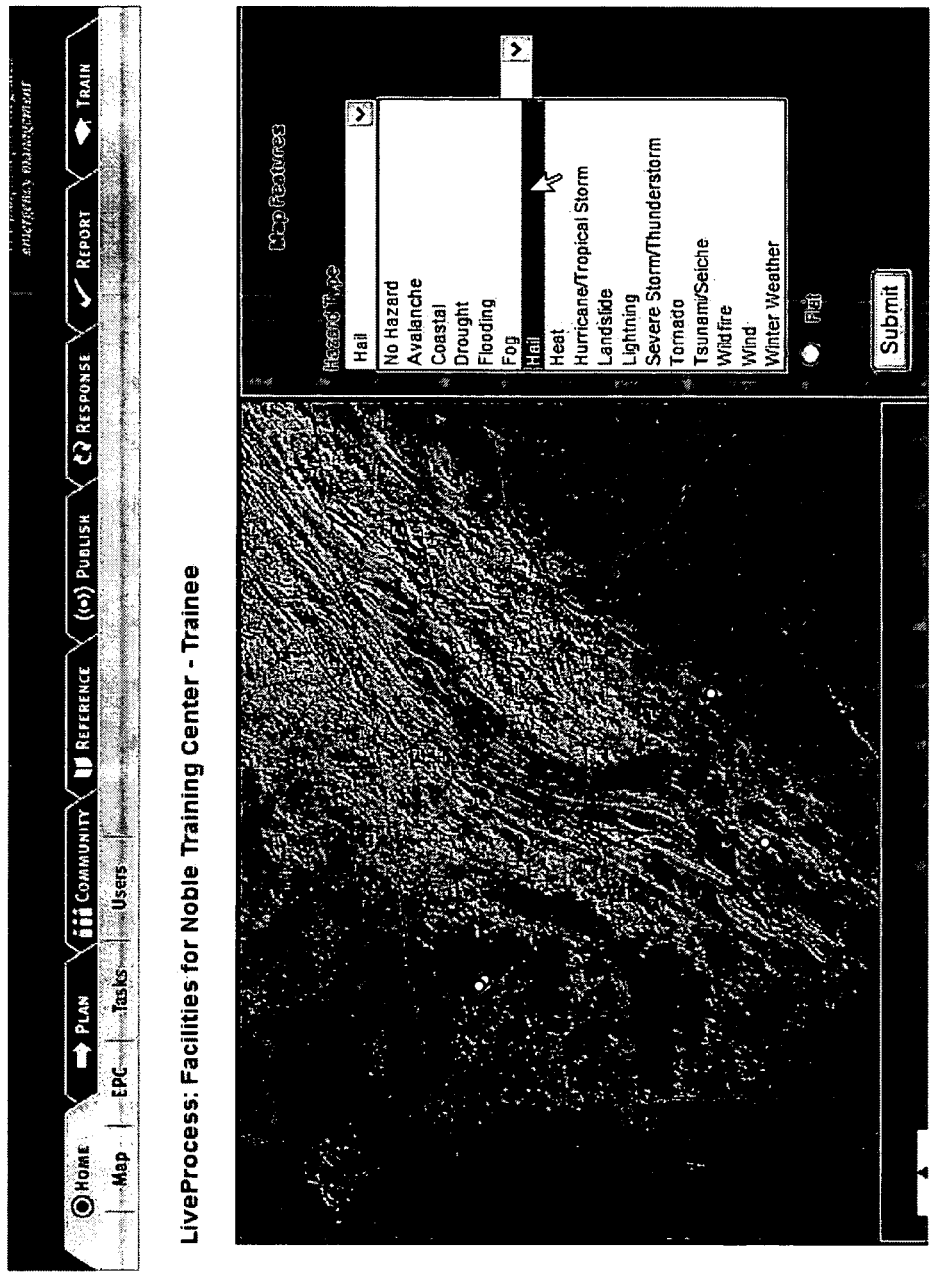

A user may gather historical hazard incident data by using the GIS MAP located on the HOME tab of LiveProcess. For example, the user could select "hail" from the "Hazard Type" picklist as shown in FIG. 32. A corresponding screenshot is shown in FIG. 51.

After selecting "Hail" as Hazard Type and "Number of Events" as Data Type, the user would click "Submit." The map would then automatically change to a color-coded display indicating the incidence of hail throughout the region, as shown in FIG. 33. (Red=High, Orange=Moderate, Yellow=Low) A corresponding screenshot is shown in FIG. 52.

2.18 S18 Mapping Resource Types

2.18.1 Scenario Definition

A user wishes to have a visual way to view the types of resources located in a particular region or across the United States.

2.18.2 Description

A user may gather info on available resources by using the GIS MAP located on the HOME tab of LiveProcess. As shown in FIG. 34, the "Resource Type" picklist contains options such as Fire Depts., Pharmaceuticals, Ventilators, and Water. A corresponding screenshot is shown in FIG. 53.

2.19 S19 ICS View

2.19.1 Scenario Definition

A user wishes to view the ICS (Incident Command System) or HEICS (Hospital Incident Command System) structure used by his facility. This includes a listing of all roles and associated responsibilities.

2.19.2 Description

Figure 54:
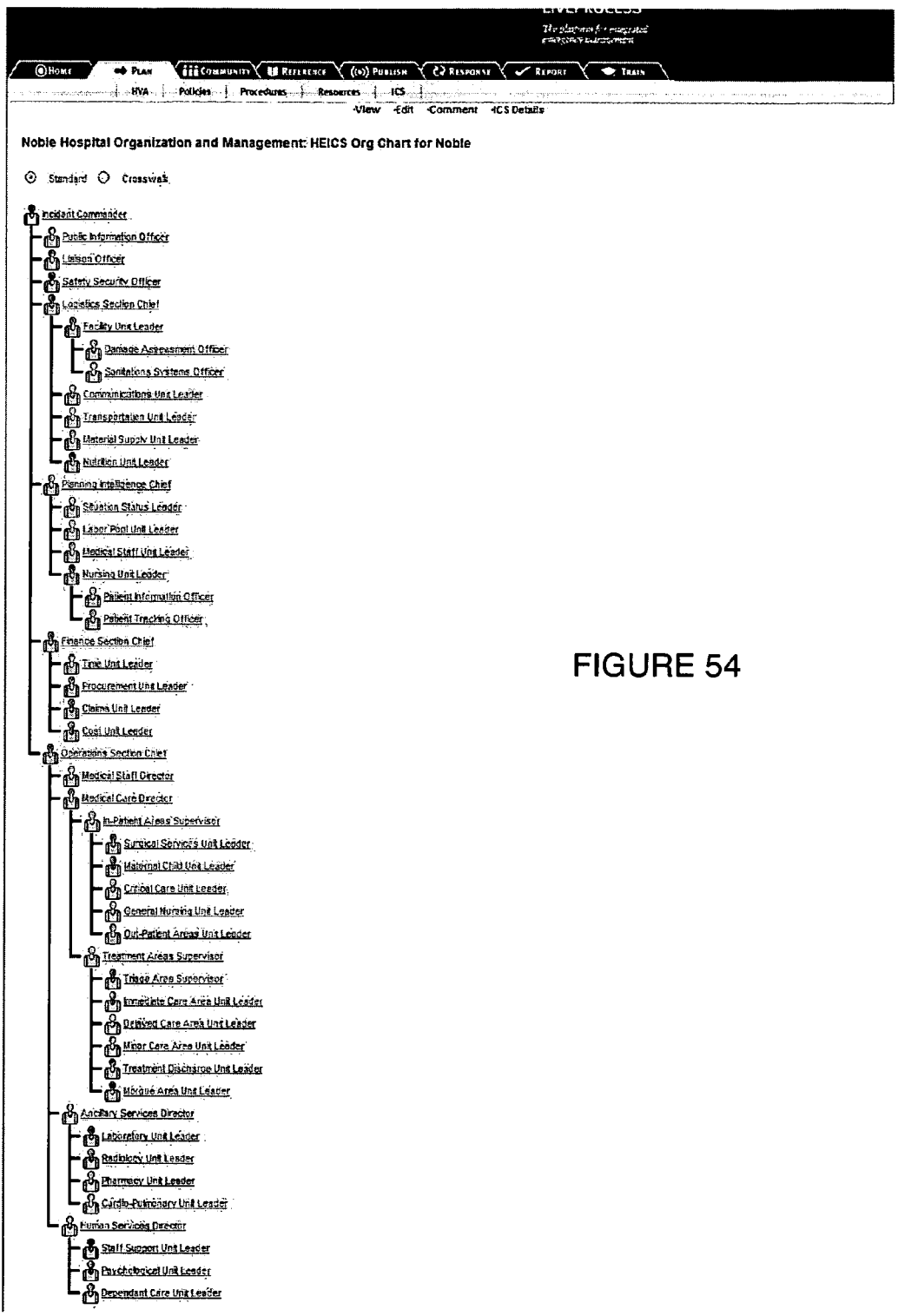

To view the ICS structure for his facility, the user would click on the PLAN tab, select a plan, and then click on ICS. This would bring up a page displaying all 49 of the standard HEICS roles. The standard view, shown in FIG. 35, displays each position title. The Crosswalk view, shown in FIG. 36, displays each position title and the name of the person assigned to the position. Corresponding screenshots are shown in FIGS. 54-55.

2.20 S20 ICS Job Action Sheet

2.20.1 Scenario Definition

A user wishes to view the job action sheet (JAS) associated with a specific role in the incident command system (ICS).

2.20.2 Description

Figure 56:
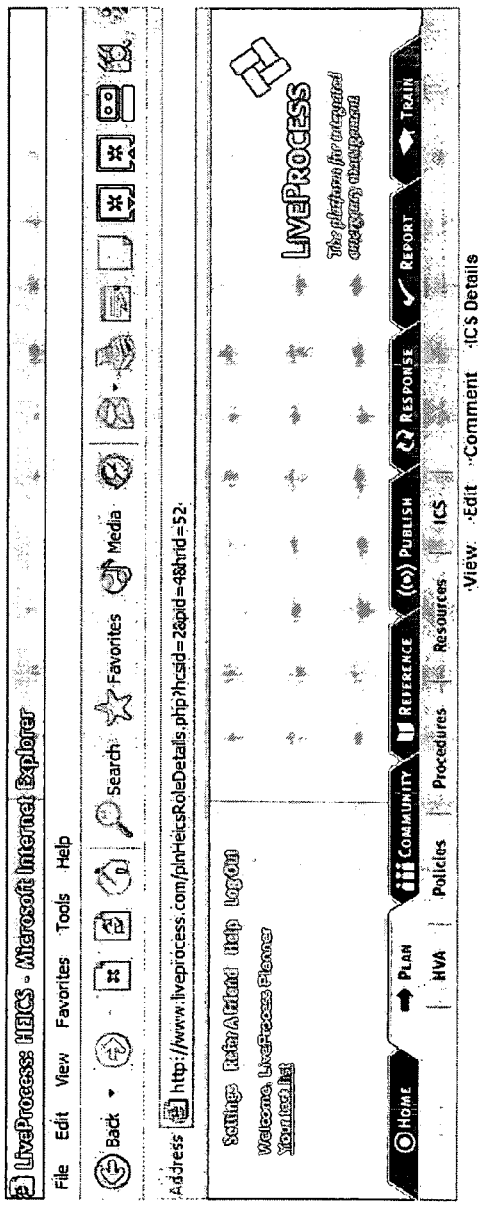

To view role-specific job action sheets, the user would click on ICS, and then click on one of the 49 position titles. If a JAS has already been created, this would bring up the role details page, shown in FIG. 37. From there, the user would click on the link under "Job Action Sheets." This would automatically open a new web browser displaying the Job Action Sheet, shown in FIG. 38. Corresponding screenshots are shown in FIGS. 56-57.

As shown in FIG. 38, the Job Action Sheet autofills in the name of the person who has been assigned the position. If there is a "Reports to" person, that name will be autofilled in as well, based on assignments made by the user.

2.21 S21 ICS Custom Job Action Sheet 2.21.1 Scenario Definition

A user wishes to create a custom job action sheet for a specific role in the incident command system (ICS).

2.21.2 Description

Figure 58:
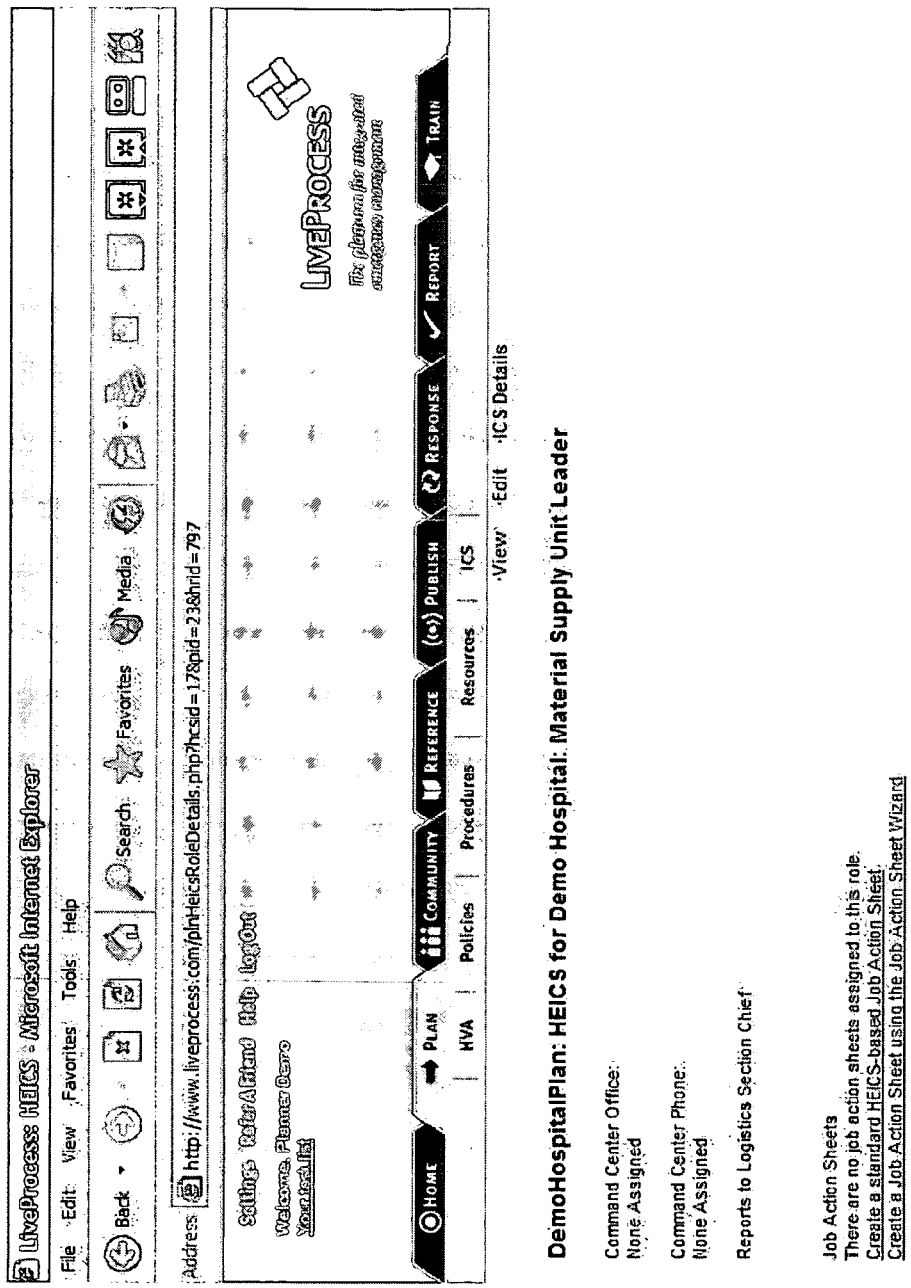

To create a custom job action sheets, the user would click on ICS, and then click on one of the 49 position titles. If no JAS has been created yet for the role, this would bring up the role details page, shown in FIG. 39. From there, the user has the choice to either "Create a standard HEICS-based Job Action Sheet" or "Create a Job Action Sheet using the Job Action Sheet Wizard." A corresponding screenshot is shown in FIG. 58.

2.22 S22 ICS Forms 2.22.1 Scenario Definition

A user wishes to view the standard forms associated with a specific role in the incident command system (ICS).

2.22.2 Description

Figure 59:
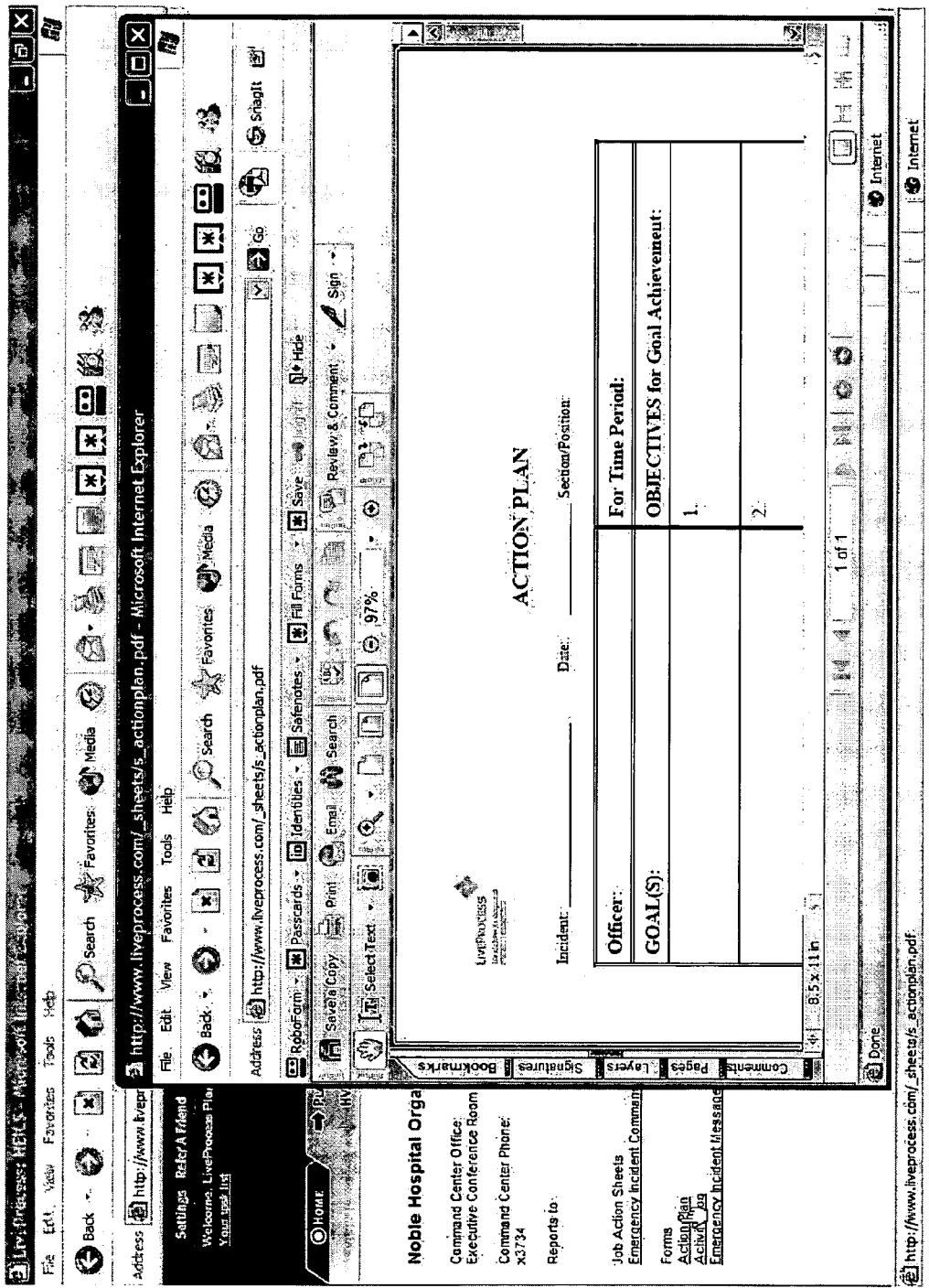
Figure 63:
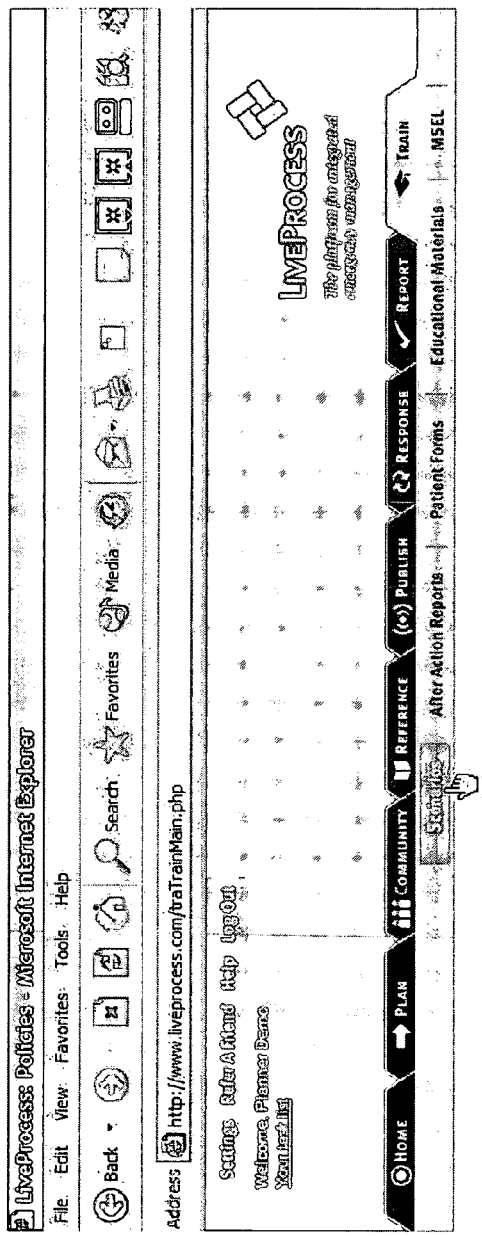
Figure 64:
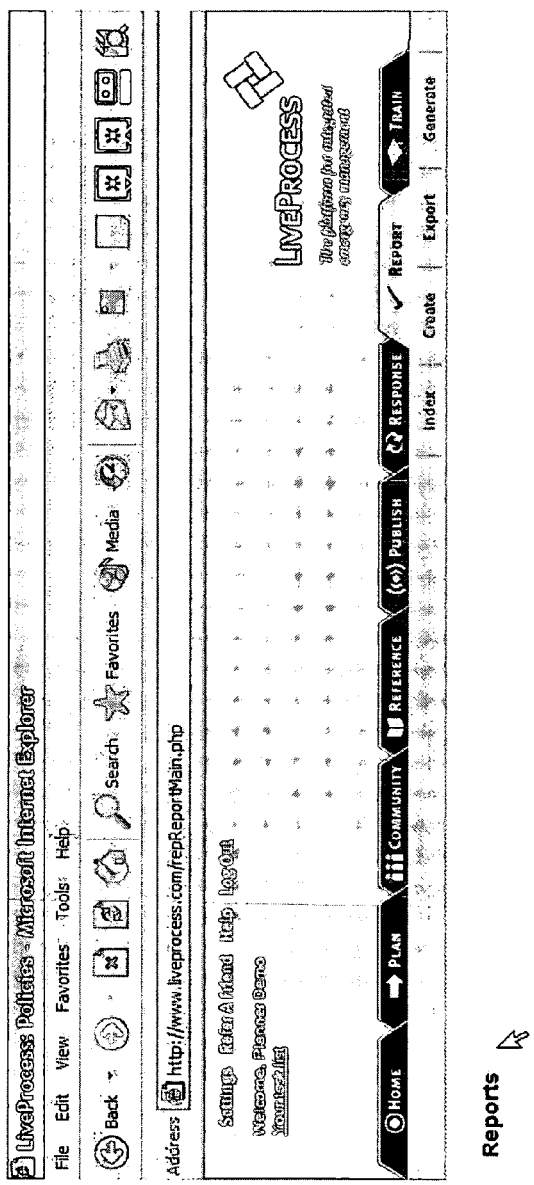

To view the standard HEICS forms associated with a role, the user would click on the links located under "Forms" on the role detail page. This would automatically open a new web page displaying the selected form, as shown in FIG. 40. A corresponding screenshot is shown in FIG. 59.

2.23 S23 Community 2.23.1 Scenario Definition

A user wishes to communicate with other emergency management professionals in a secure online forum.

2.23.2 Description

To communicate with other members of the LiveProcess community, the user would click on the Community tab. This would display the Community page shown in FIG. 41. In Community, the user can access various online discussion forums. The user may post comments, polls, file attachments, and links in the online discussion forums. A corresponding screenshot is shown in FIG. 60.

2.24 S24 Reference 2.24.1 Scenario Definition

A user wishes to search and view reference materials provided by other emergency management professionals.

2.24.2 Description

To search and view reference materials posted by other LiveProcess members, the user would click on the REFERENCE tab and type keywords into the search box. In the example shown in FIG. 42, the user has done a search on the keyword "decon." To view one of the documents, the user would click "Import" and then choose to open or save the document to his computer. The Reference area contains many different file types, including MS Word docs, Excel files, PowerPoint presentations, and PDFs. A corresponding screenshot is shown in FIG. 61.

2.25 S25 Publish 2.25.1 Scenario Definition

A user wishes to publish reference materials so that they can be accessed by other emergency management professionals.

2.25.2 Description

To publish reference materials so that other LiveProcess members may access them, the user would click on the PUBLISH tab, fill in the brief form describing the material, and then upload the file from his computer. The user may publish many different file types, including MS Word docs, Excel files, PowerPoint presentations, and PDFs. A corresponding screenshot is shown in FIG. 62.

One preferred embodiment of the present invention is implemented via the source code in the accompanying Appendix.

The present invention may be implemented with any combination of hardware and software. If implemented as a computer-implemented apparatus, the present present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A computer-implemented method of providing emergency plans for a plurality of different facilities, wherein each of the facilities are entities that implement their respective emergency plans, when necessary, the method comprising:

(a) providing in electronic form an emergency plan for each facility, each emergency plan having a standardized format with a plurality of component parts, each emergency plan having at least some component parts that are accessible by other facilities, wherein the plurality of component parts includes at least one of a Hazard Vulnerability Analysis, emergency policies, procedures that must be followed, available emergency resources, and an Incident Command System command structure;

(b) providing an electronic network which allows the plurality of different facilities to communicate with each other;

(c) at least some of the facilities using the electronic network to electronically share one or more accessible component parts of the emergency plans of at least some of the other facilities with each other, wherein the electronic sharing is a sharing of at least one of the Hazard Vulnerability Analysis, emergency policies, procedures that must be followed, available emergency resources, and an Incident Command System command structure;

(d) electronically importing selected content of the electronically shared one or more accessible component parts of the emergency plan of another facility into one or more component parts of the emergency plans of facilities that received the electronically shared component parts, wherein the electronic importing is facilitated via the use of the standardized format for the emergency plans, and wherein the electronically imported content becomes part of the emergency plans of the facilities that received the electronically shared component parts;

(e) one or more third-party entities electronically publishing information for incorporation into emergency plans of selected facilities; and (f) at least some of the facilities being programmed to receive the published information and to electronically import and incorporate the published information into their respective emergency plans via the electronic network.

2. The method of claim 1 wherein one of the component parts of the emergency plan includes emergency policies, and step (c) further comprises:

(i) entering one or more search terms into a user interface, (ii) via the electronic network, searching emergency plans of other facilities that contain the entered one or more search terms, and (iii) displaying the search hits, and step (d) further comprises electronically importing the emergency policy of a desired search hit into the emergency plan of the facility.

3. The method of claim 2 wherein the search term is related to an emergency condition, and the imported emergency policy relates to the emergency condition.

4. The method of claim 1 wherein the electronic network is the internet or an intranet and the user interface is accessed via an internet web browser.

5. The method of claim 1 wherein the plurality of component parts include emergency drill procedures.

6. The method of claim 1 wherein textual material of an emergency plan constitutes the plan's policies, and one of the component parts of the emergency plan are the emergency plan procedures, the method further comprising:

(g) providing a user interface that allows sections of policies to be labeled as procedures, the user interface also allowing all previously identified procedures to be shown on a single listing for rapid review.

7. The method of claim 1 wherein a facility is a single facility entity.

8. The method of claim 1 wherein a facility is a network of related facility entities.

9. The method of claim 1 further comprising:

(g) providing via the electronic network a geographic information system (GIS) data set; and (h) projecting facility data onto the GIS data set, the facility data including the plurality of component parts of each emergency plan, wherein in step (c), the accessible component parts of the emergency plans are electronically shared by using the GIS data set that has the facility data projected thereon.

10. The method of claim 1 wherein one of the component parts of the emergency plan includes emergency policies, and the method further comprises:

(g) each facility designating which emergency policies in their respective emergency plans are accessible to other facilities, wherein only emergency policies that are designated as being accessible to other facilities can be electronically shared and imported into another facility.

11. The method of claim 1 wherein the electronic sharing is an electronic exchanging among facilities.

12. An article of manufacture for providing emergency plans for a plurality of different facilities, wherein each of the facilities are entities that implement their respective emergency plans, when necessary, the article of manufacture comprising a computer-readable medium holding computer-executable instructions for performing a method comprising:

(a) providing in electronic form an emergency plan for each facility, each emergency plan having a standardized format with a plurality of component parts, each emergency plan having at least some component parts that are accessible by other facilities, wherein the plurality of component parts includes at least one of a Hazard Vulnerability Analysis, emergency policies, procedures that must be followed, available emergency resources, and an Incident Command System command structure;

(b) providing an electronic network which allows the plurality of different facilities to communicate with each other;

(c) at least some of the facilities using the electronic network to electronically share one or more accessible component parts of the emergency plans of at least some of the other facilities with each other, wherein the electronic sharing is a sharing of at least one of the Hazard Vulnerability Analysis, emergency policies, procedures that must be followed, available emergency resources, and an Incident Command System command structure;

(d) electronically importing selected content of the electronically shared one or more accessible component parts of the emergency plan of another facility into one or more component parts of the emergency plans of facilities that received the electronically shared component parts, wherein the electronic importing is facilitated via the use of the standardized format for the emergency plans, and wherein the electronically imported content becomes part of the emergency plans of the facilities that received the electronically shared component parts;

(e) one or more third-party entities electronically publishing information for incorporation into emergency plans of selected facilities; and (f) at least some of the facilities being programmed to receive the published information and to electronically import and incorporate the published information into their respective emergency plans via the electronic network.

13. The article of manufacture of claim 12 wherein one of the component parts of the emergency plan includes emergency policies, and step (c) further comprises:

(i) entering one or more search terms into a user interface, (ii) via the electronic network, searching emergency plans of other facilities that contain the entered one or more search terms, and (iii) displaying the search hits, and step (d) further comprises electronically importing the emergency policy of a desired search hit into the emergency plan of the facility.

14. The article of manufacture of claim 13 wherein the search term is related to an emergency condition, and the imported emergency policy relates to the emergency condition.

15. The article of manufacture of claim 12 wherein the electronic network is the internet or an intranet and the user interface is accessed via an internet web browser.

16. The article of manufacture of claim 12 wherein the plurality of component parts include emergency drill procedures.

17. The article of manufacture of claim 12 wherein textual material of an emergency plan constitutes the plan's policies, and one of the component parts of the emergency plan are the emergency plan procedures, and wherein the computer-executable instructions perform a method further comprising:

(g) providing a user interface that allows sections of policies to be labeled as procedures, the user interface also allowing all previously identified procedures to be shown on a single listing for rapid review.

18. The article of manufacture of claim 12 wherein a facility is a single facility entity.

19. The article of manufacture of claim 12 wherein a facility is a network of related facility entities.

20. The article of manufacture of claim 12 wherein the computer-executable instructions perform a method further comprising:
- (g) providing via the electronic network a geographic information system (GIS) data set; and
- (h) projecting facility data onto the GIS data set, the facility data including the plurality of component parts of each emergency plan, wherein in step (c), the accessible component parts of the emergency plans are electronically shared by using the GIS data set that has the facility data projected thereon.

21. The article of manufacture of claim 12 wherein one of the component parts of the emergency plan includes emergency policies, and the computer-executable instructions perform a method further comprising:
- (g) each facility designating which emergency policies in their respective emergency plans are accessible to other facilities, wherein only emergency policies that are designated as being accessible to other facilities can be electronically shared and imported into another facility.

22. The article of manufacture of claim 12 wherein the electronic sharing is an electronic exchanging among facilities.

* * * * *